(12) United States Patent
Johnson et al.

(10) Patent No.: US 8,260,435 B2
(45) Date of Patent: Sep. 4, 2012

(54) IMPLANTABLE LEAD FOR AN ACTIVE MEDICAL DEVICE HAVING AN INDUCTOR DESIGN MINIMIZING EDDY CURRENT LOSSES

(75) Inventors: Robert Shawn Johnson, North Tonawanda, NY (US); Warren S. Dabney, Orchard Park, NY (US); Holly Noelle Moschiano, Lancaster, NY (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 84 days.

(21) Appl. No.: 13/042,177

(22) Filed: Mar. 7, 2011

(65) Prior Publication Data

US 2011/0230943 A1    Sep. 22, 2011

Related U.S. Application Data

(63) Continuation-in-part of application No. 12/891,292, filed on Sep. 27, 2010.

(60) Provisional application No. 61/314,743, filed on Mar. 17, 2010.

(51) Int. Cl.
*A61N 1/00* (2006.01)
(52) U.S. Cl. .................................................. 607/116
(58) Field of Classification Search .................. 607/116
See application file for complete search history.

(56) References Cited

U.S. PATENT DOCUMENTS

| | | | |
|---|---|---|---|
| 4,424,551 A | 1/1984 | Stevenson et al. | |
| 5,217,010 A | 6/1993 | Tsitlik et al. | |
| 5,333,095 A | 7/1994 | Stevenson et al. | |
| 6,585,763 B1 * | 7/2003 | Keilman et al. | 623/1.42 |
| 6,765,779 B2 | 7/2004 | Stevenson et al. | |
| 7,038,900 B2 | 5/2006 | Stevenson et al. | |
| 7,363,090 B2 | 4/2008 | Halperin et al. | |
| 7,535,693 B2 | 5/2009 | Stevenson et al. | |
| 2007/0112398 A1 | 5/2007 | Stevenson et al. | |
| 2008/0049376 A1 | 2/2008 | Stevenson et al. | |
| 2008/0071313 A1 | 3/2008 | Stevenson et al. | |
| 2008/0116997 A1 | 5/2008 | Dabney et al. | |
| 2008/0132987 A1 | 6/2008 | Westlund et al. | |
| 2009/0116167 A1 | 5/2009 | Stevenson et al. | |
| 2009/0259265 A1 | 10/2009 | Stevenson et al. | |
| 2010/0324640 A1 | 12/2010 | Bauer et al. | |

OTHER PUBLICATIONS

Maurits K. Konings, et al., "Heating Around Intravascular Guidewires by Resonating RF Waves," Journal of Magnetic Resonance Imaging, 2000, pp. 79-85, vol. 12, Wiley-Liss, Inc.

* cited by examiner

*Primary Examiner* — George Manuel
(74) *Attorney, Agent, or Firm* — Michael F. Scalise

(57) ABSTRACT

A shielded component or network for an active medical device (AMD) implantable lead includes an implantable lead having a length extending from a proximal end to a distal end, all external of an AMD housing, and a passive component or network disposed somewhere along the length of the implantable lead. The passive component or network including at least one inductive component having a primary magnetic field line axis. A conductive shield or housing having a primary longitudinal axis substantially surrounds the inductive component or the passive network. The inductive component's magnetic field line axis is oriented substantially orthogonally to the primary longitudinal axis of the conductive shield or housing.

52 Claims, 36 Drawing Sheets

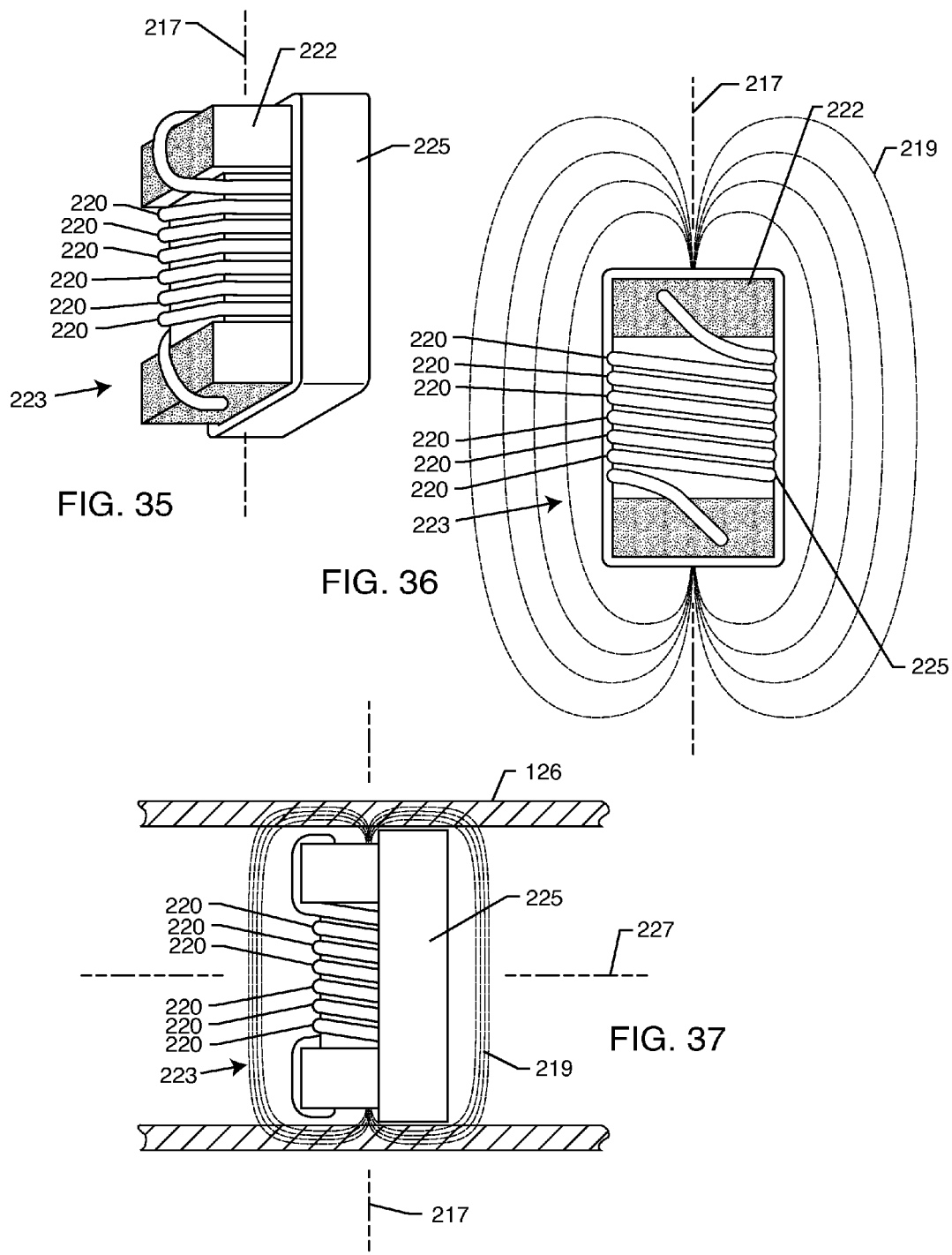

IMPLANTABLE LEAD FOR AN ACTIVE MEDICAL DEVICE HAVING AN INDUCTOR DESIGN MINIMIZING EDDY CURRENT LOSSES

FIELD OF THE INVENTION

This invention generally relates to the problem of high frequency energy induced onto implanted leads during medical diagnostic procedures such as magnetic resonant imaging (MRI). More specifically, the present invention relates to an implantable medical system comprised of an active medical device (AMD) and at least one lead extending exteriorly from a proximal end at or adjacent to the AMD, to a biological sensing or stimulating electrode at a distal end. The lead has a passive component or network including at least one inductive component disposed somewhere along its length between the proximal end and distal end. The inductive component has a primary magnetic field line axis, and is substantially surrounded by a conductive shield or housing that itself has a primary longitudinal axis oriented substantially orthogonally to the inductive component's magnetic field line axis. Such a lead-based inductor design minimizes eddy current losses.

BACKGROUND OF THE INVENTION

The radio frequency (RE) pulsed field of MRI can couple to an implanted lead in such a way that electromagnetic forces (EMFs) are induced in the lead. The amount of energy that is induced is related to a number of complex factors, but in general, is dependent upon the local electric field that is tangent to the lead and the integral of the electric field strength along the lead. In certain situations, these EMFs can cause currents to flow into distal electrodes or in the electrode interface with body tissue. It has been documented that when this current becomes excessive, overheating of said lead or its associated electrode or overheating of the associated interface with body tissue can occur. There have been cases of damage to such body tissue which has resulted in loss of capture of cardiac pacemaking pulses or tissue damage severe enough to result in brain damage or multiple amputations, and the like.

Electromagnetic interference (EMI) is also a significant issue. It has been well demonstrated through various incidents and publications that an implanted lead can act as an antenna and pick up unwanted signals from the patient environment. In the past, there have been problems with microwave ovens, cell phones, and the like. Stray signals that are picked up on implanted leads can be coupled to the interior of the AMD and interfere with sensitive electronic circuits. In cardiac pacemakers, instances of EMI being detected as normal cardiac rhythms have resulted in pacemaker inhibition which can be life-threatening.

Magnetic resonance imaging (MRI) is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AMDs after an MRI procedure, sometimes occurring many days later. Moreover, there are a number of papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the commonly available MRI units in clinical use. Some of the newer research MRI system fields can go as high as 11.7 Tesla.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of 21 MHz to 64 MHz to 128 MHz depending upon the static magnetic field strength. The frequency of the RF pulse for hydrogen scans varies by the Lamour equation with the field strength of the main static field where: RF PULSED FREQUENCY in MHz=(42.56) (STATIC FIELD STRENGTH IN TESLA). There are also phosphorous and other types of scanners wherein the Lamour equation would be different.

The third type of electromagnetic field is the time-varying magnetic gradient fields designated $B_X$, $B_Y$, $B_Z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur.

The cause of heating in an MRI environment is twofold: (a) RF field coupling to the lead can occur which induces significant local heating; and (b) currents induced between the distal tip and tissue during MRI RF pulse transmission sequences can cause local Ohms Law heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing capture threshold (PCT), venous ablation, Larynx or esophageal ablation, myocardial perforation and lead penetration, or even arrhythmias caused by scar tissue. Such long term heating effects of MRI have not been well studied yet for all types of AMD lead geometries. There can also be localized heating problems associated with various types of electrodes in addition to tip electrodes. This includes ring electrodes or pad electrodes. Ring electrodes are commonly used with a wide variety of abandoned implanted device leads including cardiac pacemakers, and neurostimulators, and the like. Pad electrodes are very common in neurostimulator applications. For example, spinal cord stimulators or deep brain stimulators can include a plurality of pad electrodes to make contact with nerve tissue. A good example of this also occurs in a cochlear implant. In a typical cochlear implant there would be sixteen pad electrodes placed up into the cochlea. Several of these pad electrodes make contact with auditory nerves.

Variations in the pacemaker lead length and implant trajectory can significantly affect how much heat is generated. A paper entitled, HEATING AROUND INTRAVASCULAR GUIDEWIRES BY RESONATING RF WAVES by Konings, et al., Journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the leads of pacemakers, ICDs, neurostimulators and the like, depends on various factors, including the strength of the static magnetic field, the pulse sequence, the strength of RE field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar, multipolar and the like. It is very important that excessive RF current not flow at the interface between the lead distal tip electrode or electrodes and body tissue. In a typical cardiac pacemaker, for example, the distal tip electrode can be passive or of a screw-in helix type as will be more fully described. In any event, it is very important that excessive RF current not flow at this junction between the distal tip electrode and, for example, into surrounding cardiac or nerve tissue. Excessive current at the distal electrode to tissue interface can cause excessive heating to the point where tissue ablation or even perforation can occur. This can be life-threatening for cardiac patients.

For neurostimulator patients, such as deep brain stimulator patients, thermal injury can cause permanent disability or even be life threatening. Similar issues exist for spinal cord stimulator patients, cochlear implant patients and the like.

A very important and possibly life-saving solution is to be able to control overheating of implanted leads during an MRI procedure. A novel and very effective approach to this is to first install parallel resonant inductor and capacitor bandstop filters at or near the distal electrode of implanted leads. For cardiac pacemaker, these are typically known as the tip and ring electrodes. One is referred to U.S. Pat. No. 7,363,090; US 2007/0112398 A1; US 2008/0071313 A1; US 2008/0049376 A1; US 2008/0024912 A1; US 2008/0132987 A1; and US 2008/0116997 A1, the contents of all of which are incorporated herein. US 2007/0112398 A1 relates generally to L-C bandstop filter assemblies, particularly of the type used in active implantable medical devices (AIMDs) such as cardiac pacemakers, cardioverter defibrillators, neurostimulators and the like, which raise the impedance of internal electronic or related wiring components of the medical device at selected frequencies in order to reduce or eliminate currents induced from undesirable electromagnetic interference (EMI) signals.

Other types of component networks may also be used in implantable leads to raise their impedance at MRI frequencies. For example, a series inductor may be used as a single element low pass filter. The inductance will tend to look like a high impedance at high frequencies, such as the RE pulsed frequencies of a typical MRI scanner. For more information on this refer to U.S. Pat. No. 5,217,010 (Tsitlik et al.), the contents of which are incorporated herein by reference.

U.S. Pat. No. 7,363,090 and US 2007/011298 A1 show resonant L-C bandstop filters placed at the distal tip and/or at various locations along the medical device leads or circuits. These L-C bandstop filters inhibit or prevent current from circulating at selected frequencies of the medical therapeutic device. For example, for an MRI system operating at 1.5 Tesla, the pulsed RE frequency is 63.84 MHz, as described by the Lamour Equation for hydrogen. The L-C bandstop filter can be designed to resonate at or near 63.84 MHz and thus create a high impedance (ideally an open circuit) in the lead system at that selected frequency. For example, the L-C bandstop filter when placed at the distal tip electrode of a pacemaker lead will significantly reduce RF currents from flowing through the distal tip electrode and into body tissue. The L-C bandstop filter also reduces EMI from flowing in the leads of a pacemaker thereby providing added EMI protection to sensitive electronic circuits. In general, the problem associated with implanted leads is minimized when there is a bandstop filter placed at or adjacent to its distal tip electrodes.

At high RF frequencies, an implanted lead acts very much as like an antenna and a transmission line. An inductance element disposed in the lead will change its transmission line characteristics. The inductance can act as its own antenna pick-up mechanism in the lead and therefore, ideally, should be shielded. When one creates a very high impedance at the distal electrode to tissue interface by installation of a resonant bandstop filter as described in U.S. Pat. No. 7,038,900 and as further described in US 2007/0112398 A1, there is created an almost open circuit which is the equivalent of an unterminated transmission line. This causes a reflection of MRI induced RF energy back towards the proximal end where the AIMD (for example, a pacemaker) is connected. In order to completely control the induced energy in an implanted lead, one must take a system approach. In particular, a methodology is needed whereby energy can be dissipated from the lead system at the proximal end in a way that does not cause overheating either at the distal electrode interface or at the proximal end cap. Maximizing energy transfer from an implanted lead is more thoroughly described in US 2010/0160997 A1, the contents of which are incorporated herein by reference.

In order to work reliably, leads need to be stably located adjacent to the tissue to be stimulated or monitored. One common mechanism for accomplishing this has been the use of a fixation helix, which exits the distal end of the lead and is screwed directly into the body tissue. The helix itself may serve as an electrode or it may serve as an anchoring mechanism to fix the position of an electrode mounted to, or forming a portion of the lead itself.

A problem associated with implanted leads is that they act as an antenna and tend to pick up stray electromagnetic signals from the surrounding environment. This is particularly problematic in an MRI environment, where the currents which are imposed on the leads can cause the leads to heat to the point where tissue damage is likely. Moreover, the currents developed in the leads during an MRI procedure can damage the sensitive electronics within the implantable medical device. Bandstop filters, such as those described in U.S. Pat. No. 7,363,090 and US 2007/0112398 A1, reduce or eliminate the transmission of damaging frequencies along the leads while allowing the desired frequencies to pass efficiently through.

Typically a surrounding casing used in a bandstop filter may be made entirely or partly from a metallic tube. However, the use of a metal tube to create the outer housing of the bandstop filter creates challenges to minimize parasitic effects on the inductor utilized in the circuit design. A metal tube will support electrical currents, such as eddy currents, which can be induced by changing electric or magnetic fields. Different designs of inductors will be affected differently by the metallic outer housing.

Accordingly, there is a need for attenuating the RF energy that can be induced onto or into an implanted lead system. Further, there is a need to provide shielding of passive network components, including any inductors that would be disposed along the length of the lead. Such shielding should reduce or prevent external electromagnetic fields from coupling RF electromagnetic energy to said passive component or network and, in particular, its inductive component(s). Moreover, there is a need for (i) an implantable medical lead where the inductor design minimizes eddy currents in the outer housing and (ii) a method to compensate for these effects. The present invention fulfills these needs and provides other related advantages.

SUMMARY OF THE INVENTION

The present invention resides in a shielded component or network for an active medical device (AMD) implantable lead, comprising: (1) an implantable lead having a length extending from a proximal end to a distal end, all external of an AMD housing, (2) a passive component or network disposed somewhere along the length of implantable lead, the passive component or network including at least one inductive component having a primary magnetic field line axis, and (3) a conductive shield or housing substantially surrounding the inductive component or the passive network, the shield or housing having a primary longitudinal axis. The inductive component's magnetic field line axis is oriented substantially orthogonally to the primary longitudinal axis of the shield or housing. There is thus provided a medical electrical lead having an inductor design minimizing eddy current losses in implantable housings. Inductors can be used in various electronic components, such as bandstop filters. Typically a lead housing may be made partly from a metallic tube. However, the use of a metallic tube to create the outer housing creates challenges to minimize parasitic effects on the inductor utilized in the circuit design. A metallic tube will support electrical currents, such as eddy currents, which can be induced by changing electric or magnetic fields. Different designs of inductors will be affected differently by the metallic tube housing. The effects of wire wound inductor types and thick film inductor types on metallic tube housings show that the thick film inductor types are less affected by the addition/removal of the tube housing than the wire wound inductors.

The passive component network may include at least one capacitive component electrically connected in parallel with the at least one inductive component to form a bandstop filter. The inductive component may comprise a solenoid inductor, a chip inductor, a Wheeler spiral or a thick film inductor, and the capacitive component may comprise a chip capacitor, parasitic capacitance, or a feedthrough capacitor. In this regard, the capacitive component may comprise parasitic capacitance formed between coils of the inductive component and/or between the inductive component and the conductive shield or housing. In a preferred embodiment, a dielectric material is disposed between coils of the inductive component and between the inductive component and the conductive shield or housing to facilitate formation of the parasitic capacitance. The capacitive component and the inductive component may form a parallel resonant bandstop filter and are tuned to impede induced current flow through the implantable lead at a selected center frequency or range of frequencies, typically comprising an MRI RF pulsed frequency or range of RF pulsed frequencies. The MRI RF pulsed frequency range includes tens of kilohertz, hundreds of kilohertz or megahertz.

A non-conductive insulator or dielectric material may be disposed between the passive component network and the conductive shield or housing.

In a preferred embodiment, an inductor is provided having first and second conductive terminals in spaced non-conductive relation, and a capacitor is also provided having first and second conductive terminals in spaced non-conductive relation. The inductor and the capacitor are physically disposed in series relative to one another, and are electrically connected to one another in parallel to form a bandstop filter. One of the first or second conductive terminals of the inductor is disposed generally adjacent to one of the first or second conductive terminals of the capacitor. The capacitor and the inductor may be aligned along a common axis, and the adjacent conductive terminals of the inductor and the capacitor may abut one another. An electrical insulator may also be disposed between the adjacent conductive terminals of the inductor and the capacitor. The electrical potential between the adjacent conductive terminals of the inductor and the capacitor is preferably minimized, and is, ideally, zero.

The second conductive terminal of the inductor may be conductively coupled to the first conductive terminal of the capacitor, and the first conductive terminal of the inductor may be conductively coupled to the second conductive terminal of the capacitor.

A plurality of paired inductor and capacitor bandstop filters may be provided, wherein each bandstop filter is physically disposed in series relative to one another. In this case, each paired inductor and capacitor is electrically connected in series to another paired inductor and capacitor. The bandstop filters are tuned to impede induced current flow through the implanted lead at different respective selected MRI RF pulsed center frequencies or ranges of RF pulsed frequencies.

The capacitive component and the inductive component may comprise biocompatible and non-migratable materials and/or they may be disposed within a medically sealed container which forms the conductive shield or housing. The hermetically sealed container also forms a conductive shield and may comprise a biocompatible housing in which the bandstop filter is disposed, and biocompatible first and second conductive contacts extending through and in non-conductive relation with the housing, which are conductively coupled in series to the bandstop filter. Typically, the hermetically sealed container is disposed in series in the implantable lead, wherein first and second contacts of the hermetically sealed container are connected to, respectively, proximal and distal portions of the lead.

A substrate may be provided onto which the inductor and capacitor are fixed in a pre-assembly prior to insertion into the biocompatible shield housing. First and second hermetic terminals hermetically sealed to the biocompatible housing after the pre-assembly is inserted therein may comprise at least a portion of the first and second conductive contacts, respectively. An electrically insulated conformal coating may be applied over at least a portion of the hermetically sealed container.

The overall Q of the bandstop filter is selected to balance impedance at the selected frequency versus frequency bandwidth characteristics. When the Q of the inductive component is relatively high, the Q of the capacitive component is relatively low such that the inductive component has a relatively low resistive loss and the capacitive component has a relatively high equivalent series resistance. When the Q of the inductive component is relatively low and the Q of the capacitive component is relatively high, the inductive component has a relatively high resistive loss and the capacitive component has a relatively low equivalent series resistance.

An impeding circuit may be provided for raising the high frequency impedance of the implantable lead. The impedance circuit may comprise an inductor and/or a bandstop filter.

The inductive component may comprise a plurality of spaced apart inductive components disposed along the length of the implantable lead. In this case, not all of the inductive components need be shielded. Further, the conductive shield or housing may comprise a plurality of conductive shields disposed along the length of the implantable lead.

The conductive shield or housing may comprise a conductive heat-shrink tubing, a conductive foil, wire, braid, mesh, circuit trace, or solid tubular material, or a conductive polymer, a conductive epoxy, carbon nano-fibers, nano-meshes, nano-coatings or nano-threads. The conductive shield or housing is further typically radially spaced from the passive component network.

The conductive shield or housing may comprise MP35N, carbon, platinum, titanium, palladium, chromium, Wolfram, tungsten, gold, copper, or alloys thereof. The implantable lead may comprise a plurality of implantable leads substantially surrounded by the conductive shield or housing. The AMD may comprise an implantable hearing device, a cochlear implant, a pisoelectric soundbridge transducer, a neurostimulator, a brain stimulator, a cardiac pacemaker, a left ventricular assist device, an artificial heart, a drug pump, an implantable bone growth stimulator, a urinary incontinence device, a spinal cord stimulator, an anti-tremor stimulator, an implantable cardioverter defibrillator, or a congestive heart failure device.

The conductive shield or housing may comprise a housing for a passive fixation tip electrode or may be associated with a translational active fixation tip, wherein the housing for the active fixation tip comprises the conductive shield or housing. Alternatively, the conductive shield or housing may be disposed within a housing for the active fixation tip.

The network may include an active electronic circuit.

The conductive shield or housing may comprise a non-metallic material such as sapphire, ruby, alumina and/or ceramic materials which have a thin conductive coating deposited thereon by plating, chemical vapor deposition, sputtering, physical application, cladding or the like.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 35 is a perspective view of an exemplary wire wound-type inductor;

FIG. 36 is a top view of the structure of FIG. 35;

FIG. 37 is a side view of the structure of FIG. 35;

DETAILED DESCRIPTION OF THE PREFERRED EMBODIMENTS

Figure 1:
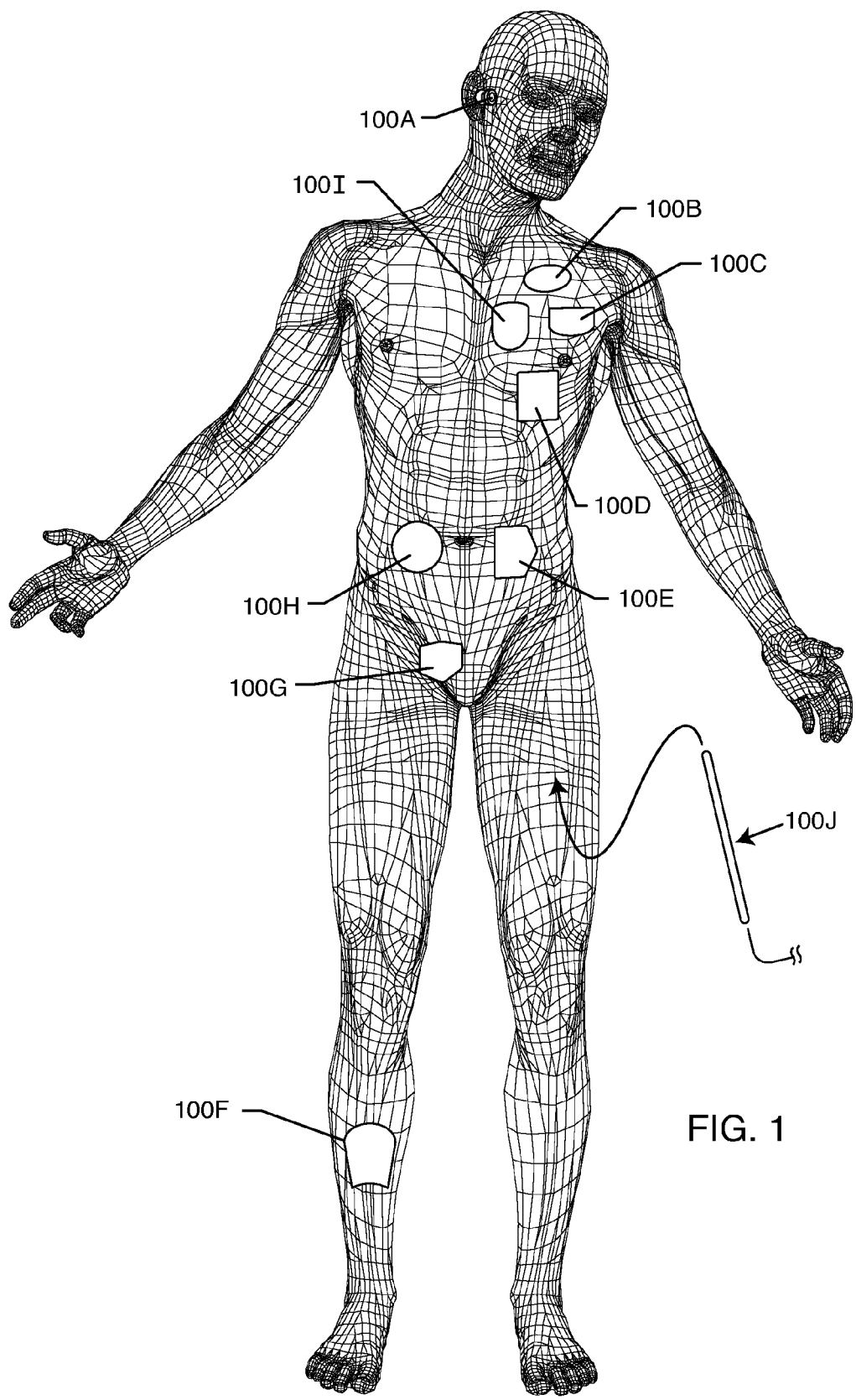
FIG. 1 is a wire-formed diagram of a generic human body showing a number of exemplary active medical devices (AMDs)

As shown in the drawings for purposes of illustration, the present invention relates to a system for RF shielding of a passive component or network disposed along the length of implanted leads of active medical devices (AMDs). In particular, the conductive RF shielding is to shield and/or hermetically seal a passive inductor or inductive component in the presence of high power electromagnetic field environments, such as the RF pulsed fields produced by a clinical MRI scanner. In a broad sense, the present invention comprises an active medical device system including an implanted lead having RE shielded inductors or passive network components including inductors. The implanted lead may be coaxial, rectangular, flat or other geometries. US 2009/0243756 is incorporated herein by reference. Furthermore, the implanted lead may consist of a number of internal conductors, such as a bipolar lead for cardiac pacemaker channel or even an eight or sixteen conductor spinal cord stimulator implanted lead. This is also known as a multichannel lead system. The networks of the present invention can also include active components in combination with at least one inductor. These active networks can comprise a portion of a lead-based sensor, such as a hemodynamic sensor, a pulse oxygen sensor, an acceleration or rate sensor, and the like. In addition, the inductors of the present invention can be a part of an energy harvesting device or circuit which is implanted in the human body. US 2009/0243756 is incorporated by reference herein.

In general, the conductive shield or housing of the present invention surrounds all of the passive or active component elements disposed along the length of an implanted lead, including, but not limited to, inductors, inductor-capacitor (L-C) bandstop filters, L-C trap filters, or single or multi-element low pass filters. It is important that the conductive shield or housing surround at least the inductor component(s) associated with such electronic networks. As a practical matter, the conductive shield or housing would generally encompass all of the passive components. The conductive shield or housing could also surround all of the conductors in a particular implanted lead that is routed to a particular area of body tissue. For example, in a cardiac pacemaker application, there are often dual chamber bipolar conductors in the implanted lead, wherein one lead is typically routed to the right ventricle and the other to the right atrium. Each of these implanted leads, consisting of two conductors, would have its own passive component filtering elements which would be individually shielded. Typically, conforming to the shape of the leads, the conductive shields of the present invention may be coaxial, flat, rectangular or any other geometry suitable for either tunneling or for transvenous insertion within the human body.

In a particularly preferred form, the inductive component has a primary magnetic field line axis, and the conductive shield or housing substantially surrounds the inductive component or the passive network, wherein the shield or housing has a primary longitudinal axis. The inductive component's magnetic field line axis is oriented substantially orthogonally to the primary longitudinal axis of the shield or housing.

The conductive shield or housing can also act as an energy dissipating surface. Diverting circuits, consisting of either capacitors, low-pass filter, L-C trap filters or high-pass filters, can be used to divert energy from an implanted lead to its surrounding shield. The shield, in a preferred embodiment, is in contact with body tissue whereby induced RF energy from the lead is diverted to the shield, which in turn acts as an energy dissipating surface (EDS). US 2010/0023000 A1 is incorporated herein by reference.

Implanted leads have both a characteristic impedance and also act as a transmission line. They tend to effectively couple energy from an external electromagnetic interference emitter as a function of theft wavelength. This also varies with lead trajectory, design and other factors. However, when one is only concerned with particular frequency ranges, for example the RF pulse frequency of MRI, it is not necessary to shield the entire lead. In this regard, one could shield a significant portion of the lead so that the exposed (unshielded) portion of the lead was significantly less than a half or a quarter wavelength in body tissue. This makes the remaining unshielded lead portion a very inefficient antenna and therefore it would only pick up a very small amount of induced energy. Accordingly, one could shield passive network components or inductances disposed along the length of the shield and could also shield adjoining sections of the lead itself. By shielding a portion of the implanted lead or even segments of the implanted lead, one would break up its resonant lengths thereby making it a very ineffective antenna over a broad range of MRI pulsed frequencies.

The conductive shields of the present invention can be a solid conductor, wound spiral conductors, meshes, tubing, nano-coatings or the like. In the preferred embodiment, the shield would present a fairly homogenous conductive surface such that it would effectively reflect and/or absorb incident electromagnetic fields. However, complete shielding is really not necessary. Accordingly, the shield could be loosely woven such that only a portion of the electromagnetic interference was intercepted.

The invention further resides in a combination of shields with one or more impeding circuits which could also be optimally combined with one or more diversion circuits. The impeding circuits typically would consist of either inductors or L-C parallel resonant-bandstop filters. The diversion circuits would typically consist of a capacitor, a multi-element low-pass filter, a high-pass filter, or an L-C trap filter. The operation of impeding circuits and diversion circuits is more thoroughly described in US 2010/0023000 A1 and US 2010/0160997 A1, which are incorporated by reference. In a particularly preferred embodiment, the conductive shield or housing of the present invention is used in combination with an impeding circuit known as a bandstop filter. The bandstop filter has a Q and 3-dB bandwidth such that, at resonance, it offers attenuation of at least 10 dB over a range of MRI RF pulsed frequencies at least 10 kHz wide, and more preferably at least 100 kHz or even on the order of MHz wide.

In the case where bandstop filters are installed at or near the distal electrode of an implanted lead, the RF energy induced by the MRI pulse field is inhibited from flowing into body tissues and thereby being dissipated. However, even when distal electrode bandstop filters are used, that energy still resides in the lead system. In other words, by preventing this induced energy from flowing to sensitive tissues at distal electrode interfaces, a great deal has been accomplished; however, it is still important to carefully dissipate the remaining energy that is trapped in the lead system.

In order to provide optimal decoupling of RF energy from an implanted lead to the energy dissipating surface of a shield, one should consider Thevenin's maximum power transfer theorem. It is well known in electrical engineering that to transfer maximum power to a load, the load impedance must be equal to the source impedance. If the source impedance is completely resistive, for example, 50 ohms, then to transfer maximum power the load impedance would have to be 50 ohms. When the source impedance is reactive, then to transfer maximum power to another location the load impedance should have the opposite sign of reactance and the same impedance and resistance. In a typical implanted lead system, the implanted leads typically appear inductive. Accordingly, having a capacitive energy diversion circuit to couple energy from the lead conductors to the EDS shield surface, one has at least some cancellation of these imaginary impedance factors. In electrical engineering, the inductance of the lead would be denoted by $+j\omega L$. The impedance of the capacitor, on the other hand, is a $-j/\omega C$ term. Transferring maximal energy from a lead to an energy dissipating surface is more thoroughly described in U.S. Pat. No. 7,689,288 the contents of which are incorporated herein. It is desirable that the inductive elements of the impeding circuits be shielded in accordance with the present invention in order to minimize eddy current losses.

FIG. 1 is a wire formed diagram of a generic human body showing a number of exemplary implanted medical devices. 100A is a family of implantable hearing devices which can include the group of cochlear implants, piezoelectric sound bridge transducers and the like. 100B includes an entire variety of neurostimulators and brain stimulators. 100C shows a cardiac pacemaker. 100D includes the family of left ventricular assist devices (LVAD's) and artificial hearts. 100E includes an entire family of drug pumps which can be used for dispensing of insulin, chemotherapy drugs, pain medications and the like. 100F includes a variety of implantable bone growth stimulators for rapid healing of fractures. 100G includes urinary incontinence devices. 100H includes the family of pain relief spinal cord stimulators and anti-tremor stimulators. 100I includes a family of implantable cardioverter defibrillator (ICD) devices, congestive heart failure devices (CHF), and cardio resynchronization therapy devices, otherwise known as CRT devices. 110J illustrates a family of probes or catheters that can be transvenously inserted during catheter lab procedures. These are normally considered short-term implants in that they are inserted within the human body for at most a few hours.

The various types of active medical devices (AMDs) illustrated in FIG. 1 generally represent any type of AIMD that is considered a "long-term" implant. This is in direct contrast to things like probes or catheters or surgical devices that are "short-term" body insertions. For example, a probe or catheter is typically used in a cath-lab situation wherein it is temporarily inserted through a femoral (or other) artery where the entire procedure lasts minutes or at most a few hours. On the other hand, a long-term implant, such as a cardiac pacemaker, is generally designed to be implanted in the human body for many years. There are significant differences in the art between a short-term and a long-term implant. For example, for a long-term implant, one has to worry greatly about the long-term biocompatibility, toxicity and even the hermeticity of the implant. In contrast, a probe, catheter or temporary loop recorder need only operate or be reliable for a matter of minutes or even hours. In general, a short-term implant is often considered to be a disposable device. In addition, the FDA regulatory approval processes for long-term implants is significantly different and involves much more rigorous testing and product safety and reliability criteria. The FDA Center for Devices and Radiological Health (FDA-CDRH) is the responsible regulatory agency for long-term cardiac implants. As used herein, the term active medical device (AMD) is construed to include long-term implants and also short-term body insertions, such as probes or catheters. The term AMD is inclusive of active implantable medical devices (AIMDs) and also externally worn medical devices that are associated with an implanted lead.

Throughout, the term lead generally refers to implantable leads and their conductors that are external to the housing of the active medical device. These leads tend to have a proximal end, which is at or adjacent to the AMD, and a distal end, which typically includes one or more electrodes which are in contact with body tissue.

Figure 2:
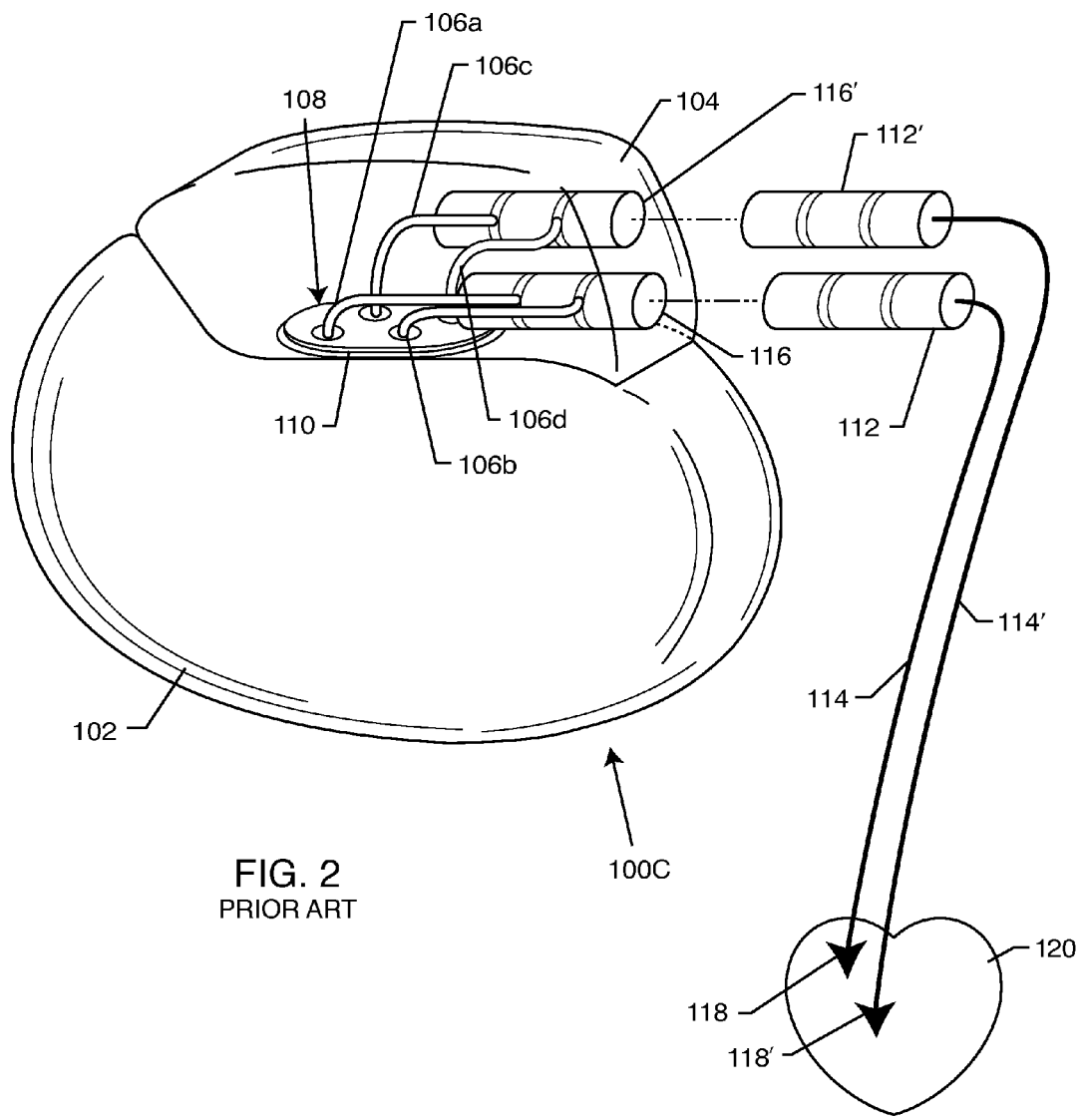
FIG. 2 illustrates an exemplary prior art cardiac pacemaker with the leads schematically shown extending to a patient's heart.

FIG. 2 is a drawing of a typical cardiac pacemaker 100C showing a titanium case or housing 102 and an IS-1 header connector block 104. The titanium case or housing 102 is hermetically sealed, however there is a point where leadwires 106a-106d must ingress and egress a hermetic seal. This is accomplished by providing a hermetic terminal assembly 108 that generally consists of a ferrule 110 which is laser welded to the titanium housing 102 of the pacemaker 100C.

Four leadwires are shown consisting of leadwire pair 106a and 106b and leadwire pair 106c and 106d. This is typical of what is known as a dual chamber bipolar cardiac pacemaker. The IS-1 connectors 112 and 112' of leads 114 and 114' are designed to plug into receptacles 116 and 116' in the header block 104. The receptacles 116 and 116' are low voltage (pacemaker) connectors covered by an ANSI/AAMI ISO standard IS-1. Higher voltage devices, such as implantable cardioverter defibrillators (ICDs), are covered by ANSI/AAMI ISO standard DF-1. A new standard which will integrate both high voltage and low voltage connectors into a miniature in-line quadripolar connector is known as the IS-4 series. The implanted leads 114 and 114' are typically routed transvenously in a pacemaker application down into the right atrium 118 and the right ventricle 118' of the heart 120. New generation biventricular or CRT-P devices may introduce leads to the outside of the left ventricle, which devices have proven to be very effective in cardiac resynchronization and treating congestive heart failure (CHF).

Although the present invention will be described herein in the context and environment of a cardiac pacemaker 100C and its associated leads 114 and 114', the present invention may also be advantageously utilized in many other types of AMDs as briefly outlined above, as well as in other commercial electronic, military, aerospace and other applications. In the following discussion, to the extent practicable, functionally equivalent components will retain the same or a similar reference number, irrespective of the particular embodiment being described.

Figure 3:
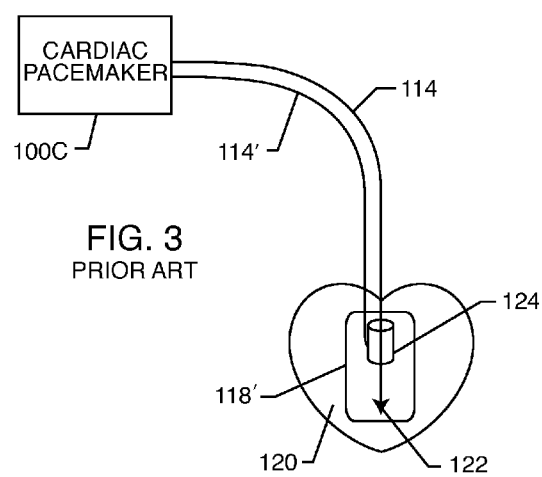
FIG. 3 is a schematic illustration of a prior art AMD with a bipolar lead.

FIG. 3 illustrates a prior art single chamber bipolar device 1000 and lead system 114 and 114' with a distal tip electrode 122 and a ring electrode 124 typically as used with the cardiac pacemaker 100C. Should the patient be exposed to the fields of an MRI scanner or other powerful emitter used during a medical diagnostic procedure, currents that are directly induced in the lead system 114, 114' can cause heating by $I^2R$ losses in the lead system or by heating caused by RF current flowing from the tip and ring electrodes 122, 124 into body tissue. If these induced RF currents become excessive, the associated heating can cause damage or even destructive ablation to body tissue.

Figure 4:
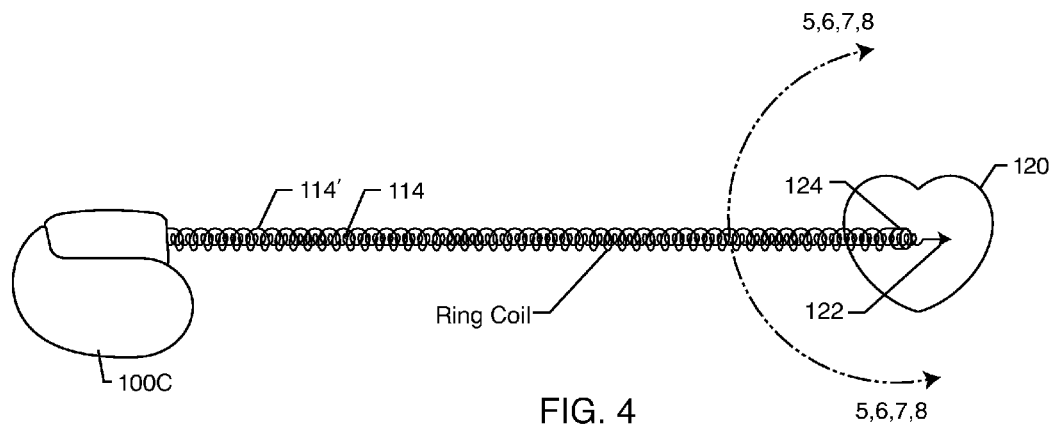
FIG. 4 is similar to FIG. 3, except that the bipolar lead wires are coaxially wound around one another.

FIG. 4 illustrates a single chamber bipolar cardiac pacemaker 1000, and leads 114 and 114' having distal tip 122 and distal ring 124 electrodes. This is a spiral wound (coaxial) system where the ring coil 114' is wrapped around the tip coil 114. There are other types of pacemaker leadwire systems in which these two leads lay parallel to one another (known as a bifilar lead system), which are not shown.

Figure 5:
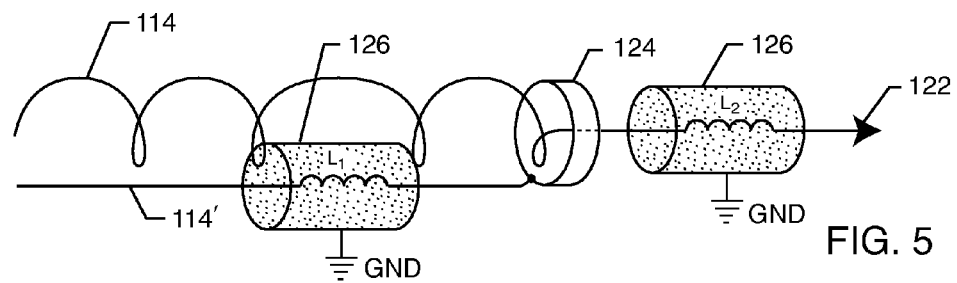
FIG. 5 is an enlarged schematic view of the area indicated by line 5-5 from FIG. 4, and illustrates an inductor disposed in series with each of a pacemaker tip and ring electrode circuits.

FIG. 5 is taken from section 5-5 of FIG. 4 and illustrates an inductor L disposed in series with each of a pacemaker tip and ring electrode circuits. The inductor L acts as a single element low pass filter and tends to attenuate the flow of current at high frequencies, such as MRI RF pulsed frequencies. The operation of inductors disposed in implantable lead wires is more thoroughly described in U.S. Pat. No. 5,217,010, the contents of which are incorporated herein. The shaded areas 126 in FIG. 5 illustrate that each of the inductors $L_1$ and $L_2$ has been shielded in accordance with the present invention. This protects the inductors $L_1$ and $L_2$ from picking up stray electromagnetic interference (EMI) from powerful RF fields of medical diagnostic equipment, such as an MRI scanner. For simplicity, the shields 126 are shown with a ground symbol (GND) indicating that they can be grounded in a number of ways. The important thing is that the shield 126 be able to reflect, absorb and dissipate RF energy that couples onto it. Electromagnetic shields both absorb and reflect incident high frequency energy. The energy that is reflected is not coupled onto the implanted lead. However, the energy that is absorbed is best converted to heat and dissipated into surrounding body tissues. Another method of grounding the shields is to connect a conductor back to the conductive housing 102 of the AMD itself. In general, the arrangement for a cardiac pacemaker shown in FIG. 5 is preferable in that the tip electrode inductor $L_2$ and the ring electrode inductor $L_1$ are individually shielded. It would be undesirable to have an overall electromagnetic shield to shield both the tip inductor $L_2$, the ring electrode 124 and the ring inductor $L_1$. This is because important cardiac pacing and biological signal sensing functions occur between the electrodes 122 and 124. Overall shielding of both tip and ring electrodes would impair said functions.

Figure 6:
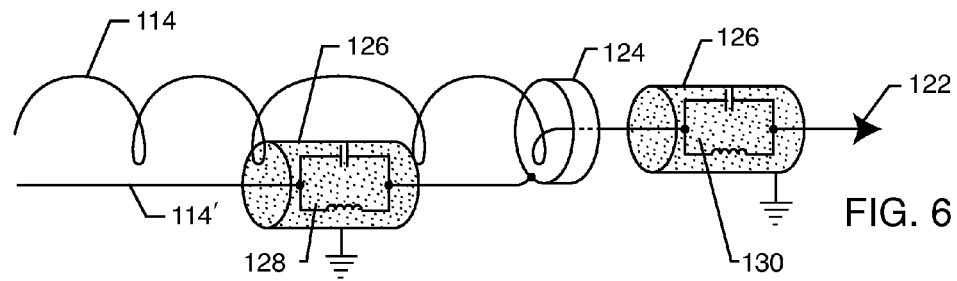
FIG. 6 is similar to FIG. 5 except that the inductor elements have been replaced by bandstop filters.

FIG. 6 is taken from section 6-6 of FIG. 4 and is very similar to FIG. 5. In this case, the inductor elements $L_1$ and $L_2$ have been replaced by L-C bandstop filters 128 and 130. In general, the shielded bandstop filters would be tuned to be resonant at a center frequency in a range of MRI RF pulsed frequencies. The operation of bandstop filters in implanted leads is more thoroughly described by U.S. Pat. No. 7,363,090 and US 2007/0112398, the contents of which are incorporated herein by reference.

Figure 7:
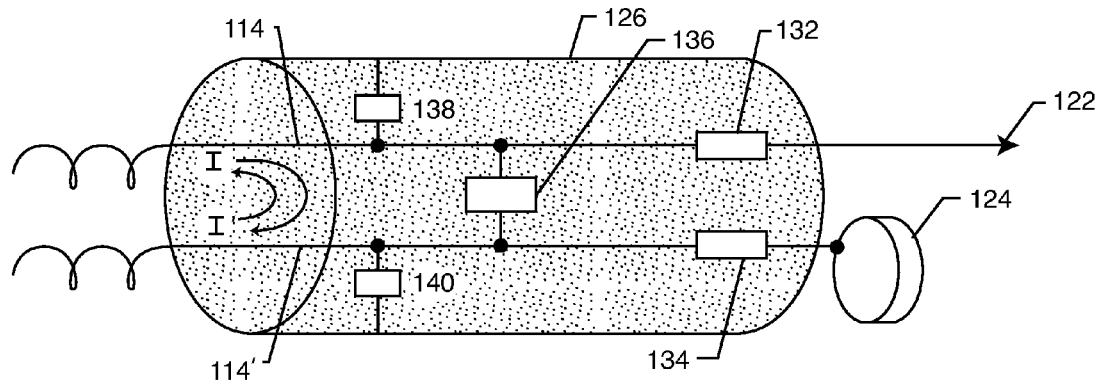
FIG. 7 is taken of the area indicated by line 7-7 from FIG. 4 and is similar to FIGS. 5 and 6, except that an overall shield encompasses various impeder and diverter elements.

FIG. 7 illustrates an AMD bipolar lead system similar to that described in FIGS. 5 and 6 except that an overall shield 126 encompasses various impeder elements 132 and 134 as well as diverter elements 136, 138 and 140. In this case, the impeder elements 132 and 134 could be inductors or bandstop filters as previously taught in FIGS. 5 and 6. The diverter elements could be capacitors or L-C trap filters as taught in U.S. Pat. No. 7,689,288, the contents of which are incorporated herein. In this case, both the tip electrode 122 and the ring electrode 124 are disposed outside the single shield 126 so they can still perform their vital cardiac pacing and biological sensing functions.

Figure 8:
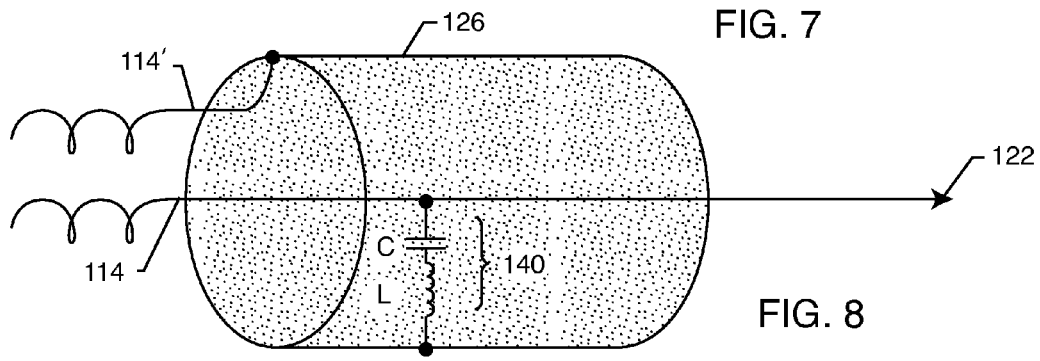
FIG. 8 is similar to FIG. 7, and illustrates a diverter element consisting of an inductor in series with a capacitor to form an L-C trap filter.

FIG. 8 is very similar to FIG. 7 and illustrates a diverter element 140 consisting of an inductor L in series with a capacitor C, forming what is known as an L-C trap filter. The operation of these trap filters is described in U.S. Pat. No. 7,689,288. The shield 126 protects the inductive component L of the L-C trap filter from picking up unwanted electromagnetic interference, for example, in an MRI RF field environment.

Figure 9:
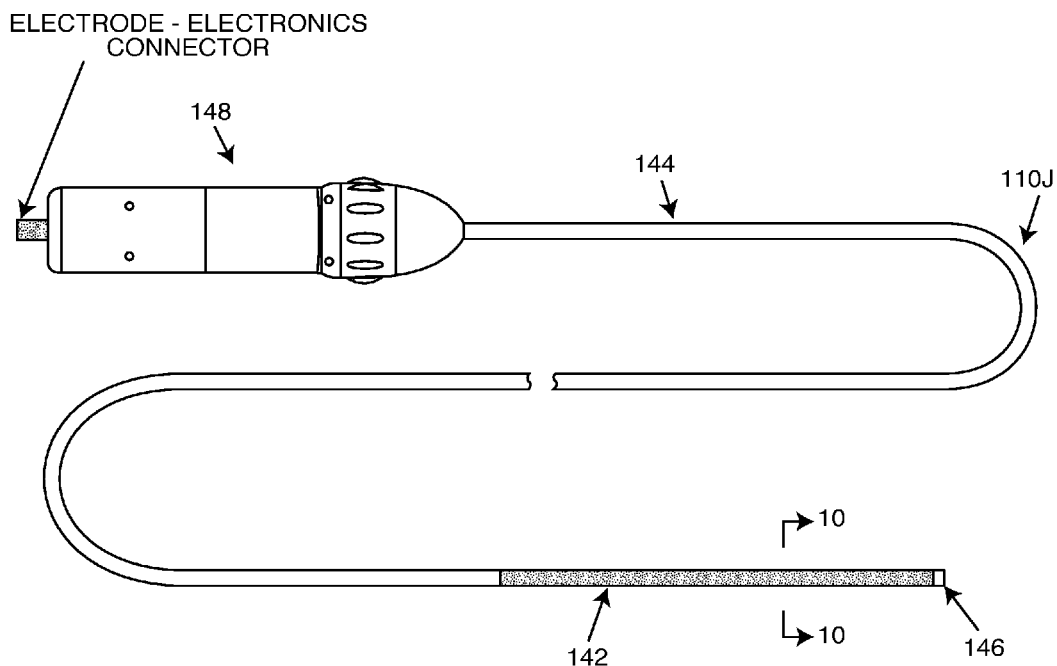
FIG. 9 illustrates a probe or catheter which has a shielded section embodying the present invention.
Figure 10:
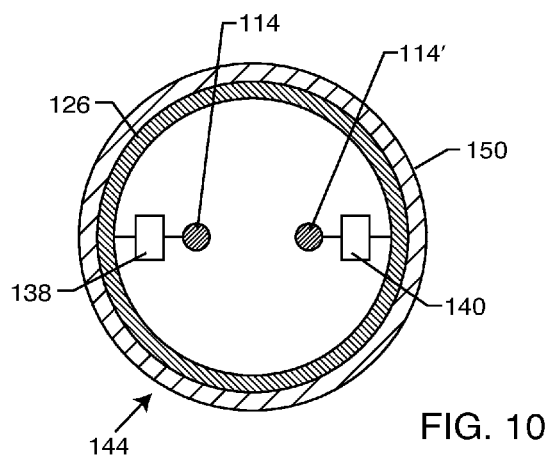
FIG. 10 is an enlarged sectional view taken along line 10-10 from FIG. 9.

FIG. 9 illustrates a probe or a catheter 100J which has a shielded section 142 which encompasses inductors or electronic networks of the present invention. The probe or catheter 100J consists of the flexible and steerable probe or catheter section 144 which may be bent as shown and generally terminates in one or more distal electrodes 146. These distal electrodes consist of mapping electrodes, ablation electrodes and the like. There is generally a catheter handle or body 148 which is used for steering the probe or catheter into the body transvenously. These handles can take the form of a pistol grip or many other shapes FIG. 10 is taken from section 10-10 of FIG. 9 and shows two leads inside the flexible portion 144 of the probe or catheter. Shown are diverter elements 138 and 140 which are connected between each of the leads 114 and 114' to the electromagnetic shield 126 of the present invention. In a preferred embodiment, the diverter elements would be L-C trap filters which would be used to divert energy picked up on the leads 114 and 114' to the shield surface 126. An optional insulation sleeve 150 is shown, which is generally undesirable. In other words, it is preferable that the conductive shield 126 be in contact with body tissue so that it dissipates unwanted MRI RF energy over a large surface area. The electromagnetic shield 126 of the present invention protects the inductor element of the L-C trap filters 138 and 140 from picking up unwanted high frequency RF energy.

In the description of the various embodiments shown in the accompanying drawings, the functionally equivalent components shall have the same reference number.

Figure 11:
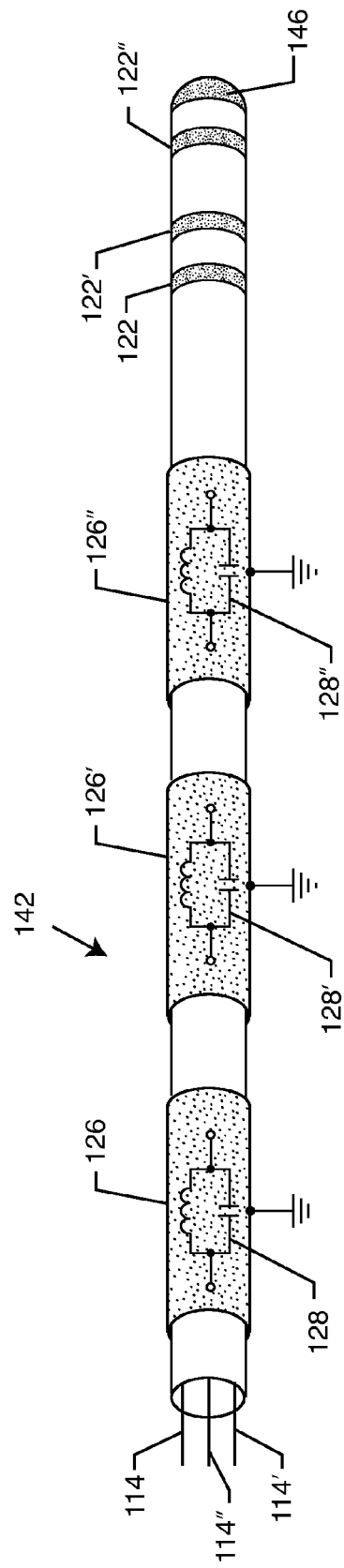
FIG. 11 is an enlarged view of the distal tip section of the probe or catheter of FIG. 9.

FIG. 11 is an alternative to the shielded portion 142 of the probe or catheter 100J illustrated in FIGS. 9 and 10. In this case, there are three internal conductors 114, 114' and 114" disposed within the flexible catheter portion 142. There are also three segmented shields 126, 126' and 126" for a respective bandstop filter 128, 128' and 128". Each of the bandstop filters 128, 128' and 128" are connected in series with a respective one of the catheter conductors. In this case, the shields 126, 126' and 126" could be continuous or segmented as shown. There is an advantage to segmented shields as this promotes the flexibility of an implanted probe, catheter or AMD lead. In addition, segmented shield sections break up transmission line type resonances and change the wavelength of the implanted lead to make it a much less efficient RF antenna. One can see that there are sensing electrodes 122, 122' and 122" for mapping biological signals, and a tip electrode 146 for ablating or creating scar tissue to eliminate unwanted arrhythmias such as atrial fibrillation.

Figure 12:
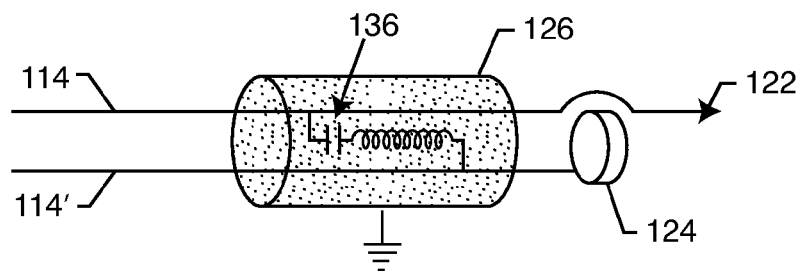
FIG. 12 is similar to FIG. 5 except that it has a single shield for a differential mode L-C trap filter.

FIG. 12 is very similar to FIG. 5 except that it has a single shield 126 which shields an L-C trap filter 136 which is connected between lead 114 and lead 114'. In the art, this is known as a differential mode L-C trap filter.

Figure 13:
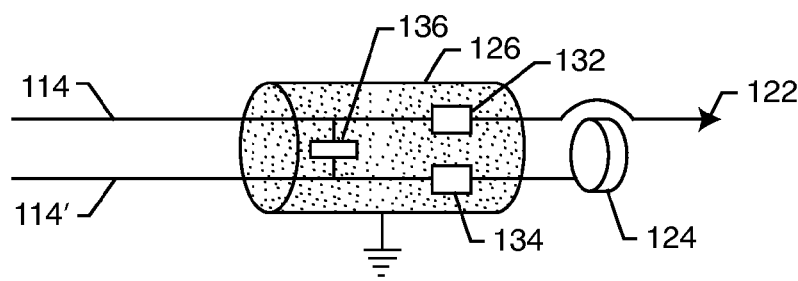
FIG. 13 is similar to HG, 12, except that the L-C trap filter has been replaced by a general diverter element.

FIG. 13 is similar to FIG. 12 except that the L-C trap filter 136 has been replaced by a general diverter element. In this case, the diverter element 36 can be an L-C trap filter, a number of multi-element low pass filters or single element capacitive filters. These are shown combined with impeder elements 132 and 134. The impeder element would typically include an inductive component.

Figure 14:
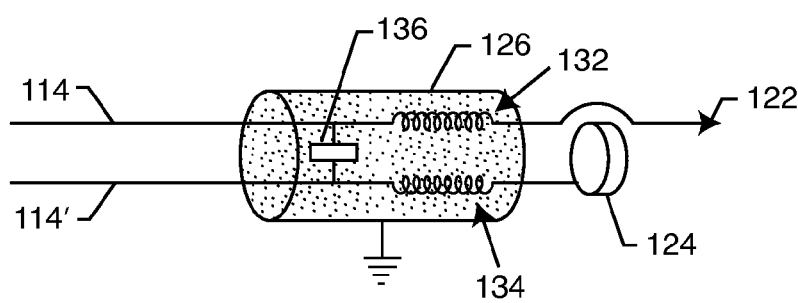
FIG. 14 is similar to FIG. 13, wherein the impeder elements are inductors.

FIG. 14 illustrates the embodiment of FIG. 13 wherein the impeder elements 132 and 134 are inductors.

Figure 15:
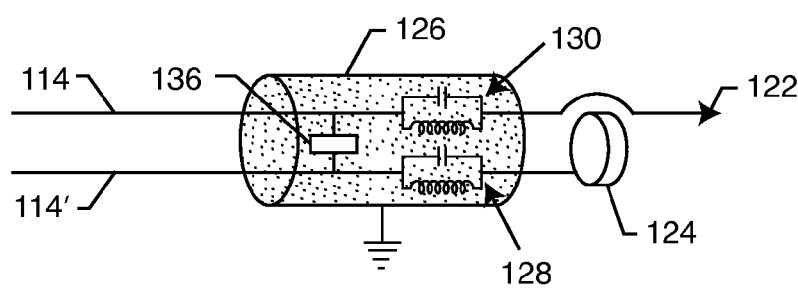
FIG. 15 is similar to FIGS. 13 and 14, wherein the impeder elements are bandstop filters.

FIG. 15 is very similar to FIG. 13 wherein the impeder elements are bandstop filters 128 and 130. These bandstop filters would normally be tuned to be resonant at an MRI RF pulsed frequency or range of frequencies.

Figure 16:
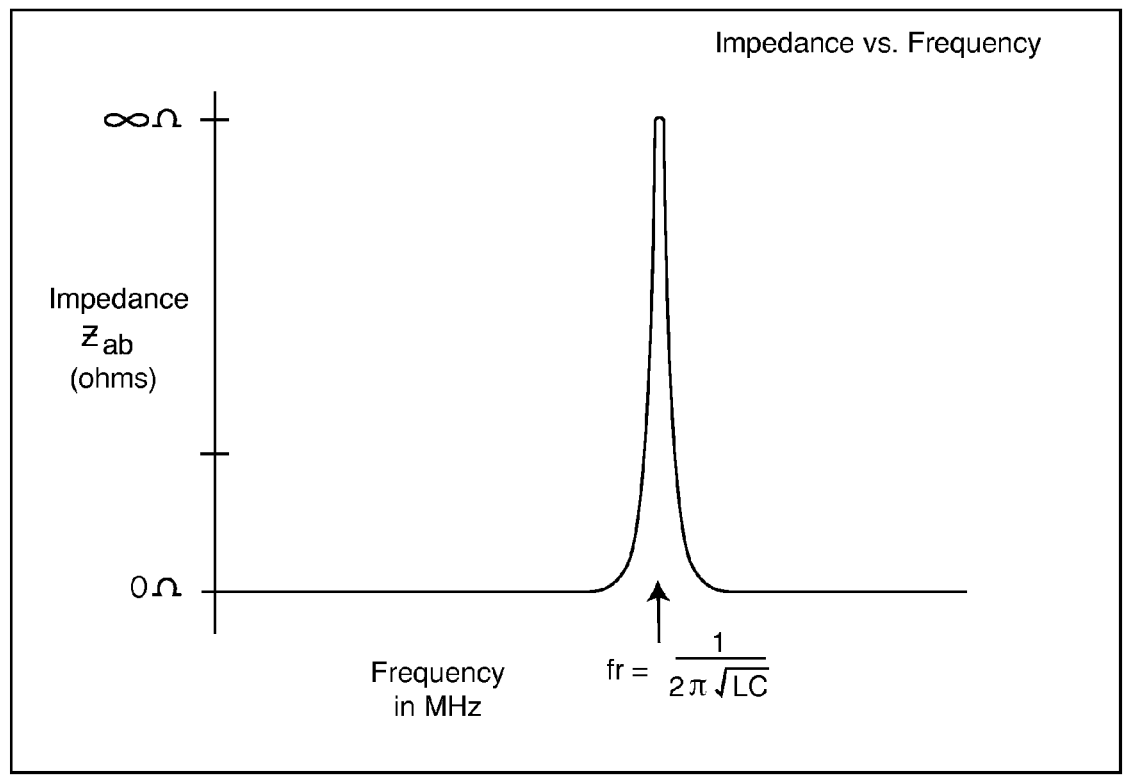
FIG. 16 is a graph showing impedance versus frequency for the ideal bandstop filter circuit of FIGS. 6 and 15.

FIG. 16 is a graph showing impedance versus frequency for the ideal parallel bandstop filter circuit 130 of FIG. 6 or 15. As one can see, using ideal (zero resistance) circuit components, the impedance measured between the lead 114 and the tip electrode 122 is zero until one approaches the resonant frequency $f_r$. At the frequency of resonance, these ideal components (the parallel inductor L and capacitor C) resonate together to approach an infinite impedance. In general, the frequency of resonance $f_r$ is given by the equation shown in FIG. 16 and is selected to be the center frequency of an MRI RF pulsed frequency. For example, for a 1.5 Tesla hydrogen scanner, the RF pulsed frequency as determined by the Lamour equation is 42.56 times the magnetic field strength in Tesla. This is approximately 63.84 MHz. Accordingly, the resonant frequency of the bandstop filter 130 would be selected to be centered approximately around 63.84 MHz.

It should be noted that not all 1.5 Tesla MRI scanners have exactly the same static magnetic field strength. This results in variation of the RF pulsed frequency by over ½ MHz. It is desirable that the bandstop filters 128 and 130 provide substantial attenuation or 3 dB bandwidth over this entire range. Similar variations occur for other commonly labeled MRI scanners, such as 3 Tesla scanners.

Figure 17:
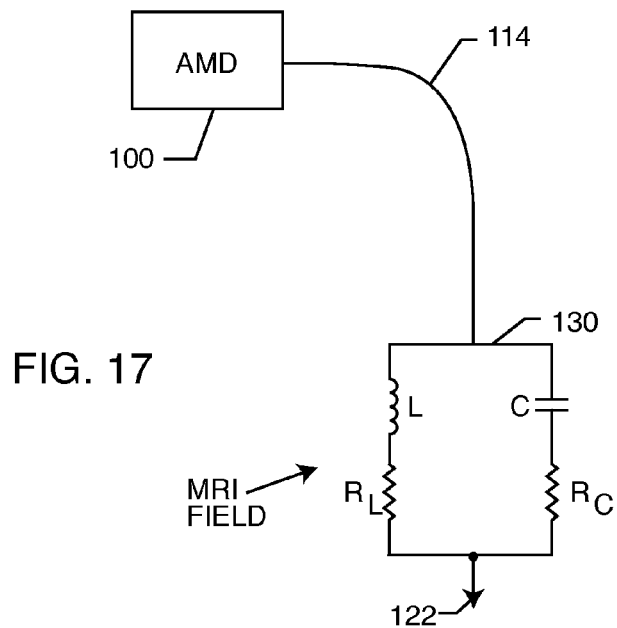
FIG. 17 is a schematic illustration similar to FIG. 3, showing a generic unipolar AMD and lead with a bandstop filter added at or near a distal electrode.

FIG. 17 is a drawing of a generic unipolar AMD 100 and lead 114, with a bandstop filter 130 added at or near the distal electrode 122. The inductor L has a resistance element $R_L$ in series with it. The capacitor C also has a resistance $R_C$ in series with it. The resistances $R_L$ and $R_C$ can be separate discrete resistors or they are losses of the inductor and capacitor elements themselves. In general, the resistance $R_L$ will be the resistance of the circuit traces or wires used to form the inductor L. The capacitor C has ohmic losses $R_C$ due to the resistance of its internal electrode plates, connection to its electrode plates, and dielectric losses. In the capacitor industry this is known as the capacitor's equivalent series resistance or ESR. The bandstop filter circuit 130 illustrated in FIG. 17 is a "real" bandstop filter in that the resistive losses are included. This makes it distinct from the ideal bandstop filter circuit shown in FIGS. 6 and 15. The presence of the bandstop filter 130 will present a very high impedance over a specific range of MRI RF pulsed frequencies to prevent currents from circulating through the distal electrode 122 into body tissue at this specific frequency range.

Figure 18:
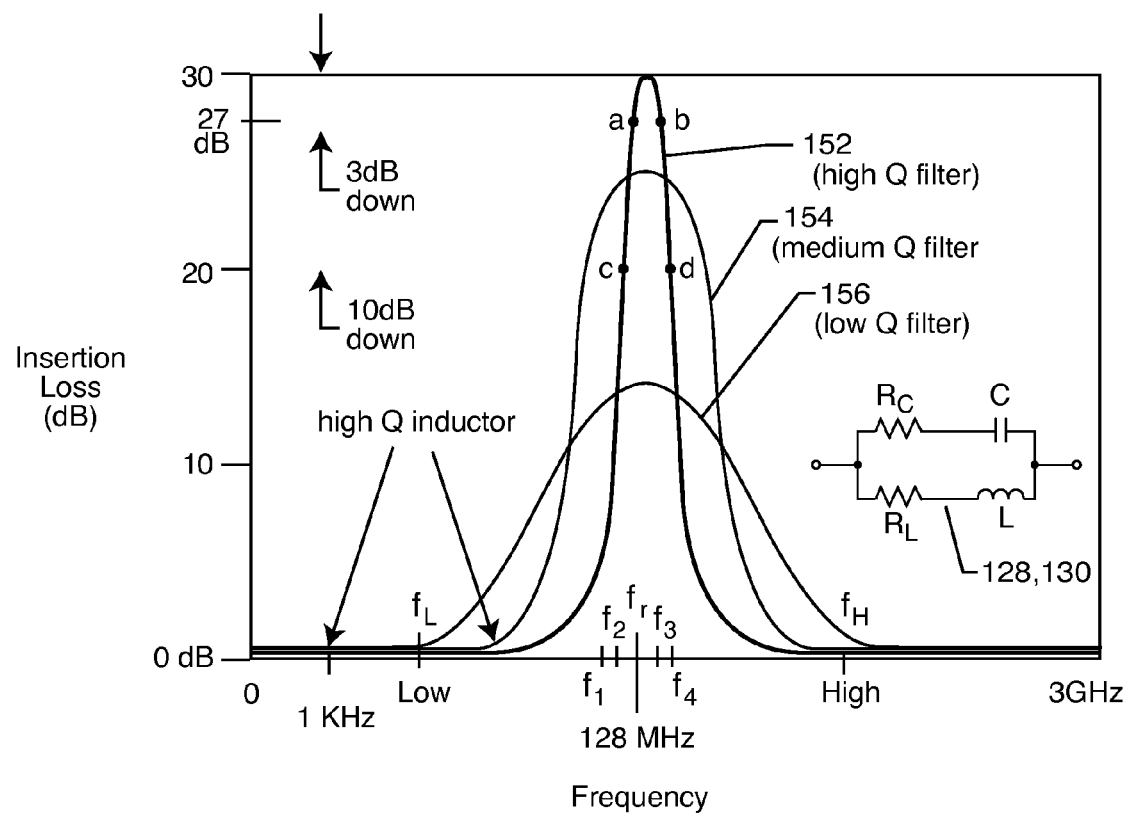
FIG. 18 is a graph of insertion loss verses frequency for bandstop filters having differing quality "Q" factors.

Referring now to FIG. 18, the efficiency of the bandstop filters (128, 130) are also measured in terms of a quality factor, Q. The bandstop filter circuit Q is typically expressed using the following equation:

$$Q = \frac{f_r}{\Delta f_{3dB}}$$

Where $f_r$ is the resonance frequency, and $\Delta f_{3\ dB}$ shown as points a and b in FIG. 18 is the 3 dB bandwidth of the bandstop filter. Bandwidth is typically taken as the difference between the two measured frequencies, $f_1$ and $f_2$, at the 3 dB down points as measured on an insertion loss curve, and the resonance center frequency is the average between $f_1$ and $f_2$. As can be seen in this relationship, higher Q values result in a narrower 3 dB bandwidth. The 3 dB bandwidth is $f_2-f_1$ measured in either kHz or MHz.

The 10 dB down points are shown as points "c" and "d" in FIG. 18 and correspond with frequencies $f_3$ and $f_4$. Accordingly, the 10 dB bandwidth is $f_4-f_3$ measured either in kHz or MHz. In general, the insertion loss curve can also be equated to an attenuation curve wherein the source and load impedances would be 50 ohms. In a preferred embodiment, the source impedance would be the source impedance of the lead and body tissue and the load impedance would be the input impedance of the AMD itself. Those experienced in the art will realize that the approach is equivalent.

Referring once again to FIG. 18, one can see the schematic for the bandstop filter 128, 130 including resistors $R_C$ and $R_L$. Resistor $R_C$ represents the equivalent series resistance of the capacitor C, or a discrete series resistor added in series with the capacitor. $R_L$ represents the equivalent series resistance of the inductor L, which is commonly due to the resistance of the wire turns or wire circuit traces of the inductor. As in the case with the capacitor, $R_L$ could also be a separate discrete chip resistor or other type of resistor added in series with the inductor portion of the bandstop filter 128, 130. Controlling the values of these resistances controls the 3 dB bandwidths and hence the quality factor Q of the bandstop filter.

Both the 3 dB bandwidth and the 10 dB bandwidth can be varied in accordance with the application. For example, if the application is for a very specific situation, for example a dedicated MRI guided catheter lab, then only one MRI scanner is involved. For example, if it is known that only a Siemens 1.5 Tesla MRI scanner of a particular model is to be used, then we can be confident of a very specific MRI RF pulsed frequency. The bandstop filter 128, 130 could be designed with relatively narrow 3 dB and the 10 dB bandwidths. In this case, the 10 dB bandwidth could be as small as 10 kHz. In this regard it should be borne in mind that the gradient field of the MRI scanner grades the main static field. A way to visualize this is with a patient lying in the supine position on the MRI scanner table. As the gradient field varies, the static magnetic field strength varies from head-to-toe of the patient. This means that the resonant frequency of the protons vary accordingly. In this way, the RF frequency varies thereby obtaining the image slice from the patient. About the narrowest variation is in the order of 10 kHz. On the other hand, if one were to design a bandstop filter 128, 130 for implanted lead application where two or three MRI scanners (from different manufacturers) needed to be compatible, then a 10 dB bandwidth of 100 kHz minimum would be desirable. In general, in a particularly preferred embodiment, the 10 dB bandwidth would be on the order of megahertz, or a minimum of 500 kHz. By having a 10 dB bandwidth on the order of MHz (0.5 MHz) minimum, one can then be sure that the bandstop filter 128, 130 would be effective over the range of commercially available or labeled 1.5 Tesla MRI scanners. Similar principles apply to 3 Tesla, 5 Tesla and other scanners that have a different static magnetic field strength. In these cases, the RF pulsed frequencies are much higher in frequency and their variation between different manufacturers and also their variation because of the gradient field can be even greater as measured in kHz.

Referring once again to FIG. 18, one can see that at very low frequencies, such as shown by $f_L$, it is important that the bandstop filter 128, 130 represent a very low impedance. This is because the bandstop filter must pass both pacing and biologic sensing signals with very little attenuation. The same is true of very high frequencies as shown by $f_H$ although in this case it would not matter if the bandstop filter offered additional attenuation since there are no biological signals in this range.

Accordingly, the "Q" or quality factor of the bandstop circuit 128, 130 is very important. As mentioned, it is desirable to have a very low loss circuit at low frequencies such that the biological signals not be undesirably attenuated. The quality factor Q not only determines the loss of the filter, but also affects its 3 dB and 10 dB bandwidths. If one does a plot of the filter response curve (Bode plot), the 3 dB and 10 dB bandwidths determine the attenuation curve, shape and how sharply the filter will rise and fall. With reference to curve 152 of FIG. 18, for a bandstop filter 128, 130 that is resonate at 64 MHz, an ideal response would be one that had infinite attenuation at 64 MHz, but had zero attenuation at low frequencies below 1 KHz. Obviously, this is not possible given the space limitations and the realities of the parasitic losses within components. In other words, it is not possible (other than at cryogenic temperatures) to build an inductor that has zero internal resistance. On the other hand, it is not possible to build a perfect (ideal) capacitor either. Capacitors have internal resistance known as equivalent series resistance and also have small amounts of inductance. Accordingly, the practical realization of a circuit, to accomplish the purposes of the present invention, is a challenging one. This is particularly true when one also considers that the bandstop circuit must also be miniature, highly reliable, and completely biocompatible.

The performance of the circuit is directly related to the efficiency of both the inductor L and the capacitor C; the less efficient each component is, the more heat loss that results, and this can be expressed by the addition of resistor elements, $R_C$ and $R_L$ to the ideal circuit diagram. The effect of lower Q in the bandstop circuit 128, 130 is to broaden the resonance peak about the resonance frequency. By deliberately using a low Q capacitor and/or inductor, one can broaden the resonance such that a moderately high impedance (attenuation) is presented at multiple MRI RF frequencies.

Referring again to FIG. 18, one can control both the 3 dB bandwidth and the 10 dB bandwidth by controlling the amount of resistance $R_C$ and $R_L$ in the bandpass filter circuit 128, 130. One must be careful not to let the resistance in series with the inductor be too large or biological frequencies will be attenuated. The reason for this is that at very low frequencies (below 1 kHz), the inductive reactance tends to be very low (approximate zero). At the same time, at very low frequencies the capacitive reactance tends to look infinite. Accordingly, for proper operation of delivering pacing pulses or sensing biological activity, the resistor value $R_C$ really does not matter much. Accordingly, a good way to control the Q of the bandstop filter 128, 130 is to establish resistance $R_L$ that is consistent with the parasitic resistances of inductor windings or turns and also carefully control the capacitor Q. Another reason that one must control the resistive loss $R_L$ of the inductor L is that if the resistance gets too high, excessive heating of the bandstop filter could occur. This is because there is a high frequency current that oscillates at the MRI pulsed frequency between the capacitor's C electric field and the inductor's L magnetic field. This circulating current can create heating about the bandstop filter in one of two ways: 1) by $I^2R$ heating in either resistance $R_L$ or $R_C$ (or both), or by eddy current losses in the hermetic or shield housing that surrounds the bandstop filter. Accordingly, a careful balance between component design and bandstop filter Q must be achieved.

The Lamour equation tells us that the frequency of the pulsed RF field is equal to the MRI constant times the static magnetic field strength of the clinical scanner in Teslas. This frequency is approximately 64 MHz for a typical prior art 1.5-Tesla hydrogen scanner. However, not all marketing labeled 1.5-Tesla scanners are the same. There is considerable variation in the static magnetic field strength from different manufacturers. This results in several hundreds of kilohertz or even a half megahertz of difference between the RF pulsed frequency between the various scanner manufacturers. Accordingly, the bandstop filter 128, 130 is designed to be resonant at a center frequency, $f_r$ representing the center of a range of RF pulsed frequencies. As shown in FIG. 18, a resistance element $R_C$, $R_L$ or both, is added in order to increase the 3 dB bandwidth of the L-C trap filter 128, 130. Referring once again to FIG. 18, one can see the attenuation curve for a high Q filter 152, a medium Q filter 154, and a low Q filter 156. The medium Q filter would work for many applications, but the attenuation of the low Q filter generally would not be adequate to be sure that excessive heating at a distal electrode would not occur. In the present invention, the desired curve shapes are 152 or 154. To put this in perspective, for an ideal bandstop filter (meaning that $R_C$ and $R_L$ are both zero), the filter response curve would look like a straight up and down line (not shown) centered above $f_r$. This would, of course, be so narrow that it would be both impractical to build (other than at cryogenic temperatures), and impractical for use over a range of MRI scanners. This resistance element can be a discrete resistor or it can be formed from the leads or circuit traces as a parasitic element that forms the inductance L itself. For simplicity, this resistance element is not shown in FIG. 16 and the subsequent drawings. However, it be understood that the bandstop filter is designed to attenuate over a range of MRI RF pulsed frequencies on the order of tens of kilohertz, hundreds of kilohertz, or even megahertz.

For medical implant applications it is very important that the implanted leads and their associated electrodes at the distal tips be very small. It is particularly important that the cross-sections or diameters of the bandstop filters be very small for easy endocardial insertion into the venous system of the human body. The present invention meets these criteria by using a novel combination of components that are mechanically mounted in series, but whose lumped elements are electrically in parallel. The components generally consist of commercial off-the-shelf miniature chip capacitor and inductor components. These are generally manufactured in high volume throughout the world. Accordingly, they are very inexpensive, but more importantly, they are very small in size. By way of example, twenty years ago a small sized monolithic chip capacitor (MLCC) would be 0603, meaning that it would be 0.060 inch long by 0.030 inch in width. In comparison, current inductor and capacitor chip components can be purchased as small as 0201 or 01005. This means that they are so small that they literally can fit through a pepper shaker. Human hands generally cannot assemble components this small. Accordingly, micro-robotic manufacturing is the preferred method of manufacturing the novel components assemblies of the present invention, wherein the components typically are delivered on tape and reel and fed into the robots which pick and place the components and then go through a series of steps including additional component placement, wave soldering, cleaning, automatic optical inspection and automated electrical testing. All of this is done in a linear robotic manufacturing operation that is completely or nearly free of human hands. In cardiac rhythm applications (pacemakers and ICDs), a desirable lead size is 6 French (0.079 inches in diameter). For deep brain stimulator applications, an even smaller size is desirable, such as 3 French, which is 1 millimeter in diameter or 0.039 inches. US 2007/0112398 A1 discloses a number of methods of manufacturing novel bandstop filters for placement in the lead systems of active implantable medical devices. The present invention extends these concepts further.

In mammalian implant applications, the shielded inductors, diverters, impeders, and bandstop filters of the present invention should be small and placed in series with the implanted lead or electrode of the medical device. In general, the diameter is much more important than the volume or length of the passive network package to be placed in series with an implanted lead 114, 114'. This is because leads are typically introduced into the human body either by tunneling or transvenous insertion. In such applications, it is necessary that the shielded lead component assembly be EMI shielded, biocompatible and highly reliable. Although commercial off-the-shelf capacitor and inductor components are very small in size, arranging them such that they are electrically coupled in parallel can increase the size of the bandstop filter where complications can arise in the placement and use of the implanted lead or electrode.

Commercial off-the-shelf capacitor and inductor components are typically not entirely comprised of biocompatible materials. However, in accordance with the present invention, the shielded inductor L and capacitor C elements can be constructed to be completely biocompatible. In this case it would be not necessary to place them in a biocompatible hermetic container, just an open ended EMI shield would suffice. This would have great advantages in further reducing both size and cost. In this regard, US 2009/0116167, U.S. Pat. No. 7,535,693, and US 2009/0259265, are incorporated by reference.

Figure 19:
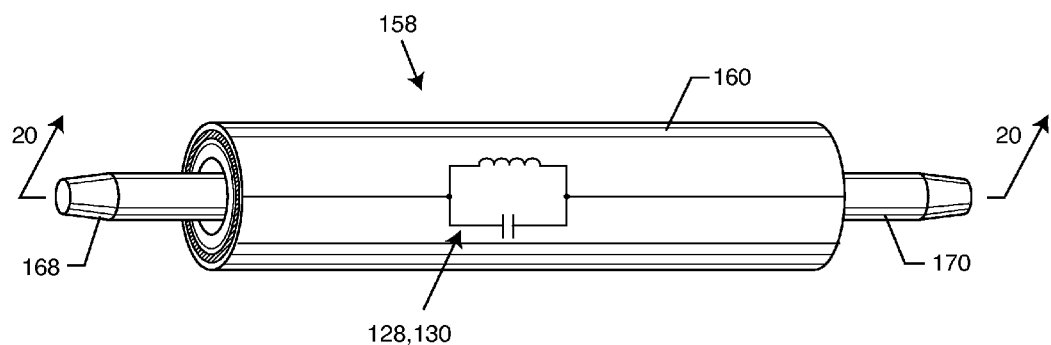
FIG. 19 illustrates a hermetically sealed container or a bandstop filter embodying the present invention.

With reference to FIG. 19, it is a feature of the present invention that custom or "off-the-shelf" non-biocompatible miniature inductor L and capacitor C components are mechanically installed in shielded (conductive) hermetic packages or containers 158 in series, but have electrical circuit traces that couple the lumped inductor and capacitor elements electronically in parallel, thereby forming bandstop filters 128, 130 as described above. FIG. 19 illustrates a hermetically sealed shielded container 158 having the inductor (L) and capacitor (C) components installed therein in series with one another, but whose lumped L and C elements are coupled electronically in parallel, so as to form one or more bandstop filters 128, 130. The shielded housing 160 for the hermetically sealed container 158 is very small in diameter or cross-section and can be disposed between portions of an implantable lead 114, within an electrode assembly, etc.

Figure 20:
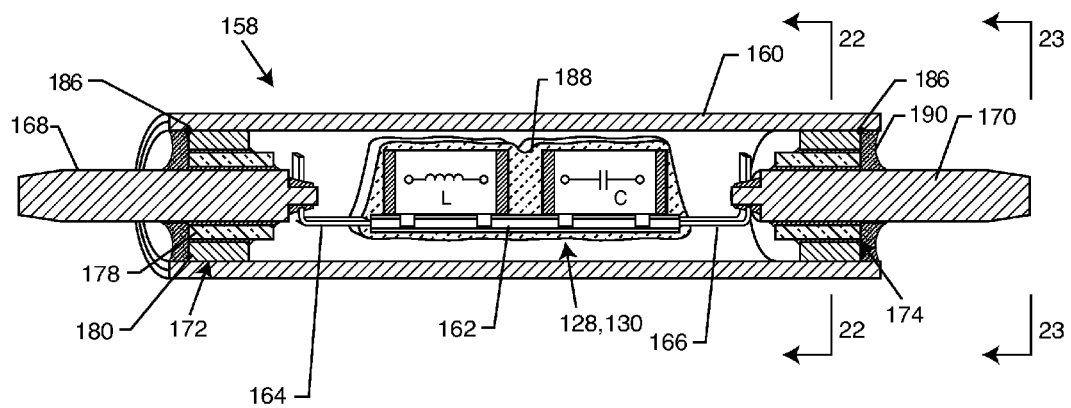
FIG. 20 is an enlarged sectional view taken generally along line 20-20 from FIG. 19.

FIG. 20 is a cross-sectional view taken generally along line 20-20 of FIG. 19 and shows the various component parts of the shielded hermetically sealed container 158. The shielded housing 160 can be comprised of a biocompatible metal or alloy, such as titanium, platinum, platinum-iridium, gold, palladium, tantalum, carbon, niobium, etc., or alloys thereof. The shielded housing 160 can also be a non-metallic material, such as sapphire, ruby, lumina, ceramic, glass, etc, having a thin layer of conductive metal deposited on either its inside or outside surface. For example, if the non-metallic shield was cylindrical, a metal coating could be applied to its outside diameter. In this case, the metal coating should be biocompatible and could be applied by electroplating, sputtering, chemical vapor deposition, cladding, or the like. The inductor L and the capacitor C are disposed on a substrate 162 and physically arranged in series, or end-to-end with one another, yet conductively or electronically coupled to one another in parallel. Circuit traces 164 and 166 are conductively coupled to the inductor L and capacitor C of the bandstop filter 128, 130 and extend to conductive terminals 168 and 170 of hermetic seal assemblies 172 and 174. The conductive terminals 168 and 170 are designed to be conductively coupled to portions of the implantable lead 114, 114' or electrode assembly.

Figure 21:
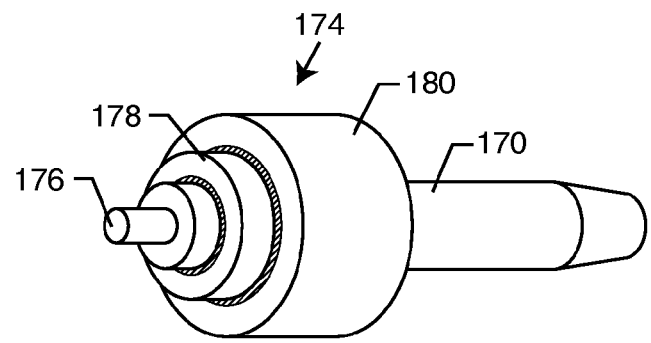
FIG. 21 is an enlarged perspective view of the hermetic seal assembly from FIG. 20.

FIG. 21 is an enlarged perspective view of the hermetic seal assembly 174 from FIG. 20, having the terminal 170 extending therethrough to a crimp, solder joint or laser weld tip 176. The electrical connection to the tip 176 could also be formed by thermal-setting conductive adhesives. The terminal 170 is attached to an insulator 178, which is in turn attached to an outer ferrule 180.

Figure 22:
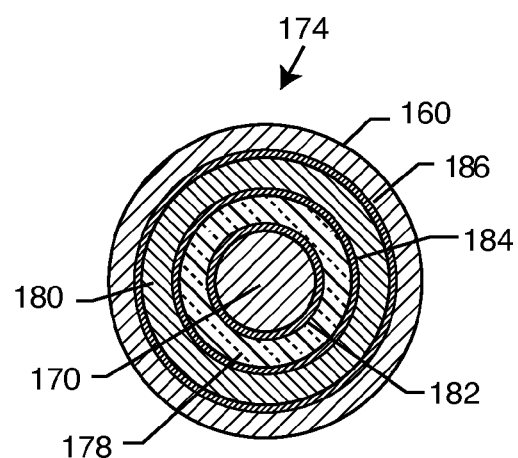
FIG. 22 is an enlarged cross-sectional view taken generally along the line 22-22 from FIG. 20.

FIG. 22 is a cross-section drawing taken along line 22-22 from FIG. 20. The terminal 170 is preferably of a common platinum-iridium alloy, such as 9010 or 8020. However, any biocompatible and suitable material could be used in place of platinum-iridium. Gold braze 182 forms a hermetic seal between terminal 170 and insulator 178. The insulator 178 may be a polished sapphire, ruby, polycrystalline alumina, or even glass or a general ceramic material. Sputtering would first be deposited on the surfaces so that the gold braze 182 will readily adhere and wet. Gold braze 184 forms a hermetic seal between insulator 178 and the ferrule 180. Gold brazes 182 and 184 are generally pure gold brazes for biocompatibility and long term reliability. The surface preparation process for the ceramic insulator 178 can be as follows: C—Axis single crystal, polycrystalline alumina (Al2O3), Zirconia Stabilized Alumina and/or Yttria. Tetragonal Zirconia Polycrystalline YTZP is etched using RF plasma before PVD sputtering using a biologically compatible metallic system. Plasma cleaning removes organic surface contamination and hydroxyl/oxides resulting in a higher energy surface. This activated surface readily forms strong covalent bonds with metallization atoms promoting robust, hermetic adhesion. Through industry standard process refinements, the resulting low stress, dense coating does not spall off or blister and improves the function and reliability of the final brazed joint. The outer ferrule 180 is also, preferably, of platinum-iridium since its very easy to laser weld. It is also radio-opaque.

In the preferred embodiment, the insulator 178 would be a polished sapphire. It would then go through a plasma-etch process, such as a 500 watt plasma-etch, to increase its surface roughness. Titanium-molybdenum or niobium metallization would be a preferred sputter material for adhesion and wetting of the associated gold braze pre-forms.

Figure 23:
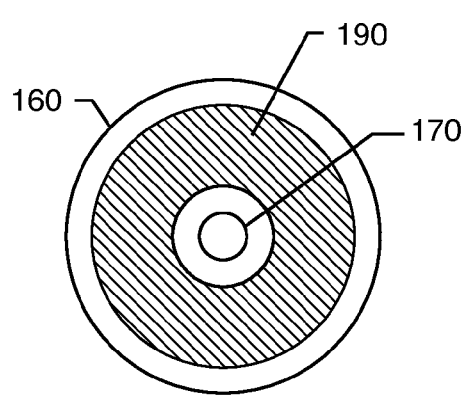
FIG. 23 is an end view of the hermetic seal assembly of FIG. 21, taken from line 23-23 in FIG. 20.

In FIGS. 20 and 21, one can see that the interior tip 176 of the terminals 168 and 170 has been extruded to be fitted into an aperture, socket, etc, of the conductive substrate or circuit traces 164 and 166. Alternatively, the interior tip 176 may have an aperture therethrough so that a crimped connection can be formed between it and the conductive substrate or circuit traces 164 and 166, and subsequently laser welded. The method of attachment to the interior tip 176 will vary in accordance with the type of attachment desired to the internal circuitry of the bandstop filter 128, 130. In any event, the conductive terminals 168 and 170 are conductively coupled to the bandstop filter 128, 130 as the associated hermetic seal assemblies 172 and 174 are slid into place and hermetically sealed by laser welding 186 to the housing 160 of the container 158. FIG. 23 is an end view taken along line 23-23 in FIG. 20.

Again, FIG. 20 shows the bandstop filter 128 and 130 comprised of the inductor L and capacitor C, and the flexible circuit substrates 164 and 166 extending therefrom, attached to the terminals 168 and 170 so as to place the terminals 168 and 170 in electrical series with one another. However, the inductor L and the capacitor C, although placed end-to-end and physically in series with one another, are conductively coupled electrically with one another in parallel. An insulating material 188, such as a thermal-setting non-conductive polymer, at least partially fills the remainder of the EMI shield housing 160 to provide protection and mechanical robustness to the overall container assembly 158. This structure lends itself to a novel "ship-in-the-bottle" method of manufacturing. That is, all of the elements contained within the shield housing 160 are pre-assembled outside the housing. In particular, the terminal 168, the substrate 162 containing the inductor L and capacitor C, and the opposite terminal 170 and the associated hermetic seals 172 and 174, are all pre-assembled outside of the overall EMI shield housing 160. This facilitates proper electrical connections and electrical testing of the pre-assembly. In addition, this entire subassembly can go through high reliability screening. Typically, this would consist of thermal cycling or thermal shock followed by a burn-in, which means applying a relatively high voltage at elevated temperature to the circuit components and then comprehensive electrical test afterwards. Once all of this has been done, this entire pre-assembly is slipped inside the overall cylindrical EMI shield housing 160 and then a final laser weld 186 is formed.

FIG. 20 also shows an optional conformal coating 190 which is provided over the two gold brazes 182 and 184. This conformal coating 190 could also be applied to the entire outer surface of the housing 160 and a portion of terminals 168 and 170, as well as optionally over the electrical attachments to the lead system. This conformal coating 190 is important to provide electrical isolation between the two terminals 168 and 170. When directly exposed to body fluids (which contain electrolytes), gold can migrate in the presence of a voltage bias. It has been shown that pacemaker pacing pulses in saline solution can actually cause a gold electro-migration or electroplating action. The concern is that the gold braze materials 182 and/or 184, under voltage or pulse bias, may over time migrate or deposit (electro-plate) onto another surface such as the terminal 170 or the housing 160, which could negatively affect the long-term hermeticity and reliability of the hermetic seal assembly 174. Accordingly, the conformal coating or backfill 190 is placed as shown to cover both of the gold brazes 182 and 184. The conformal coating 190 may comprise thermal-setting non-conductive adhesives, silicones, parylene (which is vapor deposited), and the like, including epoxies, polyimides, polyethylene oxide, polyurethane, silicone, polyesters, polycarbonate, polyethylene, polyvinyl chloride, polypropylene, methylacrylate, para-xylylene, and polypyrrhol. In particular, Epo-tek H81 is considered a preferred epoxy which has already been tested for long-term biocompatibility. The importance of providing electrical isolation across components, such as bandstop filters, is more thoroughly described in US 2010/0324640 which is incorporated herein by reference.

A complete conformal coating 190 over the entire shield housing 160 may be desirable to provide electrical isolation between the conductive terminal pins 168 and 170. This provides critical performance capability in the event of complete saturation of the housing 160 in saline or biological fluid. Additional performance benefits for a conformal coating 190 include lubricity, radiopacity, and wear resistance.

Figure 24:
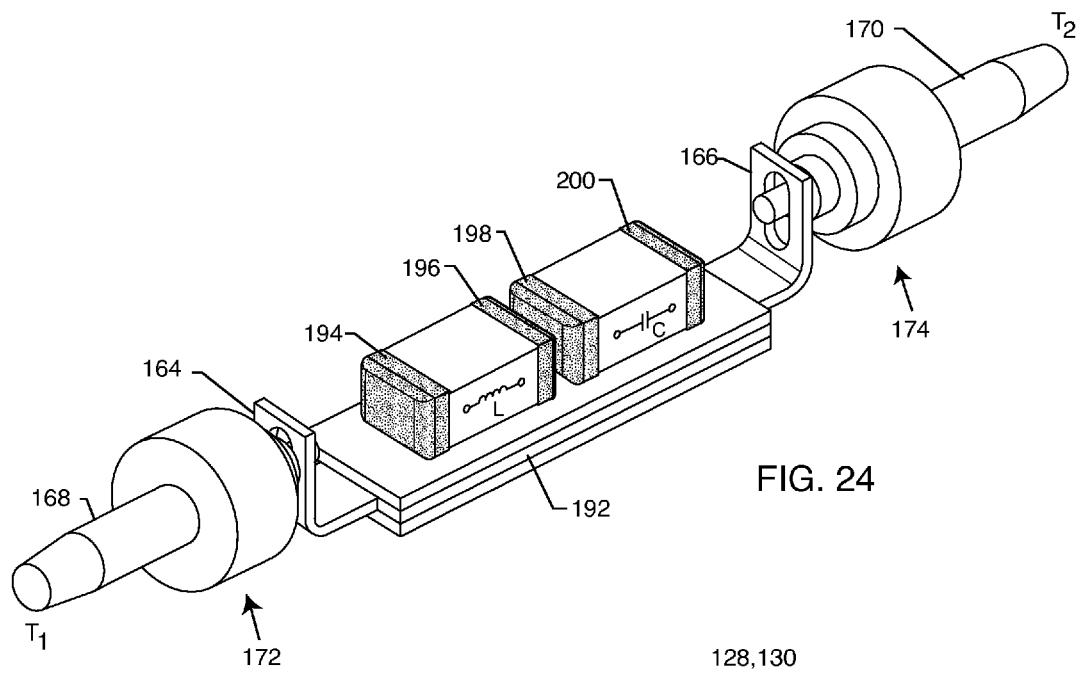
FIG. 24 is a perspective view illustrating a multi-layer rigid substrate or flex cable onto which the inductor and capacitor of FIG. 20 are mounted.
Figure 25:
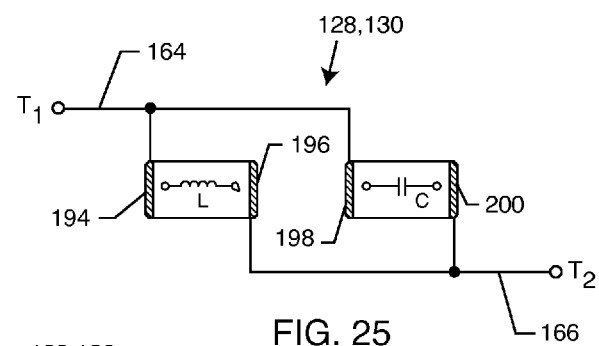
FIG. 25 is a schematic illustration showing that the inductor and capacitor are physically disposed in series relative to one another and yet electrically connected in parallel.
Figure 26:
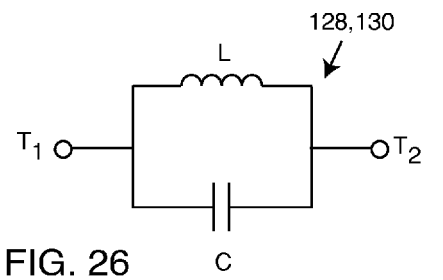
FIG. 26 is an electrical schematic diagram of the bandstop filter of FIGS. 24 and 25.

FIG. 24 illustrates a multi-layer substrate or flex cable 192 onto which the inductor L and capacitor C are mounted. The inductor L is a chip inductor having first and second conductive termination surfaces 194 and 196 which are spaced from one another in non-conductive relation. The capacitor C also has first and second conductive termination surfaces 198 and 200 which are spaced apart from one another in non-conductive relation. The chip inductor L can be any number of chip inductor types, however the present invention is also not limited to chip inductors only. The inductor L could also be a solenoid inductor, a toroidal inductor, or any type of inductor that is known in the prior art. Moreover, the chip capacitor C can be any number of chip capacitor types, but the present invention is not limited to chip capacitors only. The capacitor C ray be of many different types of capacitor technologies, including film capacitors, tantalum capacitors, monolithic ceramic capacitors, electrolytic capacitors, feedthrough-type capacitors, or even tubular capacitors. FIGS. 24 and 25 show that the inductor L and the capacitor C are physically disposed in series relative to one another, such that they are generally aligned with one another along a common longitudinal axis and placed end-to-end. However, as shown in FIGS. 25 and 26, the inductor L and the capacitor C are conductively or electrically coupled to one another in parallel. FIG. 26 is an electrical schematic diagram of the bandstop filter 128, 130 of FIGS. 24 and 25. For a more complete description of how to dispose implantable lead components physically in series but electrically in parallel, reference is made to US 2010/0100164 A1, the contents of which are incorporated herein.

Figure 27:
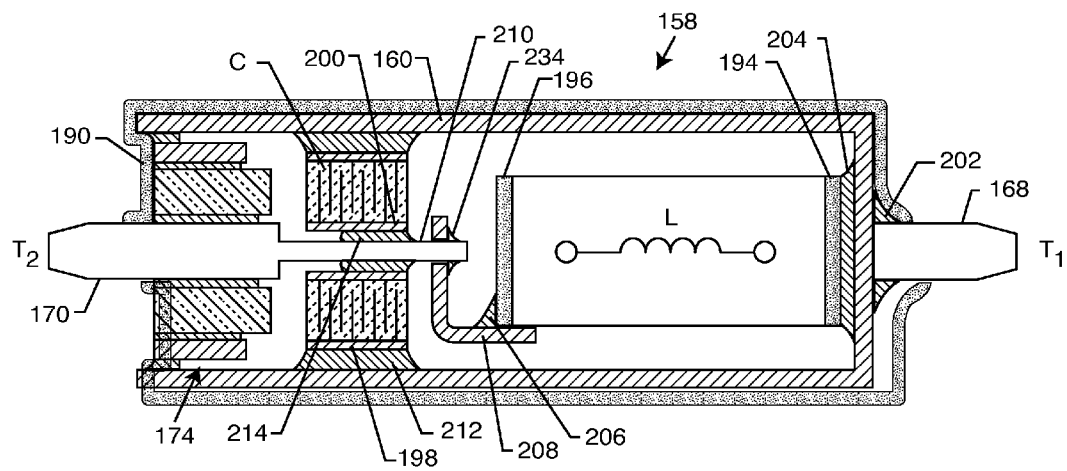
FIG. 27 is a sectional view similar to FIG. 20, but illustrating an alternative embodiment where the chip capacitor has been replaced with a feedthrough capacitor.
Figure 28:
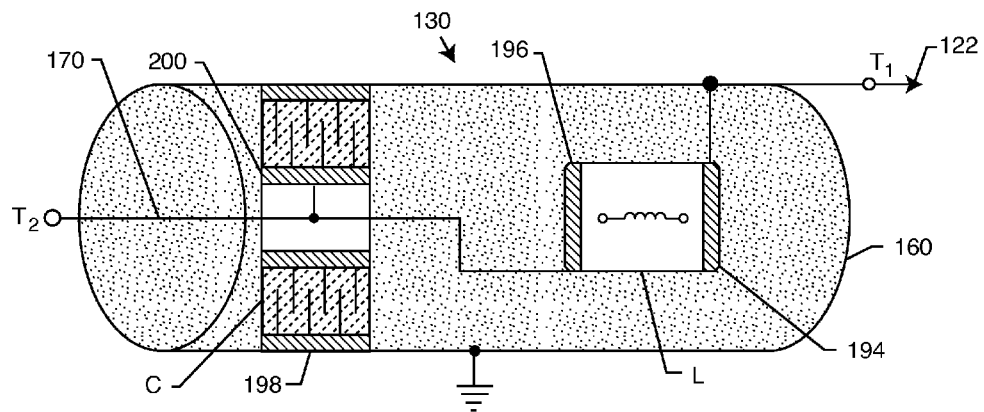
FIG. 28 is a schematic illustration of FIG. 27, showing electrical connections of the inductor and capacitor relative to the lead.
Figure 29:
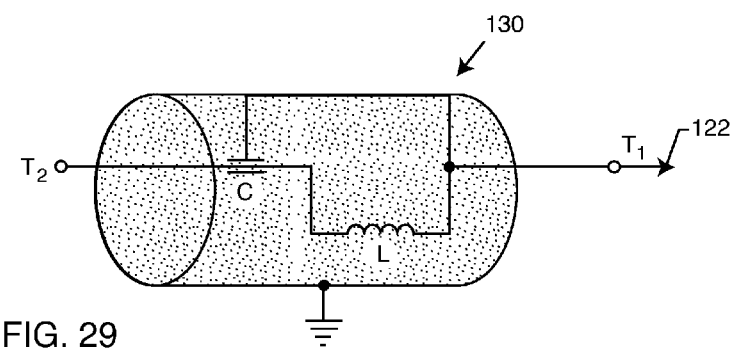
FIG. 29 is an electrical schematic diagram of the structure shown in FIGS. 27 and 28.

FIGS. 27-29 illustrate a configuration where a chip inductor L is physically disposed in series with a feedthrough capacitor C, and yet is electrically connected in parallel to form a bandstop filter 130. The chip inductor L and the feedthrough capacitor C are disposed within an EMI shielded hermetic container 158 comprising a conductive housing 160 of a biocompatible material which includes one open end, and a hermetic seal assembly 174 disposed within the open end of the housing 160. The conductive terminal 168 is conductively coupled to the housing 160 by a laser weld 202. The first conductive termination surface 194 of the inductor L is conductively coupled to the housing 160 by means of a solder, braze, or conductive adhesive 204 or the like. The second conductive termination surface 196 of the inductor L is similarly conductively coupled by means of a solder, braze, or conductive adhesive 206 or the like, to a conductive bracket 208 which is also conductively coupled to an extension 210 of the conductive terminal 170 which extends through a central passageway of the feedthrough capacitor C. The first conductive termination surface 198 of the capacitor C is conductively coupled to the housing 160 by means of conductive adhesive 212 or the like, and the second conductive termination surface 200 of the feedthrough capacitor C is conductively coupled to the extension 210 of the conductive terminal 170 by means of conductive adhesive 214 or the like. The hermetic seal assembly 174 disposed within the opening to the housing 160, and which prevents direct contact between body fluids and the inductor L, the capacitor C and related electrical components, is essentially the same as the hermetic seal assembly 174 illustrated in FIGS. 20-23. The illustrated structure advantageously eliminates one hermetic seal assembly in comparison with previously illustrated embodiments, by providing a terminal 168 which is shorted to the conductive EMI shield housing 160. As shown, the optional conformal coating 190 is applied over the entire outer surface of the housing 160 as well as a portion of the terminals 168 and 170. This conformal coating 190 advantageously provides additional electrical isolation between the two terminals 168 and 170.

Figure 30:
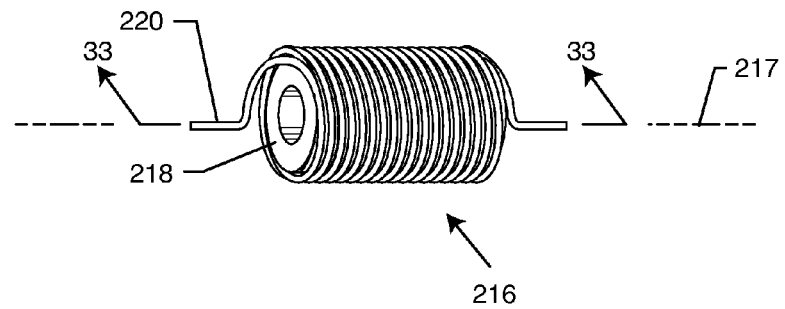
FIG. 30 is a perspective view of a solenoid inductor wrapped around a non-ferromagnetic core.

FIG. 30 illustrates a solenoid inductor 216 wrapped around a non-ferromagnetic core 218. The term solenoid inductor as defined herein includes any inductor geometry whose magnetic fields 219 are aligned generally along the central axis of the lead and/or the shield 126.

The solenoid inductor 216 comprises, in accordance with the present invention, an inductive component having a primary magnetic field line axis designated by the reference number 217.

Figure 31:
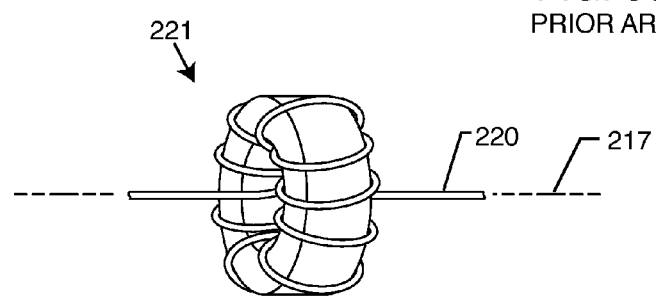
FIG. 31 is a perspective view similar to FIG. 30, illustrating a toroidal inductor.

FIG. 31 is a perspective view similar to FIG. 30, illustrating a toroidal inductor 221. As was the case with the solenoid inductor 216, the toroidal inductor 221 has a primary magnetic field line axis 217. The inductors 216 and 221 consist of coils of wire 220 which can be single or multi-layer.

Figure 32:
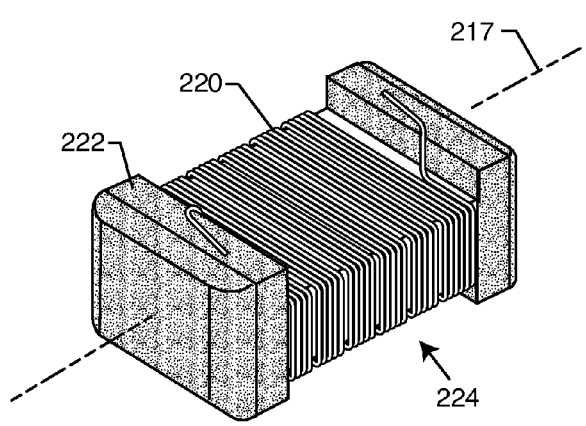
FIG. 32 is similar to FIG. 30, showing inductor wires coiled around a plastic support structure to form the equivalent of an air-wound inductor.
Figure 33:
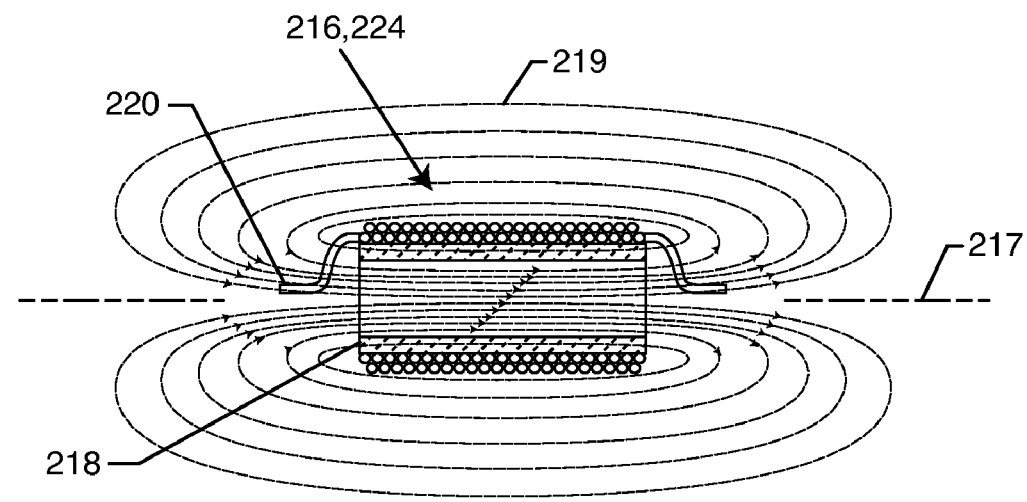
FIG. 33 is a sectional view taken along the line 33-33 from FIG. 30, illustrating the magnetic field when no shield is present.

The inductors 216 and 221 may be wound on a magnetic material such as a ferrite core, however, this is highly undesirable for MRI applications. This is because the MRI main static field would tend to saturate such high permittivity (k) ferrite materials. Accordingly, the shielded inductors of the present invention are generally comprised of air or non-ferromagnetic materials as shown in FIG. 32, where the inductor wires 220 are coiled around a support structure 222 of a non-magnetic material, such as a ceramic or plastic. This makes the coil 224 of FIG. 32 equivalent to an "air-wound" inductor having a primary magnetic field line axis 217. These so-called air coils are not very volumetrically efficient and tend to have a magnetic field 219 as illustrated in FIG. 33. This is well known in physics and for a DC case, would generate a north and south pole. In an AC case, which is the case for an MRI RF application, these field lines would be alternating at the RF frequency of the MRI RE pulsed field. These field lines 219 would therefore build up and collapse which also reverses the induced currents again at the frequency of the RF pulsed field. The inventors have determined that the field lines 219 of the solenoid inductors 216, 224 are affected when the inductor is placed inside of a conductive shield 126. As previously described in connection with FIGS. 20 and 27, this conductive shield 126 can also be the housing 160 of a hermetically sealed container.

Figure 34:
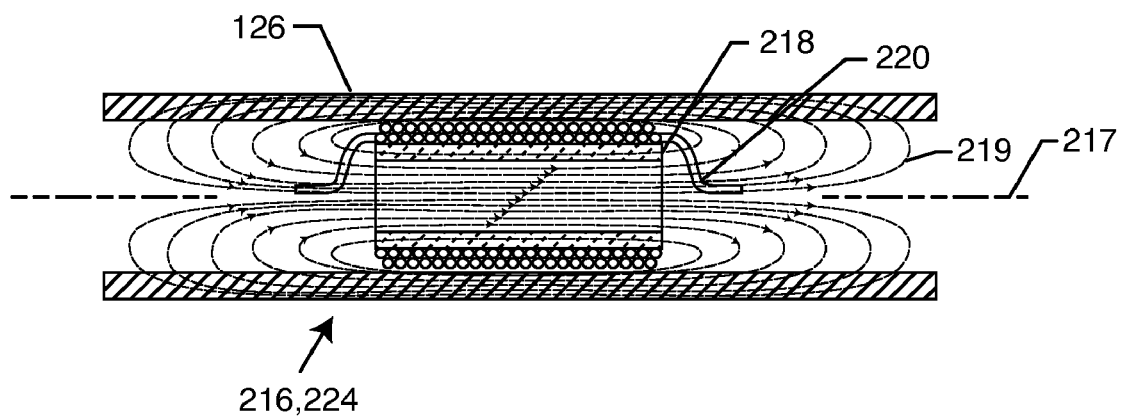
FIG. 34 is similar to FIG. 33, illustrating changes in the magnetic field when the inductor is shielded.

As one can see in FIG. 34, when the solenoid inductor 216, 224 is placed within a conductive shield 126, the magnetic field lines 219 of the solenoid inductor coil 220 tend to capture and induce currents in the shield 126 which affects the energy stored in the coil's magnetic field, and therefore the inductance value of the inductor 216, 224. FIG. 33 illustrates a worst case for a solenoid coil's magnetic fields 219 wherein the shield 126 has a very high permeability. The high permeability of the shield 126 creates a low reluctance path for the magnetic fields 219 which tends to capture some amount of the coil's magnetic field 219 in the shield 126. The amount of flux captured by the shield 126 is directly related to the material's permeability; as the permeability increases, more magnetic field lines 219 tend to be captured within the shield. In a preferred embodiment, the shield 126 is of a biocompatible material such as platinum-iridium alloy which has a relatively low permeability. Accordingly, for a shield 126 of platinum-Iridium (or equivalent biocompatible metals such as titanium, stainless steel, niobium), the magnetic field lines 219 do not completely collapse into the shield walls as shown in FIG. 34, but rather the field lines 219 penetrate and propagate outside the shield 126. For both high permeability and lower permeability shields 126, the value of the solenoid coil inductance in nanoHenries or microHenries is shifted when one measures this value with the inductor coil 220 outside of the shield 126 (in air) as opposed to inserting the inductor coil 220 into the shield 126. When the inductor 216, 224 is a component of an L-C bandstop filter 128, 130, it is very critical that this change in inductance be accounted for in the design. If it is not properly accounted for, the resulting resonant frequency of the L-C bandstop filter 128, 130 may not be centered on an MRI band of RF pulsed frequencies.

FIGS. 35-37 illustrate a wire wound-type inductor 223. The wire wound inductor 223 is similar to the inductor 224 of FIG. 32, and includes inductor wires 220 which are coiled around a support structure 222 of a non-magnetic material, such as a ceramic or plastic. This assembly has been mounted in a carrier 225, and has a primary magnetic field line axis 217 as shown.

FIG. 36 illustrates the general configuration of the magnetic field 219 surrounding the unshielded wire wound inductor 223, similar to that shown in FIG. 33. In contrast, when the inductor 223 is placed within a conductive shield 126 as shown in FIG. 37, the magnetic field lines 219 of the inductor 223 tend to capture and induce currents in the shield 126 which affects the energy stored in the coiled inductor's field, and therefore the inductance value of the inductor 223. In contrast with the arrangement shown in FIG. 34, the inductor 223 in FIG. 37 has been disposed within the conductive shield 126 such that the inductor's magnetic field line axis 217 is oriented substantially orthogonally to the primary longitudinal axis 227 of the conductive shield which minimizes shield eddy currents and energy losses, all in accordance with the present invention.

Figure 38:
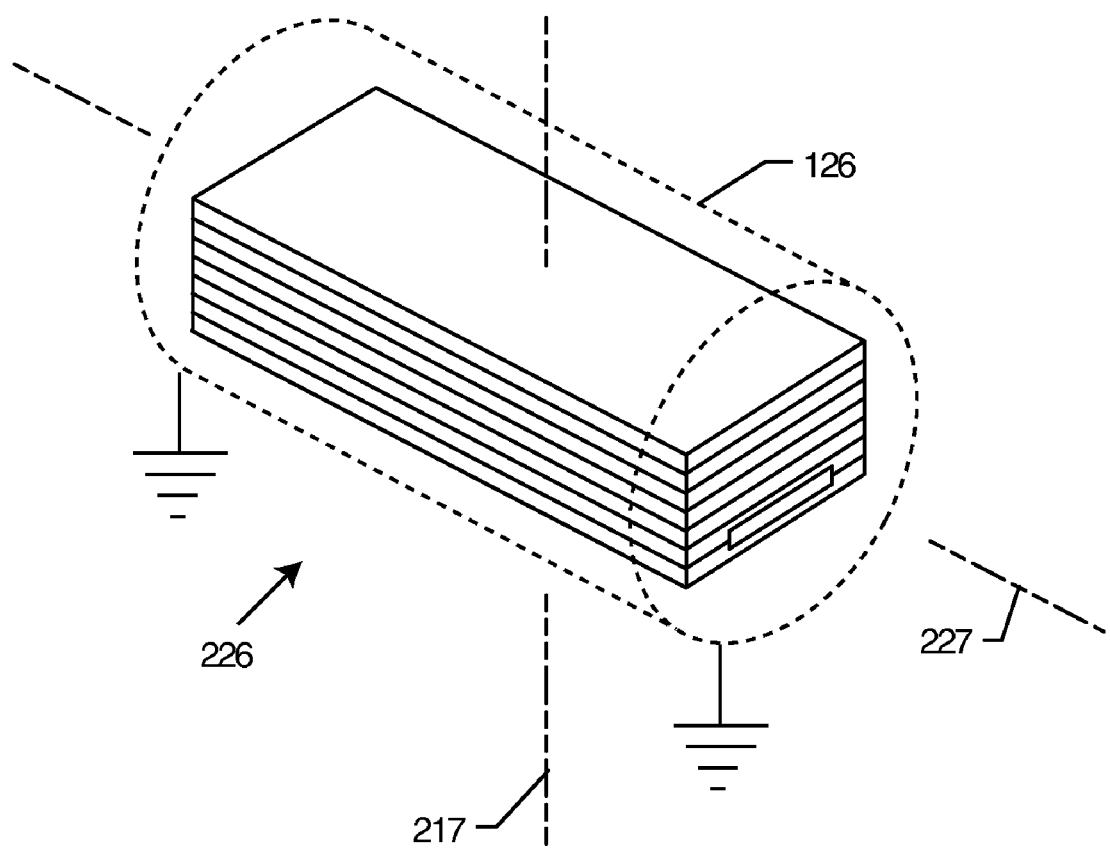
FIG. 38 illustrates a thick film inductor.

FIG. 38 illustrates a prior art thick film or chip inductor 226 taken from U.S. Pat. No. 5,970,604, the contents of which are incorporated by reference. As defined herein, the term "chip inductor" includes any inductor winding or circuit trace geometry whose magnetic fields are generally aligned at 90 degrees to the length or layers of the inductor. Such chip or thick film inductors 226 may be utilized in connection with the present invention, either alone or in connection with a parallel capacitor C to form a bandstop filter 128, 130.

Figure 39:
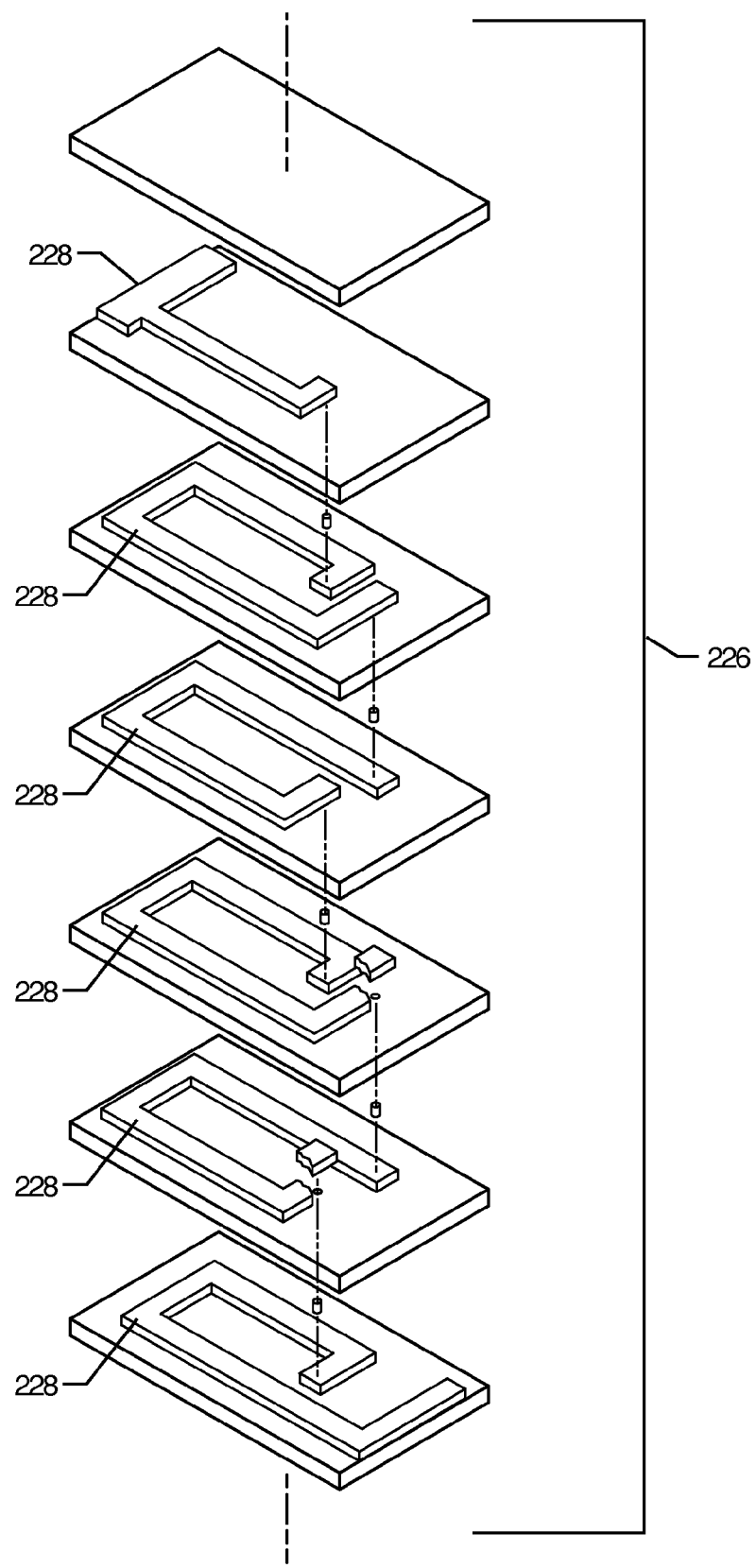
FIG. 39 shows the arrangement of circuit traces that form the thick film inductor of FIG. 38.

FIG. 39 shows an exemplary arrangement of circuit traces 228 that form the thick film inductor 226. The electromagnetic field lines of such an inductor are generally opposite orthogonally to those for the solenoid inductors of FIGS. 30, 33 and 36. Referring back to FIG. 38, one will note that the thick film inductor 226 is disposed within a conductive shield 126 so that the longitudinal axis of the inductor is lined with the primary longitudinal axis 227 of the shield. However, in accordance with the present invention, the primary magnetic field line axis 217 is oriented substantially orthogonally to the longitudinal axis of the shield 126.

Figure 40:
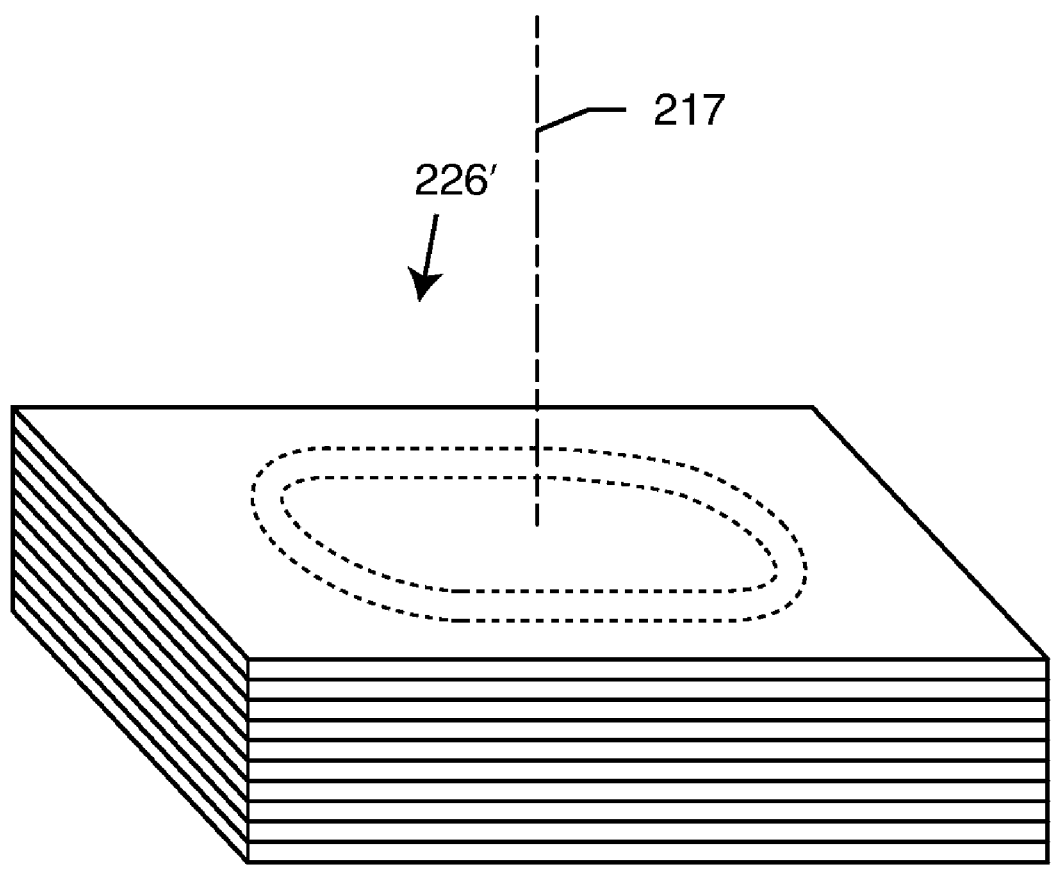
FIG. 40 is a perspective view of an exemplary thick film inductor.
Figure 41:
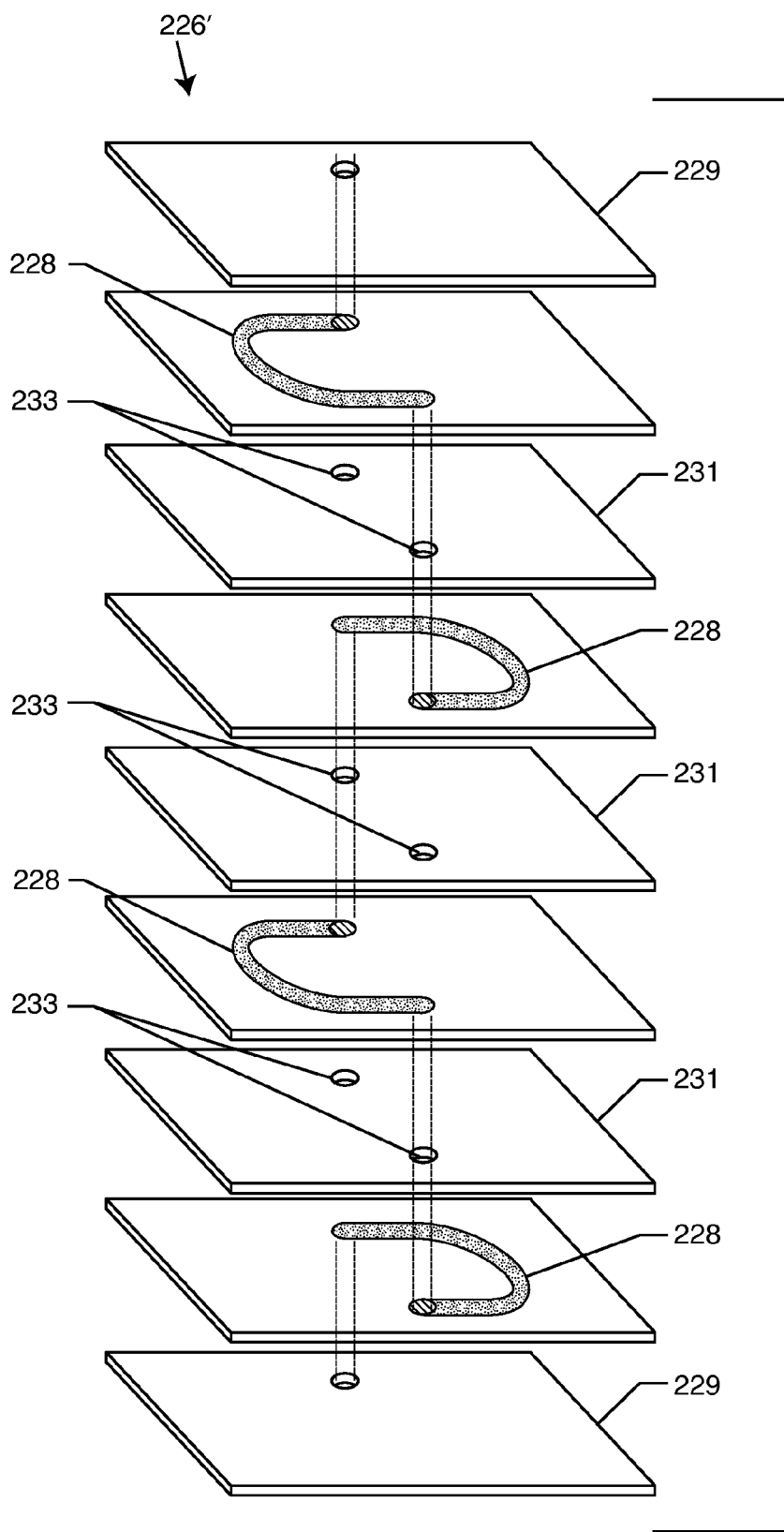
FIG. 41 is an exploded view of the structure of FIG. 40.

FIG. 40 is a perspective view of another thick film inductor 226' similar to that shown in FIG. 38. The individual films are shown in an assembled state where it resembles a rectangular box. FIG. 41 is an exploded view of the thick film inductor 226' where each individual film has been exploded to better see the construction of the inductor 226'. The end sheets 229 capture the whole assembly where the coil circuit traces 222 are sandwiched between the mid sheets 231 that have holes 233 to allow each coil 228 to be connected to the adjacent half coil 228 so that the assembly creates n×0.5 closed loops, where n is an integer. When assembled and mounted upon a substrate, the thick film type inductor 226' has the axis of the coils' 228 orientation normal to the chip mounting axis. Depending on the desired performance or attributes of the inductor, the size of the coils 228, thickness of the coils 228, and the number of coils 228 can all be varied accordingly.

Figure 42:
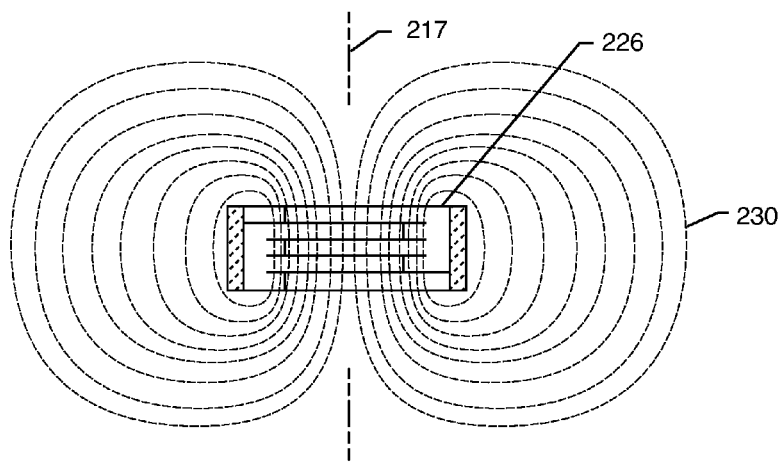
FIG. 42 is similar to FIG. 33, illustrating electromagnetic field lines for the thick film inductor when not shielded.

FIG. 42 illustrates the ideal (in air) electromagnetic fields 230 around the thick film inductor 226' of FIGS. 40 and 41. In this case, the magnetic fields 230 are directed at 90 degrees to the direction of the implanted lead center line. When this type of thick film inductor 226 is inserted into a shielded housing 126, the field lines will induce currents into the surrounding conductive shield as shown in FIGS. 43 and 44.

Figure 43:
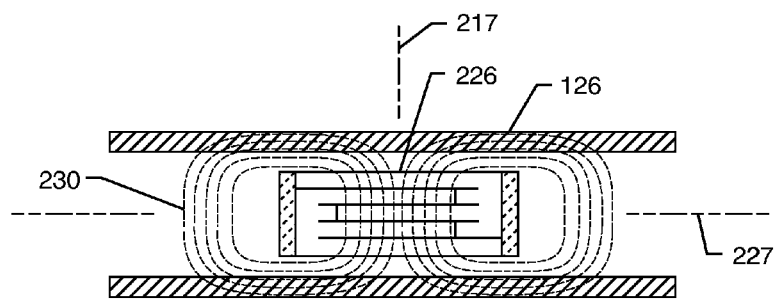
FIG. 43 is similar to FIG. 34, illustrating changes in the magnetic field lines when the thick film inductor is shielded.
Figure 44:
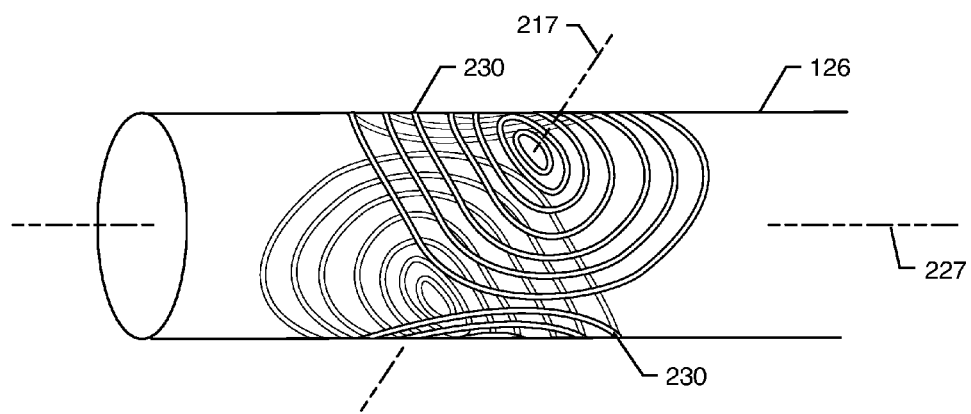
FIG. 44 illustrates distribution of current induction for a thick film inductor when shielded.

FIGS. 43 and 44 illustrate how the magnetic fields 230 of the chip inductors 226 and 226' of FIGS. 38-41 tend to be captured and induce currents into the shield walls 126 which affects the energy stored in the coil's magnetic field and the coil inductance value. FIG. 43 is a worst case for a chip inductor's magnetic fields 230 wherein the shield 126 has a very high permeability. The high permeability of the conductive shield creates a low reluctance path for the magnetic fields 230 of the inductors 226 and 226' which tends to capture a great deal of the coil's magnetic field 230 in the shield walls 126. FIG. 44 comes from electromagnetic field modeling and shows the magnetic field pattern 230 of the chip inductor 226' which is orthogonal to both the central axis 227 of the shield 126 and the lead central axis. In a preferred embodiment, the shield 126 is of a biocompatible material such as platinum-iridium alloy which has a relatively low permeability. Accordingly, for a shield 126 of platinum-Iridium material (or equivalent biocompatible metals such as titanium, stainless steel, niobium), the magnetic field lines 230 do not completely collapse into the shield walls 126 as shown in FIG. 43, but rather the field lines 230 penetrate and propagate outside the shield 126. For a chip inductor 226, 226' inserted inside of either a high permeability or lower permeability shield 126, the value of the inductance in nanoHenries or microHenries is different if one measures this value with the inductor outside of the shield 126 (in air) as opposed to inserting the inductor into the shield. This shift is less than that for a solenoid inductor 216, 224, but is still significant. Still, when the chip inductor 226, 226' is a component of an L-C bandstop filter 128, 130, it is very critical that this change in inductance be accounted for in the design. If it is not properly accounted for, the resulting resonant frequency of the L-C bandstop filter 128, 130 may not be centered on an MRI band of RE pulsed frequencies which would make it ineffective.

In general, the amount of induced current from the magnetic field 230 of a chip inductor 226, 226' in the conductive shield 126 encompasses less area and less magnitude as compared to the solenoid inductors 216, 224 of FIGS. 32-34. In other words, there is less energy loss and inductive shift from a chip inductor geometry as compared to a typical solenoid inductor type of arrangement. In accordance with the present invention, the inductive component's magnetic field line axis 217 is already oriented substantially orthogonally (70°-110°) to the primary longitudinal axis 227 of the conductive shield or housing 126.

Figure 45:
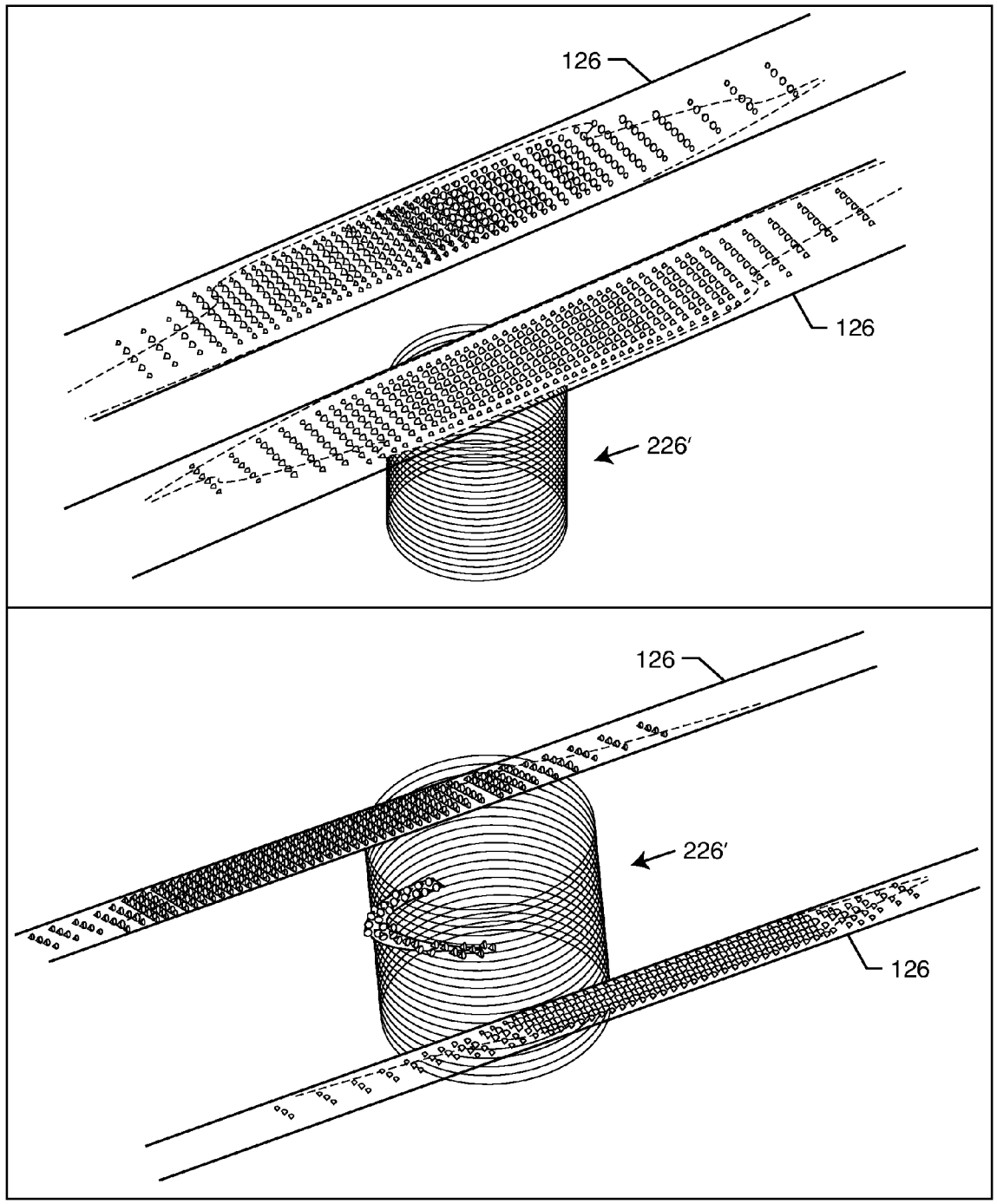
FIG. 45 is a perspective view of the modeling of current flow in an outer conductive shield or housing by a thick film type inductor.
Figure 46:
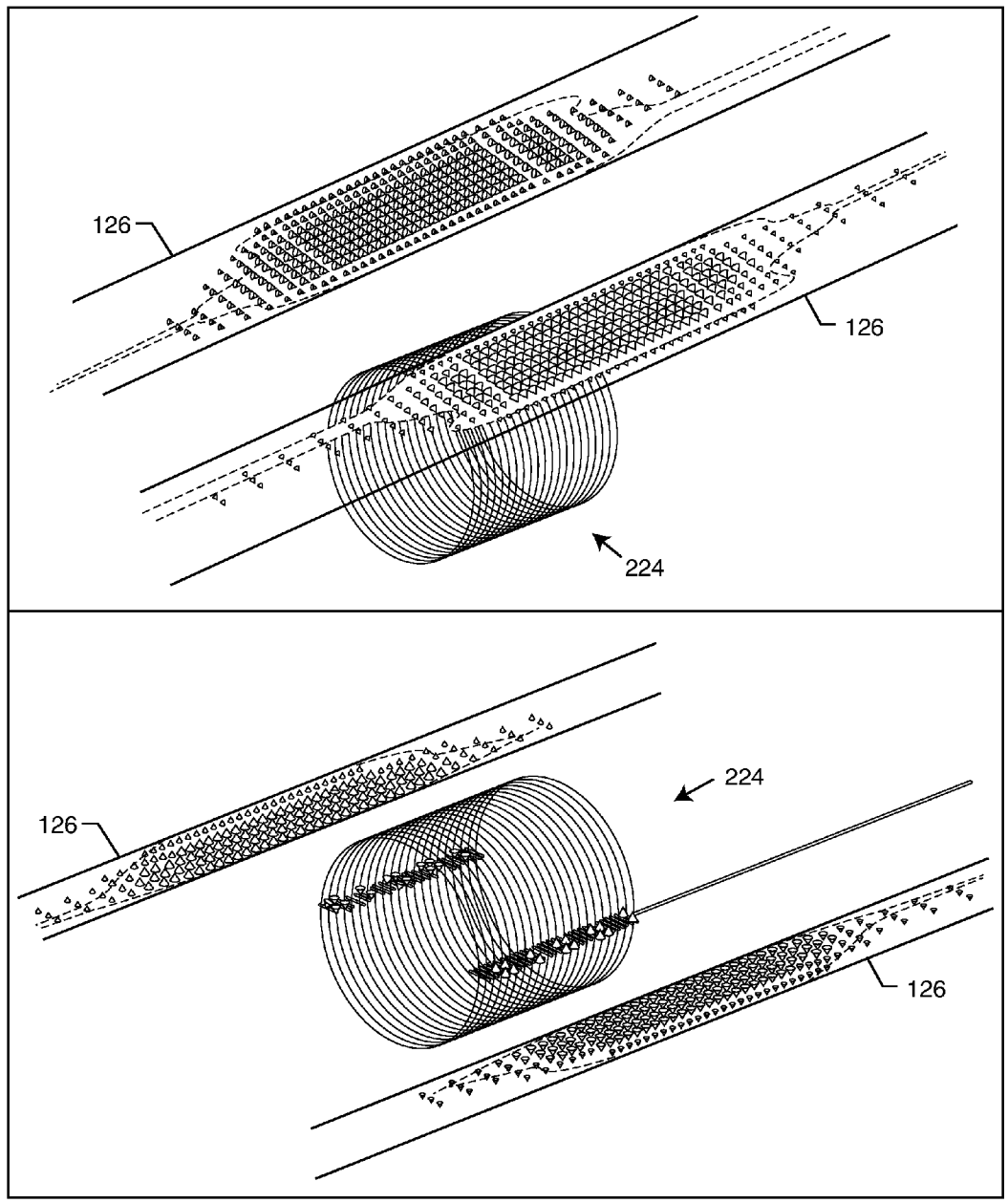
FIG. 46 is a perspective view of the modeling of current flow in an outer conductive shield or housing by a wire wound-type inductor.

Modeling of the two types of inductors has indicated that the modes of current flow are very different between the two. For example, FIG. 45 shows the modeling of current flow in an outer shield or housing 126 for a 63.8 MHz current flow in the coil with the thick film inductor 14. FIG. 46 shows the modeling of current flow in an outer shield or housing 126 for a 63.8 MHz current flow in the coil with the wire wound type inductor 224.

As can be seen in FIG. 45, the thick film type inductor 226' has a current flow that can be related to two saddles placed on the top and bottom of the metallic tube 126. The wire wound type inductor 224 has a current flow that circulates around the tube 126 in a ring like direction (FIG. 46). The ring type flow of the wire wound type inductor 224 would intuitively seem to be better supported than that of the saddle flow of thick film type inductors 226, 226', thereby allowing a stronger interaction between the inductor and the tube 126. The absolute effect of the coil to tube coupling cannot be easily calculated or modeled. Therefore, in order to create a hermetic filter that operates at designed frequency, empirical testing is required.

Compensation of the tube parasitic effect is achieved by creating a series of circuits where the capacitor or inductor value is systematically changed. The empirical data when the circuit is placed in the tube is analyzed for resonance frequency of each circuit. The resonance frequencies are fitted as a function of the capacitor or inductor values. From the fitting results an ideal capacitor or inductor value can be determined which will result with the required resonance frequency when the circuit is placed in the tube.

The use of the thick film inductor 226, 226' requires a smaller modification of the capacitor or inductor value. In some cases the tolerance range may be such that no modification is required, since this design minimizes the induced eddy currents on the conductive shield or housing 126.

Figure 47:
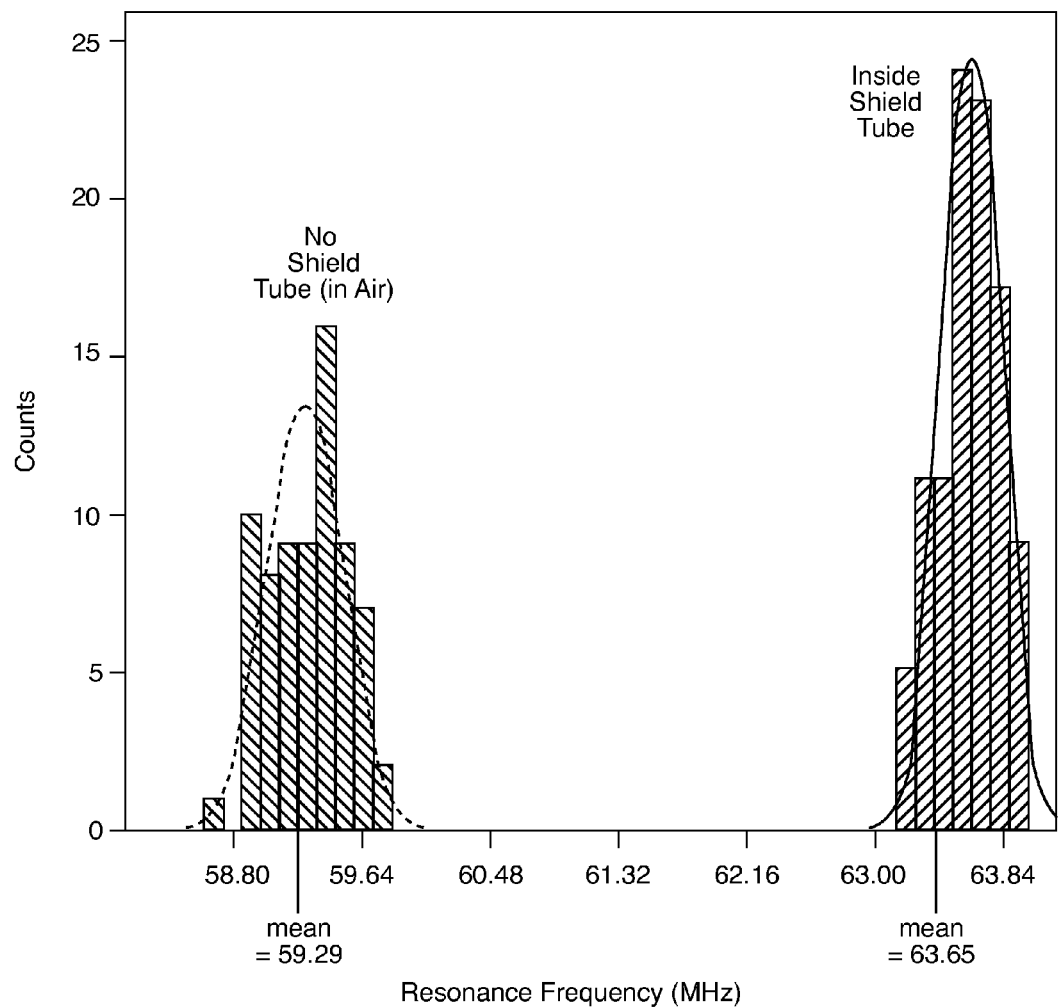
FIG. 47 is a graph of histograms from various prototypes of solenoid inductors.

FIG. 47 is a graph of histograms from various prototypes of solenoid inductors that were built as a component of L-C resonant bandstop filters. A network analyzer was used to measure the resonant frequency of the bandstop filter within the limit of the component tolerances of the inductors and capacitors. The left hand histogram is a graph of the L-C bandstop filter resonant frequencies measured with the bandstop filter disposed well outside of the overall conductive shield 126 (in other words, in air). The mean resonant frequency was measured to be 59.29 MHz with a standard deviation of 0.2486 based on 71 units measured. Then the bandstop filters were placed inside of a shielded housing 126 and again their resonant frequencies were measured. In this case the mean resonant frequency was determined to be 63.65 MHz with a standard deviation of 0.1958 with a total of 100 samples measured. In all cases, the capacitors were 15.9 picofarads and mounted on circuit boards similar to those shown in FIG. 24. In this case, the shielded housing was made of platinum-iridium. Remarkably, this effect on the inductor fields accounts for a shift in resonant frequency of the bandstop filter of 4.3 MHz or 6.8%. The frequency of resonance $f_r$ for a bandstop filter is given in FIG. 16 where one can see there is an inverse relationship between the square root of the inductance and capacitance and the resonant frequency. Assuming the capacitance is held constant at 15.9 picofarads and solving the resonant frequency equation for inductance, this means that the inductance in air on average was 453.2 nanoHenries and dropped to an effective 394.3 nanoHenries when inserted into the surrounding EMI shield housing 126.

This is an average shift of 58.9 or approximately 59 nanoHenries, which is about a 13% shift in the inductance value. Accordingly, in order for the L-C bandstop filter to be properly resonant in an MRI RF pulsed center frequency, this shift in the inductance in aft versus insertion into the MRI shield 126 must be properly accounted for. There are many variables that come into play in this calculation, including the physical properties of the inductor, its orientation as a solenoid or a chip inductor, the thickness and diameter of the surrounding electromagnetic shield and its high frequency material properties, including its high frequency resistance.

Figure 48:
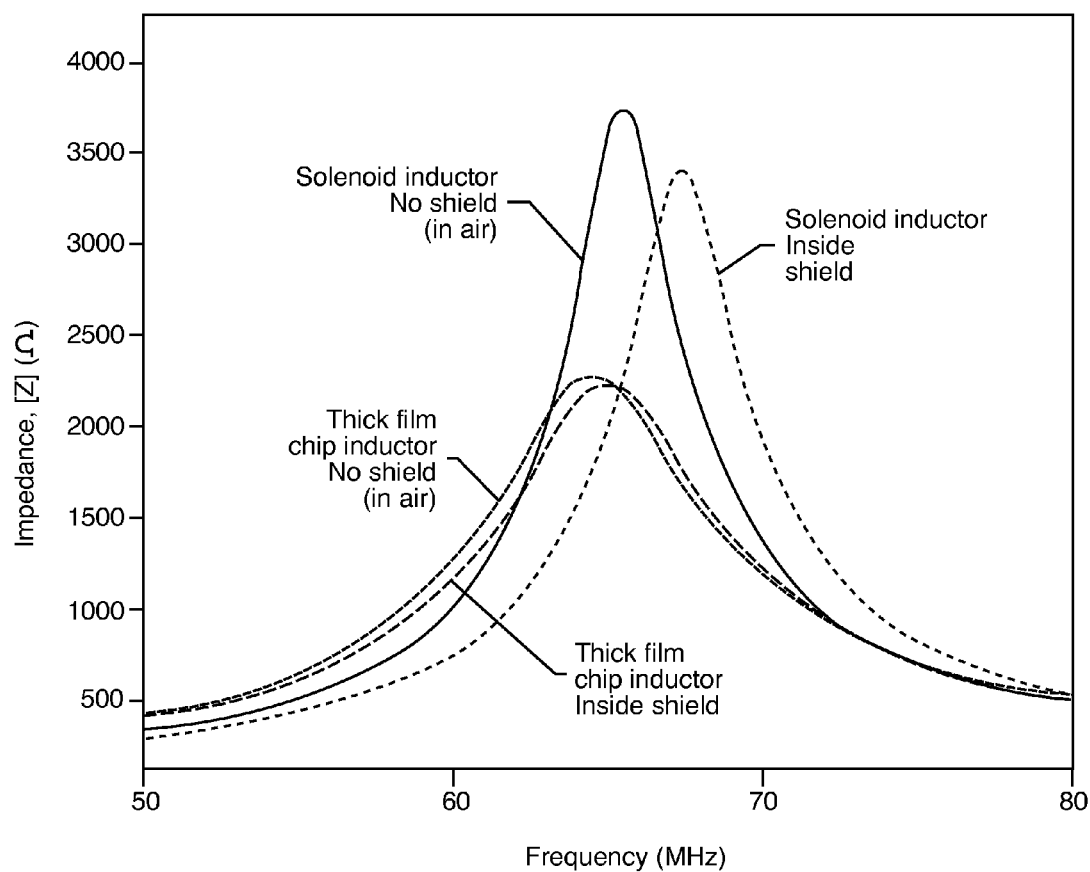
FIG. 48 is a graph of impedance versus frequency curves for circuits boards with either thick film chip or wire wound or solenoid inductors, when shielded in comparison to when not shielded.

FIG. 48 illustrates impedance versus frequency curves for circuit boards with either thick film chip or wire wound or solenoid inductors (the primary magnetic field line axis and corresponding magnetic fields of a typical thick film inductor are oriented at 90 degrees to a typical wire wound solenoid inductor). This graph demonstrates the effect of placing the thick film 226 or wire wound 224 inductor inside a cylindrical metal shield tube 126. Notice that the solenoid-type wire wound inductor boards exhibit a significant shift in resonant frequency and impedance. Having a very high impedance at resonance is desirable to prevent undesirable MRI RF induced currents from flowing into surrounding body tissues.

Figure 49:
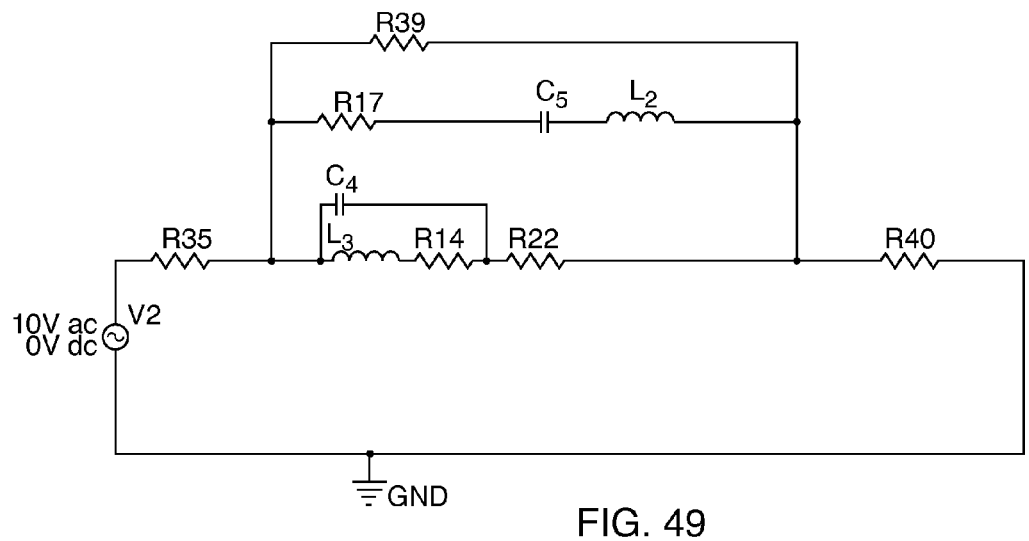
FIG. 49 is a PSPICE computer model for predicting the resonant circuit behavior of a solenoid inductor in air.
Figure 50:
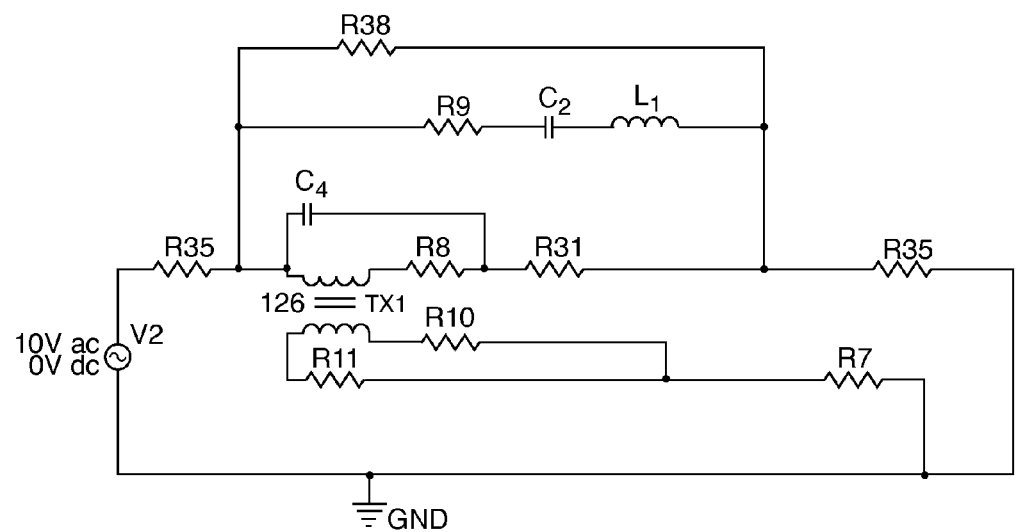
FIG. 50 is a PSPICE computer model similar to FIG. 49, modified to add mutual inductance coupling to a surrounding electromagnetic shield.

FIG. 49 is a PSPICE computer model developed by the inventors to be able to predict the resonant circuit behavior of a solenoid inductor in air. This model was modified as shown in FIG. 50 to add mutual inductance coupling to a surrounding conductive shield or housing 126. This PSPICE model is used in conjunction with the present invention to predict that amount of resonant shift and the amount of inductive offset one needs to make while designing inductors for shielded L-C bandstop filters.

Figure 51:
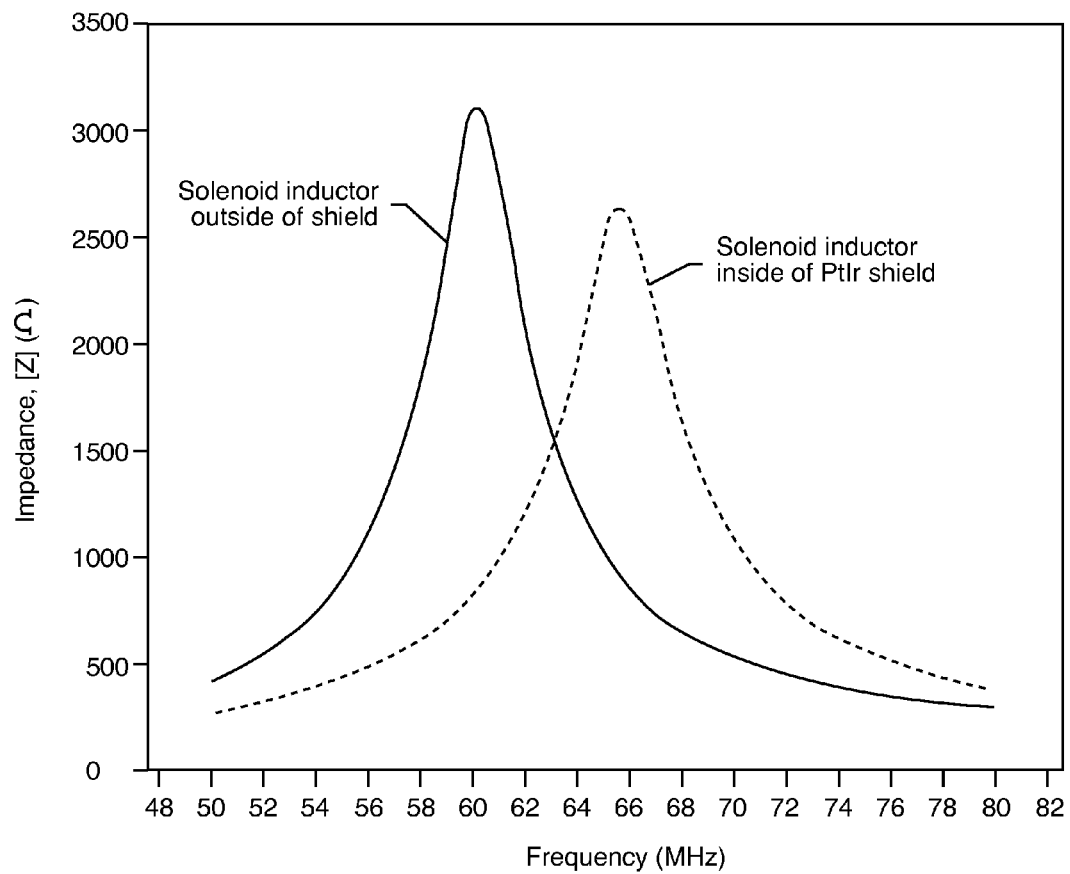
FIG. 51 is a graph of the frequency response predicted by the PSPICE models of FIGS. 49 and 50.

FIG. 51 is the frequency response predicted by the PSPICE models for the inductor inside and outside of a platinum-iridium shielded housing 126. As one can see, the PSPICE model very accurately fits the empirical data previously plotted in FIG. 48.

The PSPICE model can be used to adjust a first inductive value with the inductor outside of a shielded housing so that a second inductive value with the inductor inside of a shielded housing has the proper value. For example, in a resonant tuned L-C bandstop filter is very important that the inductor value and the capacitor value have a fairly tight tolerance so that the resulting resonant frequency occurs in the center of a range of MRI RF pulsed frequencies.

Figure 52:
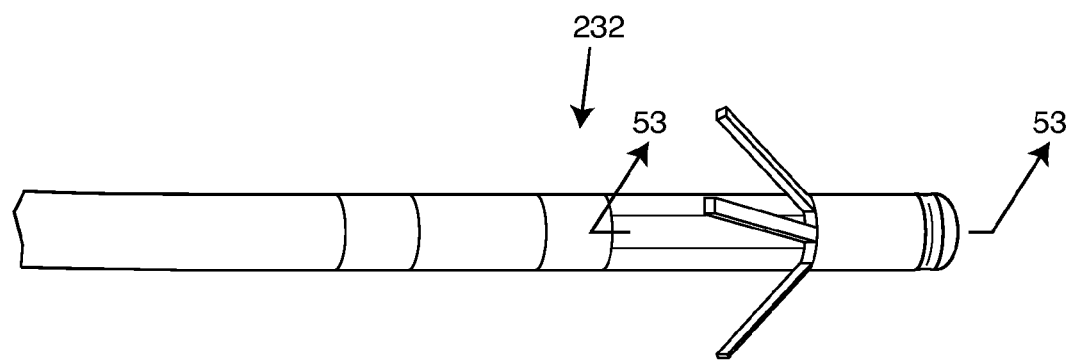
FIG. 52 is a perspective view of a passive electrode fixation tip typically used in cardiac pacemaker applications.

With reference now to FIG. 52, a passive electrode fixation tip 232 typically used in cardiac pacemaker applications is shown in which the shielded inductor, passive network or bandstop filter assembly of the present invention can be incorporated.

Figure 53:
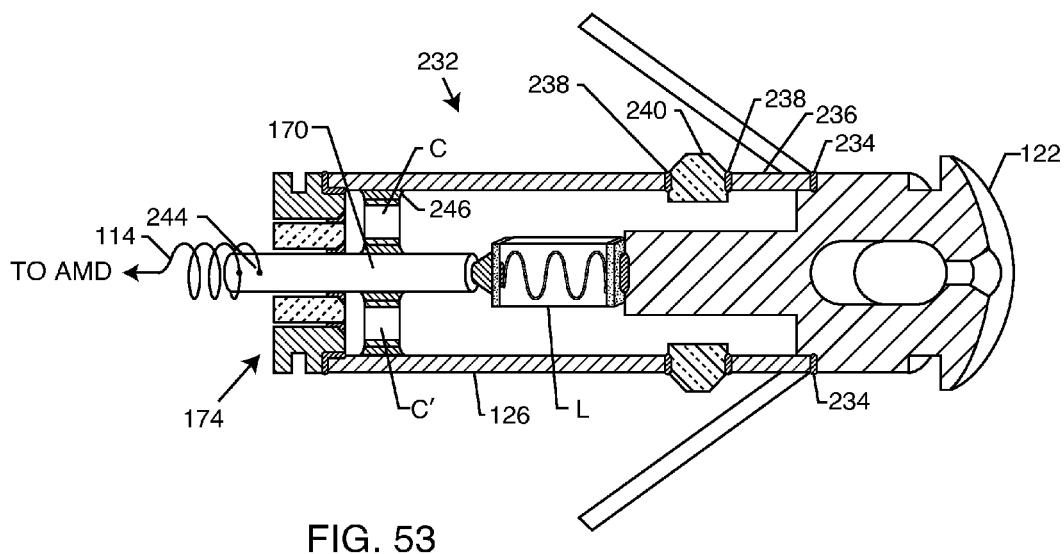
FIG. 53 is an enlarged sectional view taken generally along line 53-53 from FIG. 52.

FIG. 53 is a sectional view of a portion of the passive electrode 232 taken along the line 53-53 from FIG. 52, and illustrates a hermetically sealed package consisting of a passive distal tip electrode 122 which is designed to be in intimate contact with body tissue, such as inside the right atrium of the heart. A hermetic seal is formed at laser weld 234 as shown between the tip electrode 122 and a metallic ring 236. Gold brazes 238 are used to separate the metallic ring 236 from the shield surface 126 by use of an intervening insulator 240. This insulator 240 could typically be of alumina ceramic, other types of ceramic, glass, sapphire or the like. The shield or housing 126, which also acts as an energy dissipating surface EDS, is typically gold brazed to the other side of the insulator 240 as shown. An inductor L, such as an inductor chip is shown connected between the distal tip electrode 122 and a terminal pin 170 which is attached as by laser welds 244 to the end of the lead 114 extending through the body to the AMD. As shown, terminal pin 170 protrudes through a hermetic seal assembly 174.

The shield/energy dissipating surface 126 of FIG. 53 is typically of a biocompatible metal, such as titanium, platinum or the like. It is important that the shield/energy dissipating surface 126 be both electrically conductive and thermally conductive so that it can transfer RF and thermal energy into body fluid or tissue. The shield/energy dissipating surface 126 can be roughened or even corrugated or bellowed to increase its surface area and therefore its energy dissipating properties into surrounding body fluids or body tissue.

Figure 55:
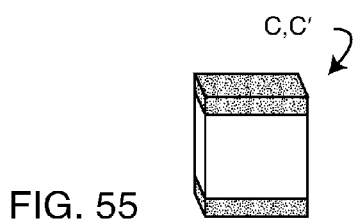
FIG. 55 is a perspective view of a typical off-the-shelf commercial monolithic ceramic capacitor (MLCC)

Capacitive elements C and C' shown in FIG. 53 are designed to act as a low impedance at higher frequencies. Electrical connections 246 couple the capacitor C to the shield/energy dissipating surface 126. This forms a broadband low pass filter wherein the inductor L acts in cooperation with the capacitive elements C and C'. The presence of the inductor L enhances the performance of the capacitor elements C and C', which are typical off-the-shelf commercial monolithic ceramic capacitors (MLCCs) such as those illustrated in FIGS. 55 and 56.

An advantage in using a capacitor C as a selective frequency element is that it tends to act as a broadband filter which will attenuate a range of MRI frequencies. For example, placement of an effective capacitor C could attenuate 64 megahertz, 128 megahertz and higher MRI frequencies. However, if one were to use an L-C series trap filter as shown in FIG. 8, then this would only be effective at one MRI frequency, for example 64 megahertz only. Of course, one could use multiple L-C trap filters. However, in a preferred embodiment the use of a capacitor as is desirable because with a two-element L-type low pass filter, one can attenuate a broad range of MRI RF pulsed frequencies.

Figure 54:
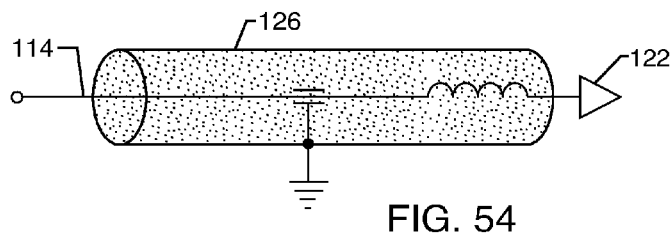
FIG. 54 is an electrical schematic diagram for the circuit of FIG. 53.

The schematic diagram for the circuitry of FIG. 53 is shown in FIG. 54. Capacitors C and C are actually in parallel and act as a single capacitive element. The reason for multiple capacitors is to obtain a high enough total capacitance value so that the capacitive reactance is very low at the frequency of interest (for example, 64 MHz for a 1.5 T MR system).

Figure 56:
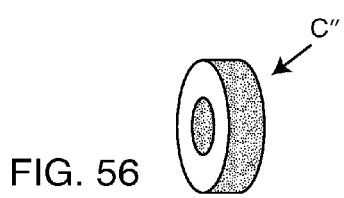
FIG. 56 is a perspective view of a typical off-the-shelf commercial unipolar feedthrough capacitor.

An alternative capacitor C'' for use in the circuit of FIG. 53, known as a unipolar feedthrough capacitor, is shown in FIG. 56. It has outside diameter and inside diameter termination surfaces and for electrical contact. Feedthrough capacitors can be unipolar or multipolar. These are completely described in the prior art; for example, refer to U.S. Pat. No. 7,363,090, U.S. Pat. No. 4,424,551; U.S. Pat. No. 5,333,095; and U.S. Pat. No. 6,765,779.

Figure 57:
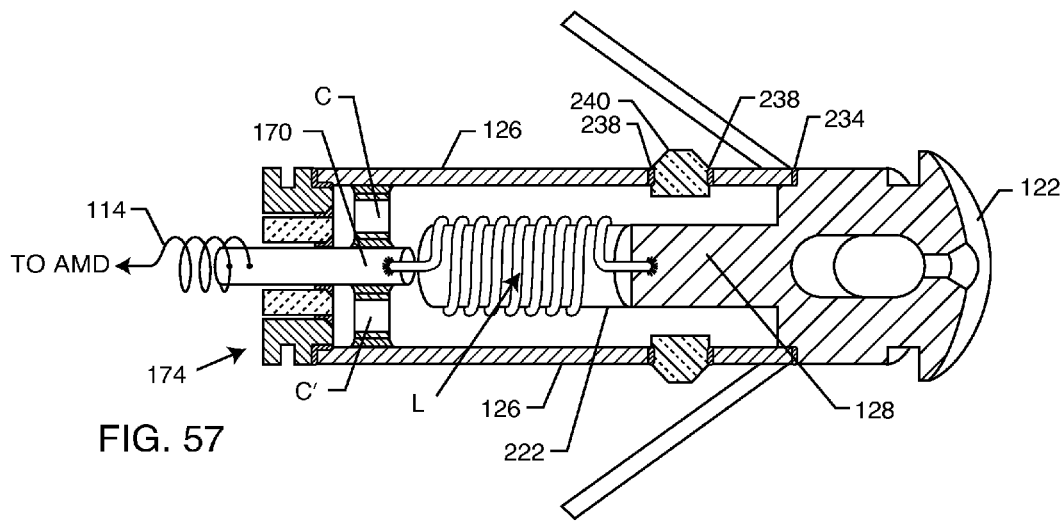
FIG. 57 is a sectional view similar to FIG. 53, except that the inductor element is wire wound around a non-ferromagnetic mandrel.

FIG. 57 is similar to FIG. 53 except that the inductor element L is wire wound around a non-ferromagnetic mandrel 222 (formed from a material such as a ceramic or plastic). This type of solenoid wound inductor L has much higher current handling capability as compared to the inductor chip of FIG. 53. The inductor chip of FIG. 53 can be fabricated from a variety of shapes including Wheeler spirals, thick film inductors, and the like. It is important that the inductor element L be able to handle substantially high currents when it is in series with the lead 114. The reason for this has to do with either ICD applications for shock electrodes or automatic external defibrillation (AED) events. AEDs have become very popular in government buildings, hospitals, hotels, and many other public places. When the external defibrillator paddles are placed over the chest of a cardiac pacemaker patient, the high voltage that propagates through body tissue can induce powerful currents in implanted leads. Accordingly, the inductor L has to be designed to handle fairly high current (as high as the 4 to 8 amp range in short bursts). The wire wound inductor L of FIG. 57 has wire of a larger cross-sectional area and is therefore a higher current handling inductor.

Figure 58:
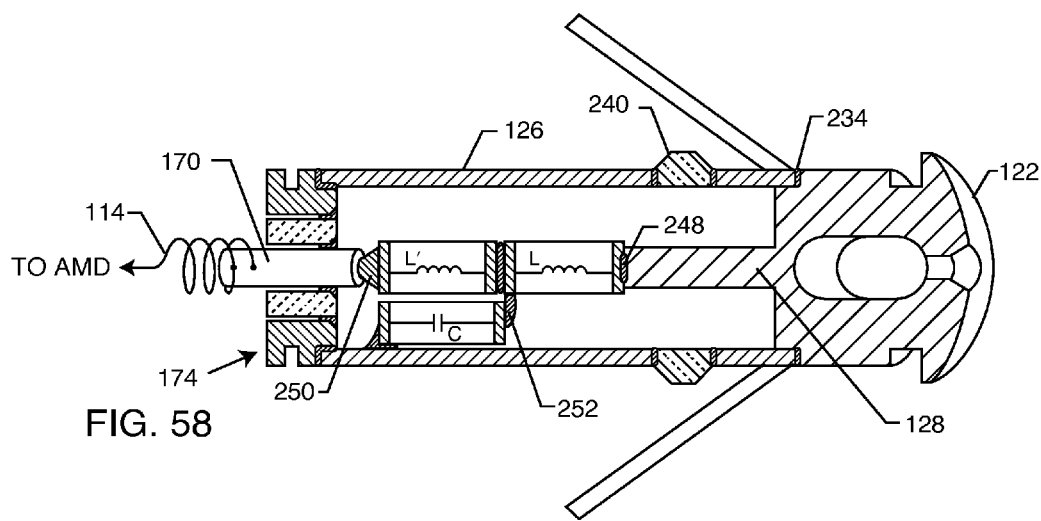
FIG. 58 is a sectional view similar to FIGS. 53 and 57 wherein a pair of inductors are coupled in connection with a capacitor to form a "T" filter within the passive electrode tip.

FIG. 58 illustrates an entirely different approach for the diverting of RF energy away from the electrode tip 122 to the shield/energy dissipation surface 126. Shown is an electrical connection 248 between a first inductor L and the distal tip electrode assembly 122. The other end of the first inductor L is connected to a second inductor L' which is in turn electrically connected at 250 to the hermetic terminal pin 170. The capacitor C is connected between the junction of the two inductors L and L' at electrical connection 252. The other end of the capacitor is electrically connected to the shield energy dissipating surface 126. An insulating sleeve (not shown) can be used to ensure that the capacitor termination and electrical connection 252 does not inadvertently make contact (short out) with the shield/energy dissipating surface 126.

Figure 59:
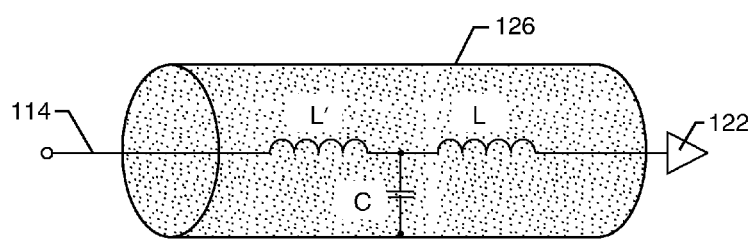
FIG. 59 an electrical schematic for the structure shown in FIG. 58.

The electrical schematic for FIG. 58 is shown in FIG. 59. This forms a low pass filter (in this example, a T-filter), which tends to enhance the filtering performance by directing more of the RF energy to the shield/energy dissipating surface 126. As previously mentioned, a single or multi-element low pass filter would attenuate a broad range of MRI frequencies and would be an advantage in the present invention for that reason. In accordance with the present invention, it is important that the value of the inductance for either the chip inductor L of FIG. 53, the solenoid inductor L of FIG. 57, or the chip inductors L, L' of FIG. 58 have their first inductive values adjusted so that their inductance, when inserted into the overall shield/energy dissipating surface 126, so that the resultant package value is correct.

Figure 60:
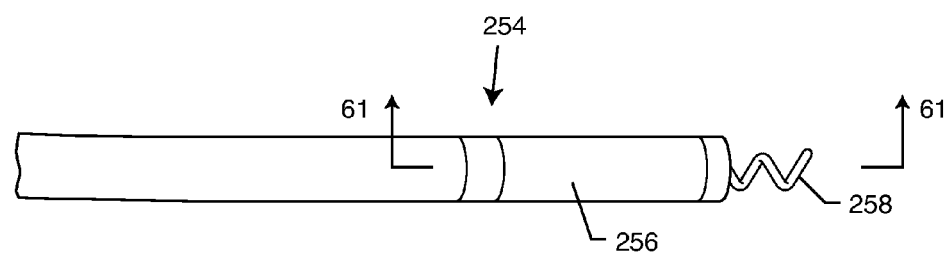
FIG. 60 is a perspective view of a generic prior art active fixation distal tip typically used in conjunction with cardiac pacemakers.
Figure 61:
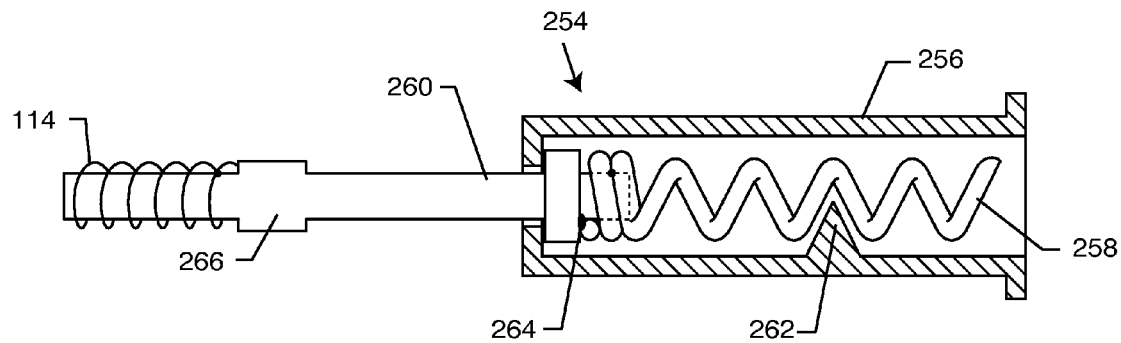
FIG. 61 is an enlarged sectional view taken generally along line 61-61 from FIG. 60.

FIGS. 60 and 61 show a generic prior art active fixation distal tip electrode 254 which is typically used in conjunction with cardiac pacemakers. There is a metallic housing 256 which contains a sharp tipped distal helix coil 258. In FIG. 61, this helix coil 258 is shown in its retracted position, which enables the physician to insert the fixation tip assembly 254 endocardially through the venous system, through the atrium, and through the tricuspid valve into the right ventricle so it does not snag or tear any tissue, and is designed to be extended and screwed into myocardial tissue. Once it is in the appropriate position, the physician then turns leadwire spline assembly 260 in a clockwise rotation. This is done outside the pectoral pocket with the lead 114 protruding from the body. A torque tool is generally applied so that the physician can twist or screw the helix coil 258 into place. Protrusion 262 acts as a gear so that as helix coil 258 is turned, it is screwed forward. This makes for a very reliable fixation into myocardial tissue. The helix coil 258 is generally attached by a laser weld 264 to an end of the spline assembly 260 as shown. Attached to spline assembly 260, usually by laser welding, is the lead 114 coming from the AMD. An optional feature 266 is placed on spline assembly 260 to create a positive stop as the physician is turning the leadwire assembly and screwing the helix coil 258 into body tissue. Of course, all of the materials of the active fixation tip 254 shown in FIG. 61 are biocompatible. Typically, the helix coil 258 is made of platinum iridium alloy and would be coated with various materials to improve electrical performance. The housing 256 would generally be composed of titanium or another equivalent biocompatible alloy. The spline 260 is generally a platinum iridium alloy.

Figure 62:
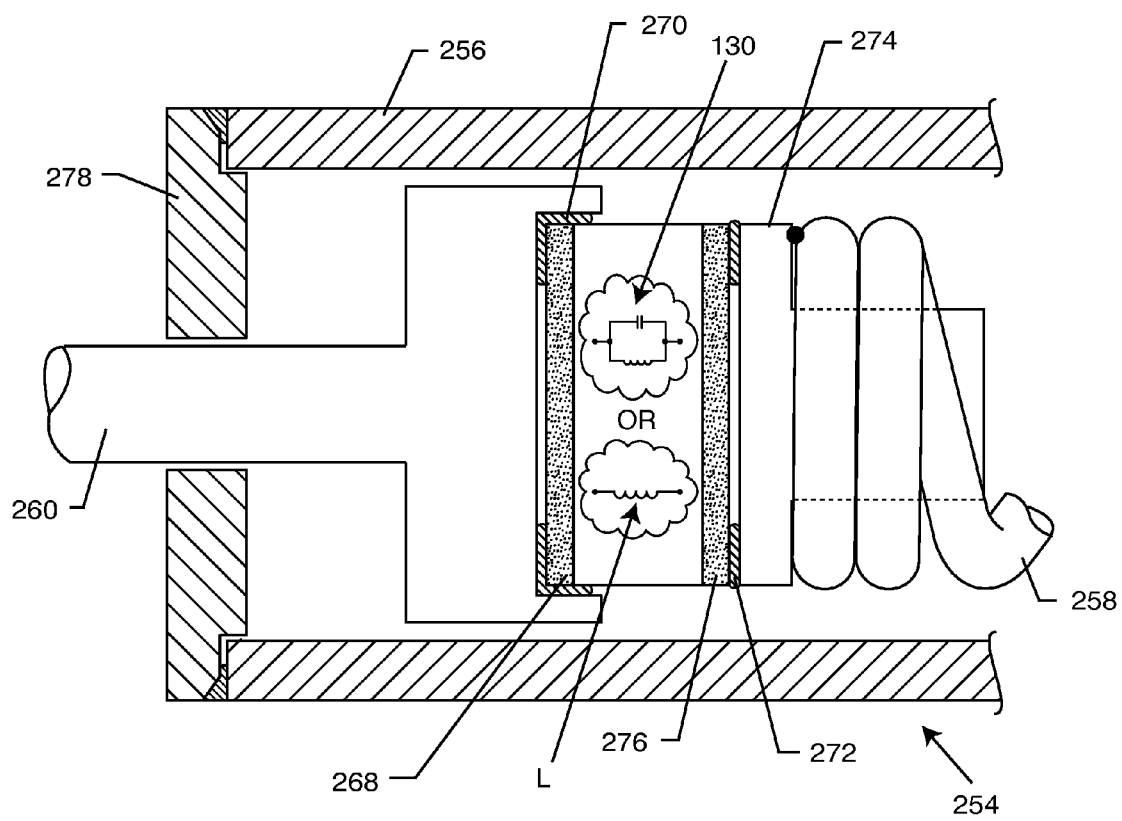
FIG. 62 is a fragmented sectional view of a portion of the active fixation tip of FIGS. 60 and 61, modified to include a shielded inductor or bandstop filter in accordance with the present invention.

FIG. 62 illustrates applying a shielded inductor L or a bandstop filter 130 to the active fixation distal tip 254 shown in FIG. 61. One can see the attachment from the metallization 268 of inductor L or bandstop filter 130 shown attached to the spline 260. This is typically accomplished by a gold braze preform 270. In this case, the spline 260 has been counterbored to receive the end of inductor L or bandstop filter 130. This allows the gold braze material 270 to angle up along the sides of the assembly, thereby adding shear strength. A similar gold braze preform 272 is used to attach a distal tip helix pedestal 274 to the metallization 276 of the inductor or passive network assembly. Of particular advantage is that the assembly illustrated in FIG. 62 can be constructed entirely of low k, very high strength ceramics. In this case, pure alumina or porcelain would be preferred embodiments. These have the advantage of being mechanically very rugged and also very rugged to thermal shock such that it would take pure gold brazing. By use of all biocompatible materials, the assembly is greatly simplified in that it need not be hermetic. It would also be possible to replace the gold brazes 270 and 272 with equivalent laser welds. One can see that the end cap 278 has been modified in a novel way such to make it flush with the outside diameter of the housing 256. This allows one to increase the inside diameter allowing room for the counter-bore in the spline assembly 260. The metallic end cap 278 has been stepped so that it is seated for convenient fixturing. The overall housing 256 for the translatable helix assembly 254 is conductive and forms a shield in accordance with the present invention around either the inductor L or the bandstop filter 130. Of course, the inductor L or bandstop filter 130 could be replaced with any low or high pass filter and/or active electronic circuit.

Figure 63:
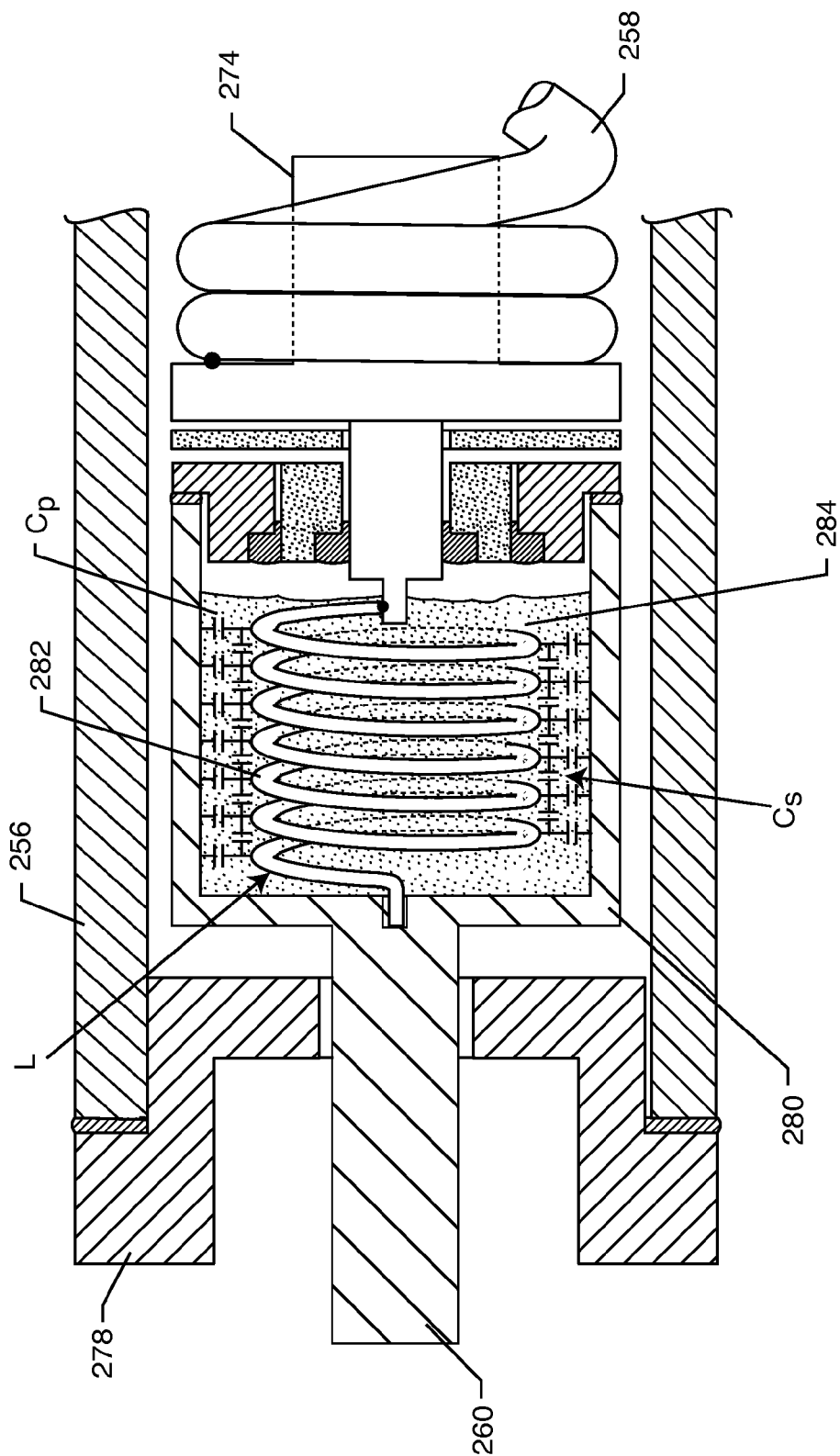
FIG. 63 is a sectional view similar to FIG. 62, where an inductive coil is disposed within a dielectric material such that parasitic capacitances form, with the inductor coil itself, a bandstop filter.

FIG. 63 is an adaptation of the generic prior art active fixation distal tip 254 illustrated in FIG. 62. The design allows: 1) body fluid to freely penetrate to all surfaces interior to the active fixation distal tip 254; and 2) torque experienced by the helix 258 is not transmitted to any electronic component, such as the hermetically sealed bandstop filter 130 and its associated electrical and mechanical connections. The spline shaft 260 has been modified such that it has a relatively long, hollow cylindrical cup portion 280 which allows for installation of the inductor L or bandstop filter 130 inside of it. As will be seen, this will offer a number of important mechanical and biocompatibility advantages. The inductor coil 282 has either been wound around a mandrel which has been removed or is wound around a mandrel which is non-ferromagnetic. In the preferred embodiment, the coil 282 is free standing and is then backfilled with an insulative dielectric material 284. The dielectric insulating material 284 is preferably dispensed as a thermal-setting liquid. After curing at high temperature, the insulating material 284 is cured to form a solid. This material can be a thermal-setting non-conductive epoxy or polyimide or the like. An alternative (not shown) would be to insert a rigid insulating sleeve around the inductor, which has a pre-formed shape. This could be used in combination with insulated inductive wire turns to control the series and parallel parasitic capacitance. The space in between the turns of the coil 282 and its relationship to the cup assembly 280 is important as parasitic capacitances Cp and Cs are developed.

Figure 64:
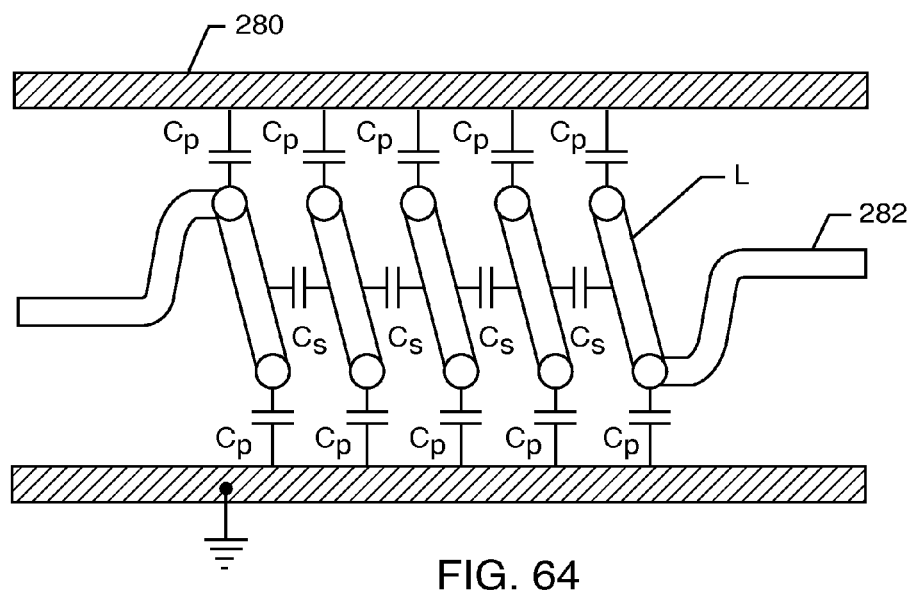
FIG. 64 is an equivalent cross-section schematic diagram for the structure shown in FIG. 63.
Figure 65:
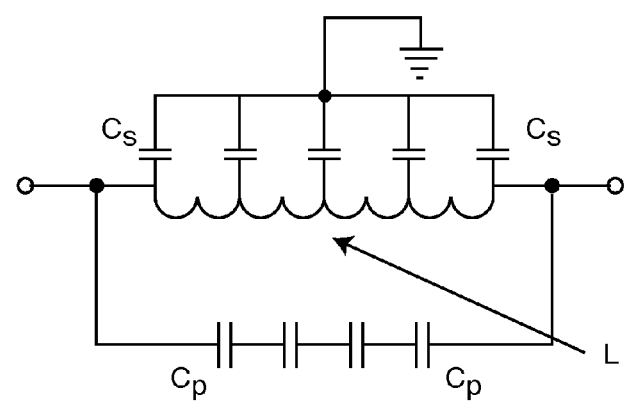
FIG. 65 is an electrical schematic for the structure shown in FIGS. 63 and 64.
Figure 66:
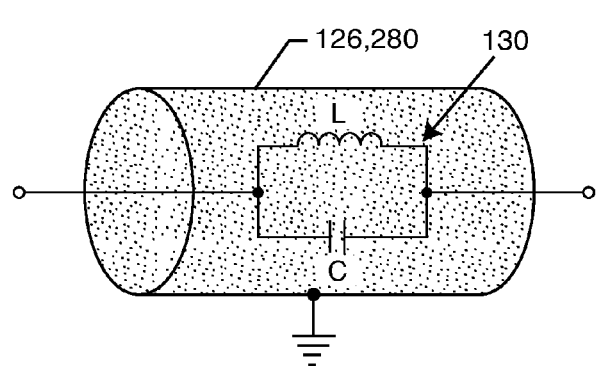
FIG. 66 is a simplified electrical schematic of the structure shown in FIGS. 63-65.

This arrangement is best understood by looking at the equivalent cross-sectional schematic diagram illustrated in FIG. 64. One can see that there are parasitic capacitances Cs formed between the coil turns and also parasitic capacitances Cp to the outer shield housing cup assembly 280. As shown in the schematic in FIG. 65, all of these capacitances add up to form a capacitance in parallel with the inductor L. Once the schematic of FIG. 65 is simplified, it becomes a shielded parallel resonant bandstop filter 130 as shown in FIG. 66.

An additional advantage of having the inductor L or capacitor-inductor 130 inside the housing 256 of the active fixation tip 254 is that this provides a substantial degree of protection to these delicate electronic components. Doctors and other medical personnel are often notorious in the way they handle lead systems. Things can get dropped, moved or placed against them.

Figure 67:
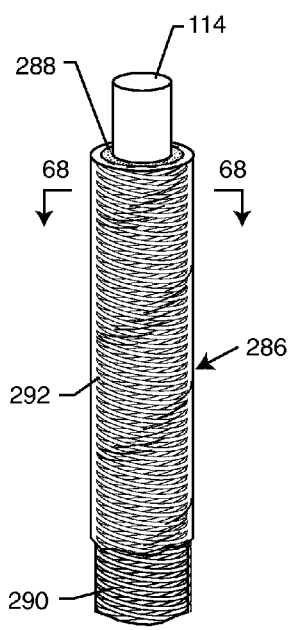
FIG. 67 is a perspective view of a reinforced polyimide tubing that includes the shielding for an inductive component in accordance with the present invention.
Figure 68:
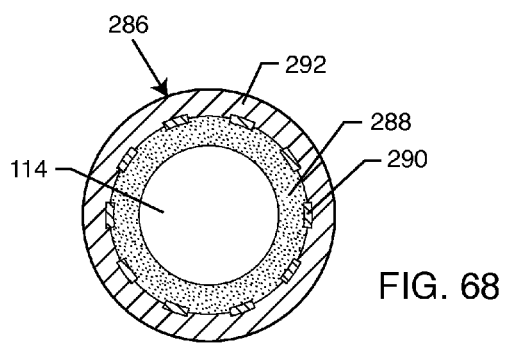
FIG. 68 is an enlarged sectional view taken generally along 68-68 from FIG. 67.

FIG. 67 illustrates a reinforced polyimide tubing 286. The typical construction consists of a substrate layer 288, a braided or coiled metallic shield layer 290 and an exterior layer 292 (see cross section FIG. 68). The substrate 288 and exterior layer 292 are insulative wherein the embedded braided or coiled layer 290 is a conductive metal. In a particularly preferred embodiment, the insulative exterior layer 292 would be eliminated such that the conductive shield 290 would be in direct contact with body fluid. Since the conductive shield 290 has a relatively very large surface area, RF energy can be conducted in the body tissues without resulting in significant temperature rise. This is further described in US 2010/0160997 A1 and US 2010/0023000 A1, both of which are herein incorporated by reference. The most common braid coil 290 material is 304V stainless steel. Other metallic materials can also be used. The embedded braid coil 290 accomplishes RF shielding in accordance with the present invention. FEP and PTFE coatings can be added to the outside diameter both to enhance slickness (lubrication) to make it easy to insert the lead into the body tissues.

Figure 69:
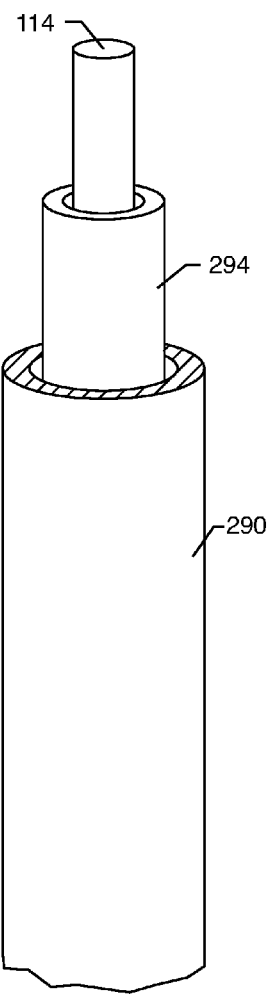
FIG. 69 is similar to FIG. 67, illustrating an alternative embodiment where an insulation tube is slipped over the lead and then a shield layer is slipped over the insulation tube.

FIG. 69 illustrates an alternative embodiment wherein an insulation tube 294 is slipped over the lead 114. Then, a shield layer 290, such as a platinum-iridium, is slipped over the insulation tube 294 as shown.

Figure 70:
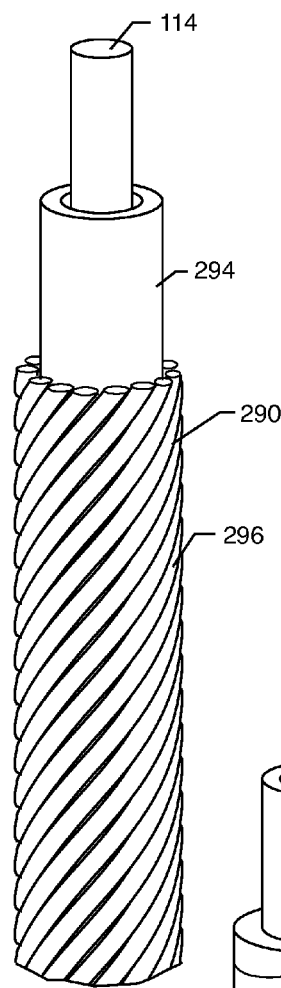
FIG. 70 is similar to FIG. 69, except that the metal shield tube is replaced by wire wound strands.
Figure 71:
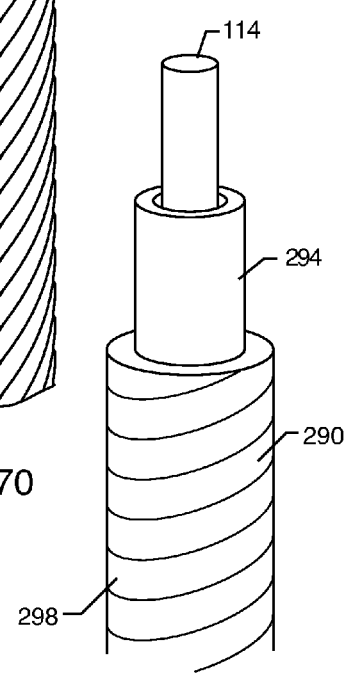
FIG. 71 is similar to FIGS. 69 and 70, except that the metal shield tube or wire wound strands are replaced by wrapped foil.

FIGS. 70 and 71 are similar to FIG. 69 except that the metal shield tube 290 is replaced by wound wire strands 296 or wrapped foil 298, respectively, or other equivalent materials which are commonly used in shielded cables worldwide.

Figure 72:
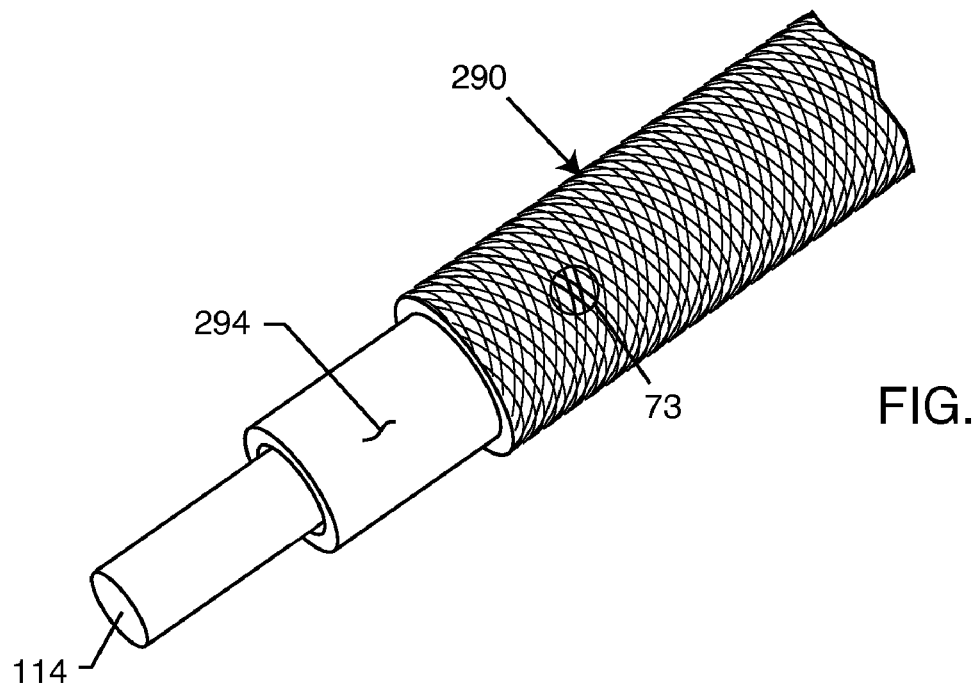
FIG. 72 shows an open mesh cross-braided shield wire instead of the wound shield wire of previous embodiments.
Figure 73:
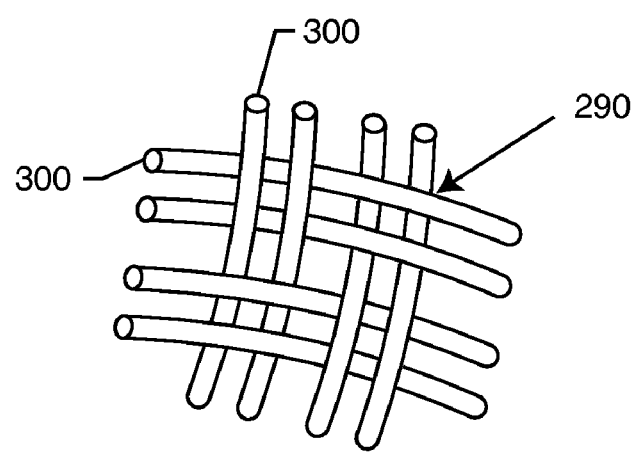
FIG. 73 is an enlarged perspective view of the cross-braided shield of FIG. 72.

FIG. 72 shows an open mesh cross braided shield wire 290 instead of a wound shield wire. The cross braid shield 290 is shown in more detail in FIG. 73, wherein one can see how the braided wires 300 interweave.

The thickness of the conductive shield 290 may require precise control. Thin deposition methods are capable of applying films in the nanometer range. The skin depth or effective skin depth, due to limited conductivity from surface scattering and such, of these thin films may be of a thickness that external electromagnetic waves are not fully attenuated.

Most applications will require full or near-full attenuation to prevent significant currents on the internal sensitive components or connections. However it may be desirable that the energy is not fully attenuated, for example when it is desired to limit the amount of current needed to fully attenuate the incident electromagnetic wave to prevent over-heating. Further, multiple shields may be utilized to prevent overheating or allow limited energy to be attenuated on the internal components to allow monitoring of the external environment for applications such as automatic mode switching or data-logging.

Accordingly, from the foregoing it will be appreciated that the present invention resides in a shielded component or network for an active medical device (AMD) implantable lead which has a length extending from a proximal end to a distal end, all external of an AMD housing. A passive component or network is disposed somewhere here along the length of the implantable lead, the passive component or network including at least one inductive component having a first inductive value. A conductive shield or housing substantially surrounds the inductive component or the passive network. Importantly, the first inductive value of the inductive component is adjusted to account for a shift in its inductance to a second inductive value when shielded. The at least one inductive component also has a primary magnetic field line axis, and the conductive shield or housing has a primary longitudinal axis. The inductive component's magnetic field line axis is oriented substantially orthogonally (70°-110°) to the primary longitudinal axis of the shield or housing.

The inductive component may comprise a simple inductor, a low pass filter, an L-C trap, or a bandstop filter. When a bandstop filter or L-C trap filter is provided, the capacitive and inductive components are tuned to impede induced current flow through the implantable lead at a selected center frequency or range of frequencies, technically an MRI RF pulsed frequency or range of RF pulsed frequencies.

Although several embodiments have been described in detail for purposes of illustration, various modifications may be made without departing from the scope and spirit of the invention. Accordingly, the invention is not to be limited, except as by the appended claims.

What is claimed is:

1. A shielded component or network for an active medical device (AMD) implantable lead, comprising:
    an implantable lead having a length extending from a proximal end to a distal end, all external of an AMD housing;
    a passive component or network disposed somewhere along the length of the implantable lead, the passive component or network including at least one inductive component having a primary magnetic field line axis; and
    a conductive shield or housing substantially surrounding the inductive component or the passive network, the shield or housing having a primary longitudinal axis;
    wherein the inductive component's magnetic field line axis is oriented substantially orthogonally to the primary longitudinal axis of the shield or housing.

2. The shielded component or network of claim 1, wherein the passive component network includes at least one capacitive component electrically connected in parallel with the at least one inductive component to form a bandstop filter.

3. The shielded component or network of claim 2, wherein the inductive component comprises a solenoid inductor, a chip inductor, a Wheeler spiral or a thick film inductor, and wherein the capacitive component comprises a chip capacitor, parasitic capacitance, or a feedthrough capacitor.

4. The shielded component or network of claim 2, wherein the capacitive component comprises parasitic capacitance formed between coils of the inductive component and between the inductive component and the conductive shield or housing.

5. The shielded component or network of claim 4, including a dielectric material disposed between coils of the inductive component and between the inductive component and the conductive shield or housing.

6. The shielded component or network of claim 2, wherein the capacitive component and the inductive component are tuned to impede induced current flow through the implantable lead at a selected center frequency or range of frequencies.

7. The shielded component or network of claim 6, wherein the selected center frequency or range of frequencies comprises an MRI RF pulsed frequency or range of RF pulsed frequencies.

8. The shielded component or network of claim 7, wherein the MRI RF pulsed frequency range includes tens of kilohertz, hundreds of kilohertz, or megahertz.

9. The shielded component or network of any of claims 1, 2 or 6, including a non-conductive insulator or dielectric material disposed between the passive component network and the conductive shield or housing.

10. The shielded component or network of claim 2, comprising:
    an inductor having first and second conductive terminals in spaced non-conductive relation; and
    a capacitor having first and second conductive terminals in spaced non-conductive relation;
    wherein the inductor and the capacitor are physically disposed in series relative to one another; and
    wherein the inductor and the capacitor are electrically connected to one another in parallel.

11. The shielded component or network of claim 10, wherein one of the first or second conductive terminals of the inductor is disposed generally adjacent to one of the first or second conductive terminals of the capacitor.

12. The shielded component or network of claim 11, wherein the capacitor and the inductor are aligned along a common axis.

13. The shielded component or network of claim 11, wherein the adjacent conductive terminals of the inductor and the capacitor abut one another.

14. The shielded component or network of claim 11, including an electrical insulator disposed between the adjacent conductive terminals of the inductor and the capacitor.

15. The shielded component or network of claims 11 or 13, wherein electrical potential between the adjacent conductive terminals of the inductor and the capacitor is minimized.

16. The shielded component or network of claim 15, wherein the electrical potential between the adjacent conductive terminals of the inductor and the capacitor is zero.

17. The shielded component or network of claims 2 or 10, wherein the second conductive terminal of the inductor is conductively coupled to the first conductive terminal of the capacitor, and wherein the first conductive terminal of the inductor is conductively coupled to the second conductive terminal of the capacitor.

18. The shielded component or network of claim 10, comprising a plurality of paired inductor and capacitor bandstop filters, wherein each bandstop filter is physically disposed in series relative to one another.

19. The shielded component or network of claim 18, wherein each paired inductor and capacitor is electrically connected in series to another paired inductor and capacitor.

20. The shielded component or network of claims 18 or 19, wherein the bandstop filters are tuned to impede induced current flows through the implanted lead at different respective selected MRI RF pulsed center frequencies or ranges of RF pulsed frequencies.

21. The shielded component or network of any of claims 2, 6 or 10, wherein the capacitive component and the inductive component comprise biocompatible and non-migratable materials.

22. The shielded component or network of claim 10, wherein the conductive shield or housing comprises a hermetically sealed container in which the inductor and the capacitor are disposed, wherein the hermetically sealed container forms the conductive shield or housing.

23. The shielded component or network of claim 22, wherein the hermetically sealed container comprises a biocompatible housing in which the bandstop filter is disposed, and biocompatible first and second conductive contacts extending through and in non-conductive relation with the housing, and conductively coupled in series to the bandstop filter.

24. The shielded component or network of claim 23, wherein the hermetically sealed container is disposed in series in the implantable lead.

25. The shielded component or network of claim 24, wherein the first and second contacts of the hermetically sealed container are connected to, respectively, proximal and distal portions of the lead.

26. The shielded component or network of claim 23, including a substrate onto which the inductor and the capacitor are fixed in a pre-assembly prior to insertion into the biocompatible housing.

27. The shielded component or network of claim 26, including first and second hermetic terminals comprising at least a portion of the first and second conductive contacts, respectively.

28. The shielded component or network of claim 27, wherein the hermetic terminals are hermetically sealed to the biocompatible housing after the pre-assembly is inserted therein.

29. The shielded component or network of claim 22, including an electrically insulative conformal coating over at least a portion of the hermetically sealed container.

30. The shielded component or network of any of claims 2, 6 or 10, wherein the overall Q of the bandstop filter is selected to balance impedance at the selected frequency versus frequency bandwidth characteristics.

31. The shielded component or network of claim 30, wherein the Q of the inductive component is relatively high, and the Q of the capacitive component is relatively low, and wherein the inductive component has a relatively low resistive loss, and the capacitive component has a relatively high equivalent series resistance.

32. The shielded component or network of claim 30, wherein the Q of the inductive component is relatively low, and the Q of the capacitive component is relatively high, and wherein the inductive component has a relatively high resistive loss, and wherein the capacitive component has a relatively low equivalent series resistance.

33. The shielded component or network of claim 1, including an impeding circuit for raising the high frequency impedance of the implantable lead.

34. The shielded component or network of claim 33, wherein the impeding circuit comprises an inductor.

35. The shielded component or network of claim 33, wherein the impeding circuit comprises a bandstop filter.

36. The shielded component or network of claim 1, wherein the inductive component comprises a plurality of spaced apart inductive components disposed along the length of the implantable lead.

37. The shielded component or network of claim 36, wherein less than all of the inductive components are shielded.

38. The shielded component or network of any of claims 1, 3, 4 or 5, wherein the conductive shield or housing comprises a plurality of conductive shields disposed along the length of the implantable lead.

39. The shielded component or network of claim 1, wherein the conductive shield or housing comprises a conductive heat-shrink tubing, a conductive foil, wire, braid, mesh, circuit trace, or solid tubular material, or a conductive polymer, a conductive epoxy, nano-fibers, nano-meshes, nano-coatings or nano-threads.

40. The shielded component or network of claim 1, wherein the conductive shield or housing is radially spaced from the passive component network.

41. The shielded component or network of claim 1, wherein the conductive shield or housing comprises MP35N, iridium, carbon, platinum, titanium, palladium, chromium, Wolfram, tungsten, gold, copper, or alloys thereof.

42. The shielded component or network of claim 1, wherein the implantable lead comprises a plurality of implantable leads substantially surrounded by the conductive shield or housing.

43. The shielded component or network of claim 1, wherein the AMD comprises an implantable hearing device, a cochlear implant, a piezoelectric sound bridge transducer, a neurostimulator, a brain stimulator, a cardiac pacemaker, a left ventricular assist device, an artificial heart, a drug pump, an implantable bone growth stimulator, a urinary incontinence device, a spinal cord stimulator, an anti-tremor stimulator, an implantable cardioverter defibrillator, or a congestive heart failure device.

44. The shielded component or network of claim 1, wherein the conductive shield or housing comprises a housing for a passive fixation tip.

45. The shielded component or network of claim 1, wherein the conductive shield or housing is associated with a translational active fixation tip.

46. The shielded component or network of claim 45, wherein a housing for the active fixation tip comprises the conductive shield or housing.

47. The shielded component or network of claim 45, wherein the conductive shield or housing is disposed within a housing for the active fixation tip.

48. The shielded component or network of claim 1, wherein the network includes an active electronic circuit.

49. The shielded component or network of claim 1, wherein the conductive shield or housing comprises a non-metallic material having a thin conductive coating applied thereto.

50. The shielded component or network of claim 49, wherein the non-metallic material comprises sapphire, ruby, alumina or ceramic material.

51. The shielded component or network of claim 49, wherein the conductive coating is applied by plating, chemical vapor deposition, sputtering, physical application or cladding.

52. The shielded component or network of claim 1, wherein the conductive shield or housing surrounds less than the entire length of the lead.

* * * * *